(12) United States Patent
Hoen et al.

(10) Patent No.: US 12,377,420 B2
(45) Date of Patent: Aug. 5, 2025

(54) SYSTEM AND METHOD FOR FOOD WASTE DECOMPOSITION

(71) Applicant: Green Eco International Ltd, Victoria (AU)

(72) Inventors: Jason Hoen, Victoria (AU); Rohan Dinn, Victoria (AU); Paul Newman, Lancashire (GB); Neal Rothwell, Lancashire (GB); Siamak Sharifi-Jamali, Lancashire (GB); Brian McCartney, Lancashire (GB); Stephen Pinchen, Derbyshire (GB); Paul Bush, Lancashire (GB); Neil Brierley, Lancashire (GB)

(73) Assignee: Green Eco International Ltd (AU)

( * ) Notice: Subject to any disclaimer, the term of this patent is extended or adjusted under 35 U.S.C. 154(b) by 928 days.

(21) Appl. No.: 16/975,979

(22) PCT Filed: May 25, 2018

(86) PCT No.: PCT/AU2018/050517
§ 371 (c)(1),
(2) Date: Aug. 26, 2020

(87) PCT Pub. No.: WO2019/169425
PCT Pub. Date: Sep. 12, 2019

(65) Prior Publication Data
US 2021/0039109 A1 Feb. 11, 2021

(30) Foreign Application Priority Data
Mar. 9, 2018 (AU) ................................ 2018900780
May 11, 2018 (AU) ................................ 2018901669

(51) Int. Cl.
*B09B 3/00* (2022.01)
*A61L 11/00* (2006.01)
(Continued)

(52) U.S. Cl.
CPC ............ *B02C 18/067* (2013.01); *A61L 11/00* (2013.01); *B02C 18/0092* (2013.01);
(Continued)

(58) Field of Classification Search
CPC ... B02C 18/067; B02C 18/0092; B02C 23/24; A61L 11/00; A61L 9/22; B09B 3/00;
(Continued)

(56) References Cited

U.S. PATENT DOCUMENTS 5,340,036 A 8/1994 Riley
5,465,503 A 11/1995 Oates
(Continued)

FOREIGN PATENT DOCUMENTS

AU 2019210824 8/2019
CN 2110837 U 7/1992
(Continued)

OTHER PUBLICATIONS

International Searching Authority/Australian Patent Office, "Notification of Transmittal of the International Search Report and The Written Opinion of the International Searching Authority, or the Declaration," for PCT/AU2018/050517, dated Aug. 29, 2018, 11 pages.

*Primary Examiner* — Huy Tram Nguyen
(74) *Attorney, Agent, or Firm* — Haynes and Boone, LLP

(57) ABSTRACT

Machines, processes and methods in relation to processing of waste, in particular food waste or organic waste are provided. Some embodiments of described machines, processes and methods include a drum to receive waste, mixing blades to process waste, a source of air that is rich in reactive oxygen species, an air flow system comprising a heater to circulate air through the drum, and sensors provided in the machine to monitor operating parameters. A control system is configured to control operation of the machine.

11 Claims, 62 Drawing Sheets

(51) Int. Cl.
  B02C 18/00 (2006.01)
  B02C 18/06 (2006.01)
  B02C 23/24 (2006.01)
  B09B 3/40 (2022.01)
  A61L 9/22 (2006.01)
(52) U.S. Cl.
  CPC ............... B02C 23/24 (2013.01); B09B 3/00 (2013.01); B09B 3/40 (2022.01); A61L 9/22 (2013.01)
(58) Field of Classification Search
  CPC ......... B09B 3/40; B09B 2101/70; C05F 9/02; C05F 17/70; B01F 35/751; B01F 35/753; B01F 35/7542; B01F 35/754251
  USPC ....................................................... 422/105
  See application file for complete search history.

(56) References Cited

U.S. PATENT DOCUMENTS

| | | | |
|---|---|---|---|
| 5,948,674 A | 9/1999 | Mankiewicz | |
| 6,471,767 B1 | 10/2002 | Konczak | |
| 6,893,559 B2 | 5/2005 | Kin | |
| 7,211,187 B2 | 5/2007 | Lumbert | |
| 7,883,040 B2 | 2/2011 | Lee et al. | |
| 2014/0234165 A1 | 8/2014 | Glazer et al. | |
| 2015/0218478 A1* | 8/2015 | Wishard | C10L 5/40 44/629 |

FOREIGN PATENT DOCUMENTS

| | | |
|---|---|---|
| CN | 2293781 Y | 10/1998 |
| CN | 102335672 A | 2/2012 |
| CN | 203091399 U | 7/2013 |
| CN | 103464449 A | 12/2013 |
| CN | 104406395 A | 3/2015 |
| CN | 104413346 A | 3/2015 |
| CN | 205878874 U | 1/2017 |
| CN | 107470328 A | 12/2017 |
| CN | 206919591 U | 1/2018 |
| CN | 114620666 A | 6/2022 |
| CN | 217221018 U | 8/2022 |
| GB | 1320571 A | 6/1973 |
| GB | 2535740 A | 8/2016 |
| JP | 2002048322 A | 2/2002 |
| JP | 2003240436 A | 8/2003 |
| JP | 2003284509 A | 10/2003 |
| JP | 2004066095 A | 3/2004 |
| JP | 2004359530 A | 12/2004 |
| JP | 2011240254 A | 12/2011 |
| JP | 2012217964 A | 11/2012 |
| KR | 100915405 B1 | 9/2009 |
| KR | 20110086434 A | 7/2011 |
| KR | 20120076195 A | 7/2012 |
| WO | 0002832 A1 | 1/2000 |
| WO | 2003064004 A1 | 8/2003 |
| WO | 2010056940 A2 | 5/2010 |
| WO | 2012147574 A1 | 11/2012 |

* cited by examiner

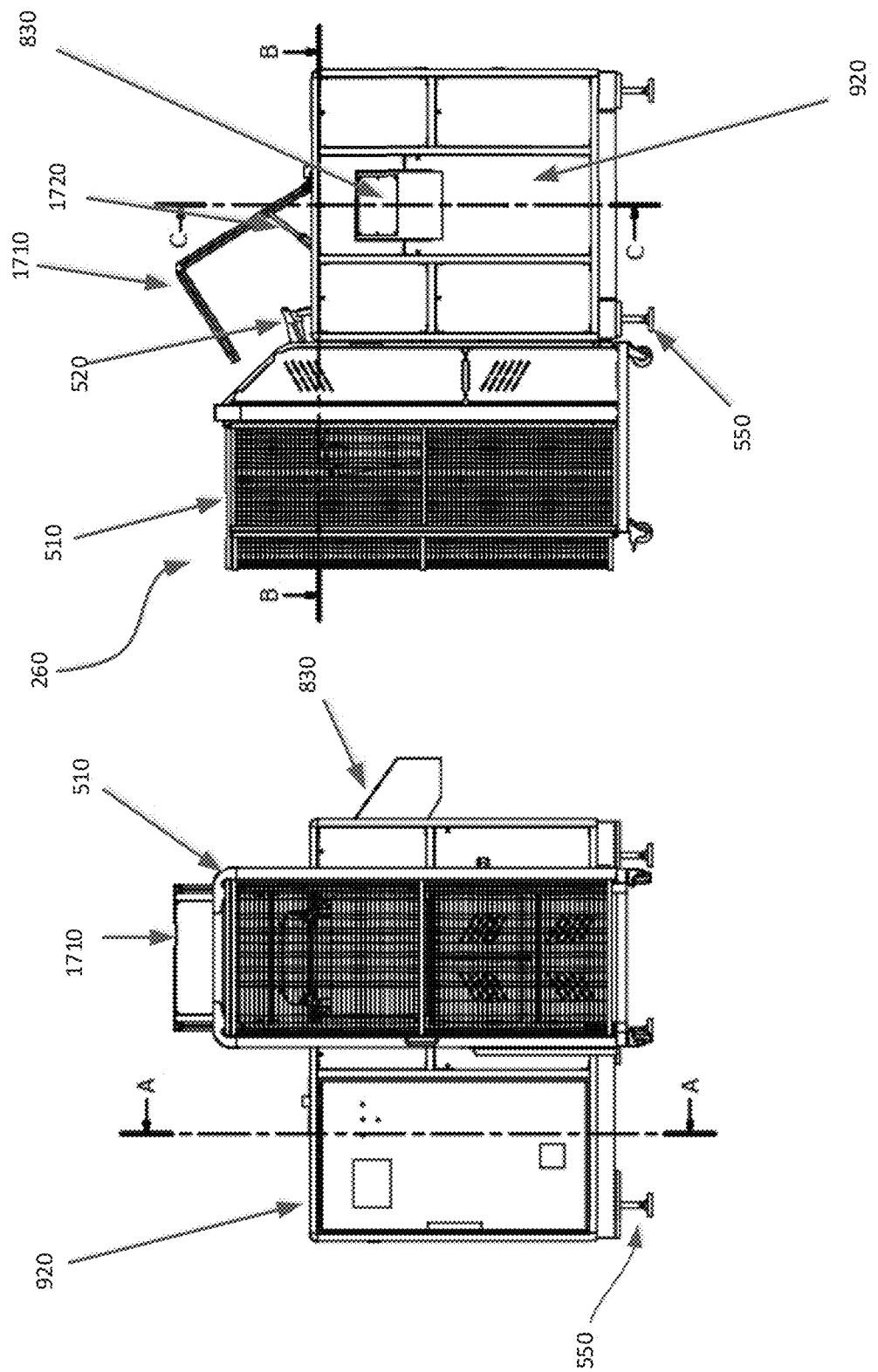

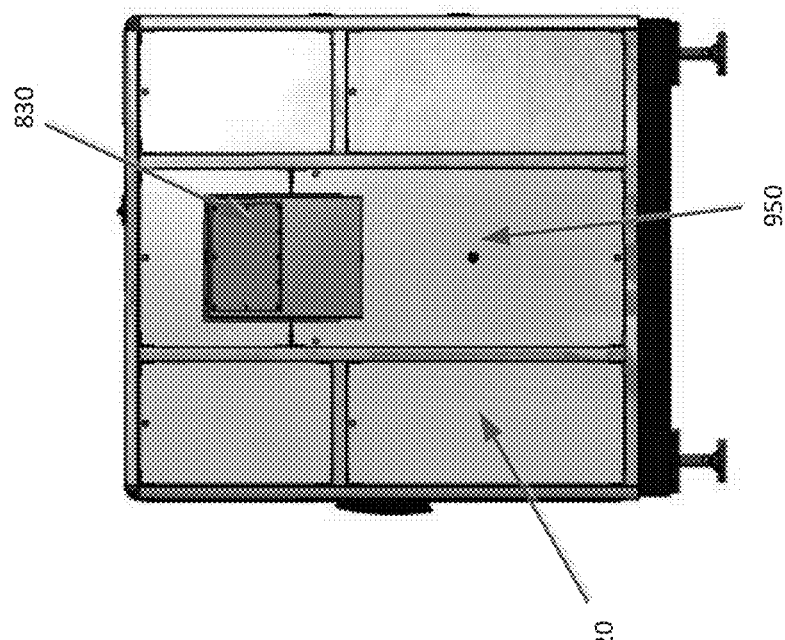
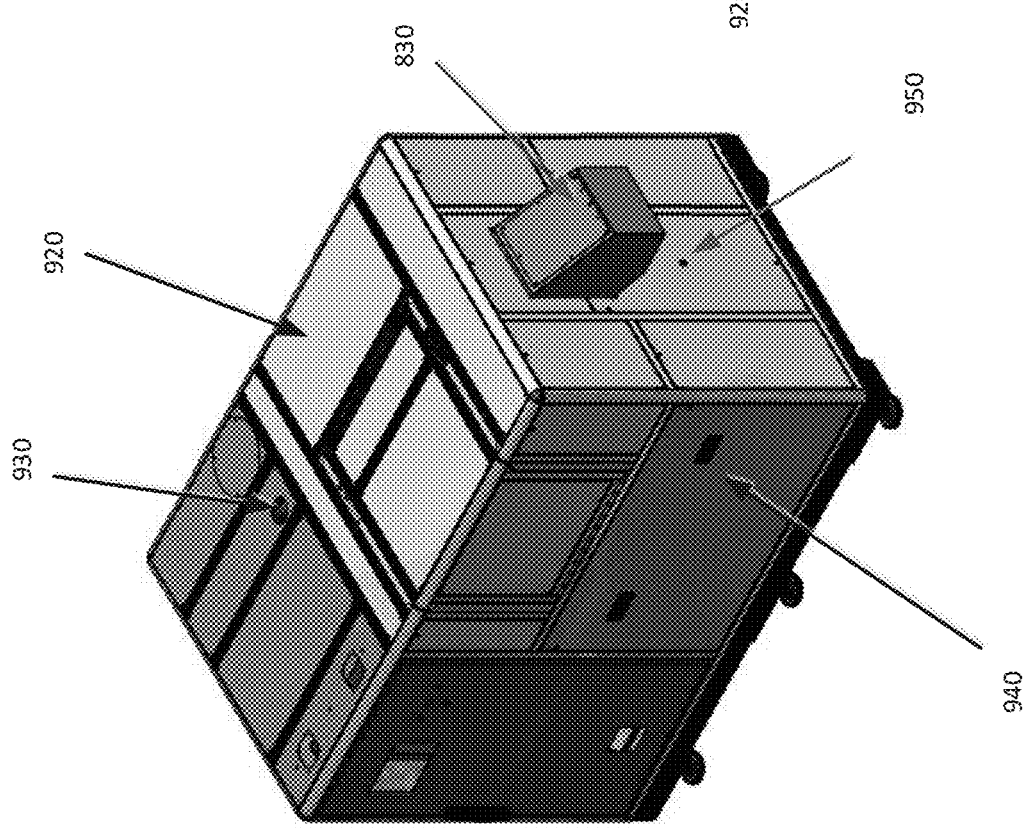

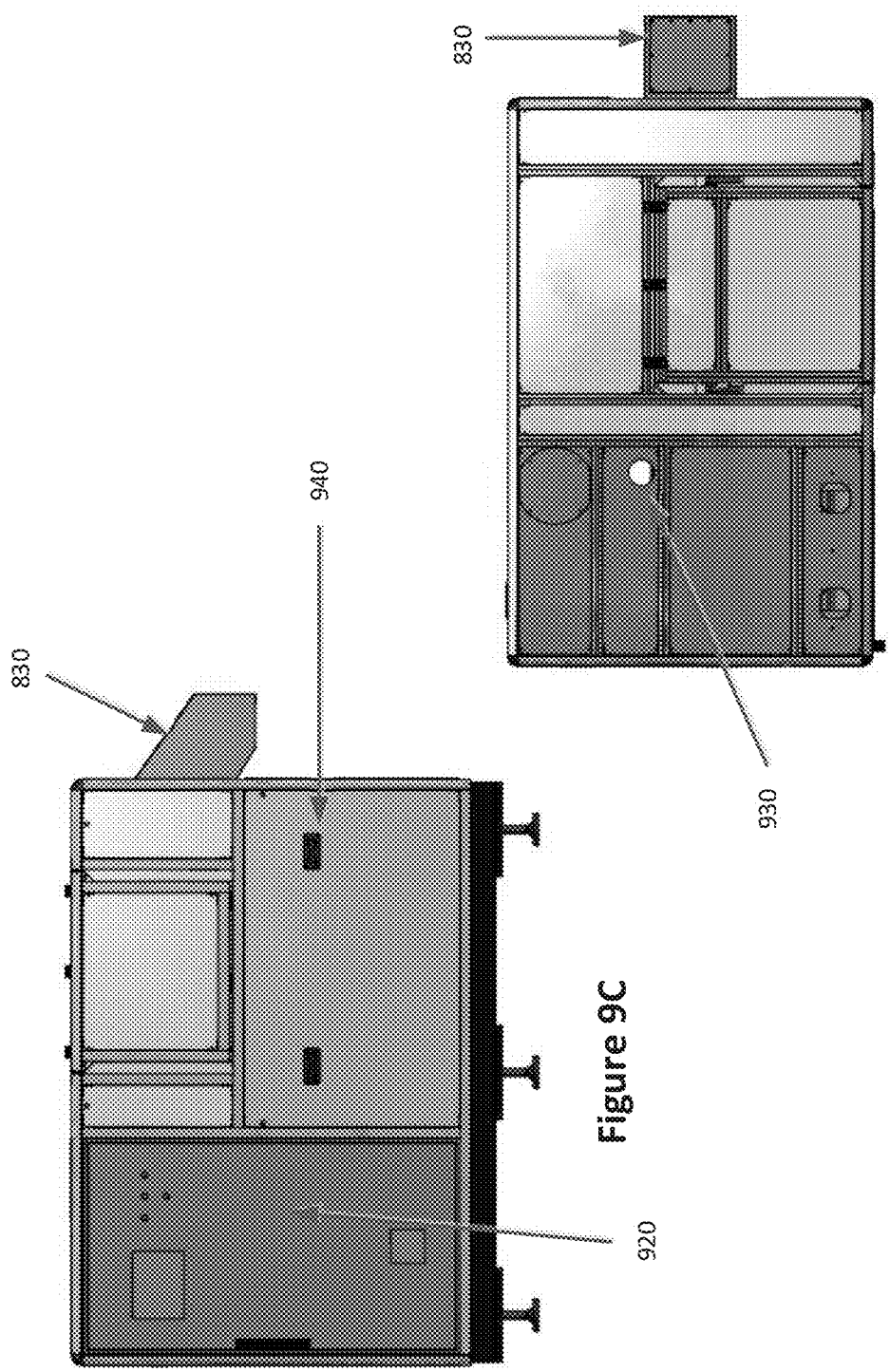

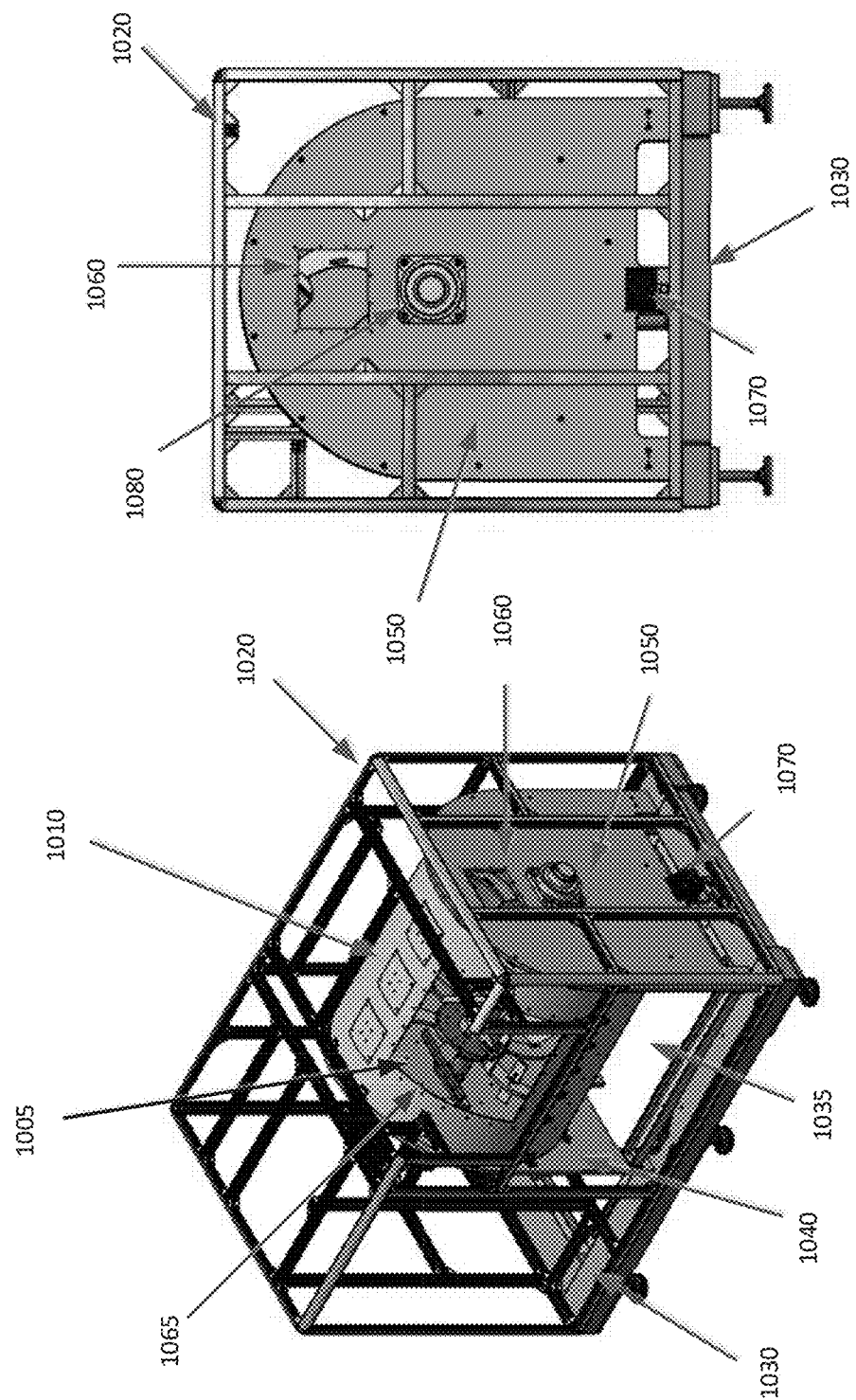

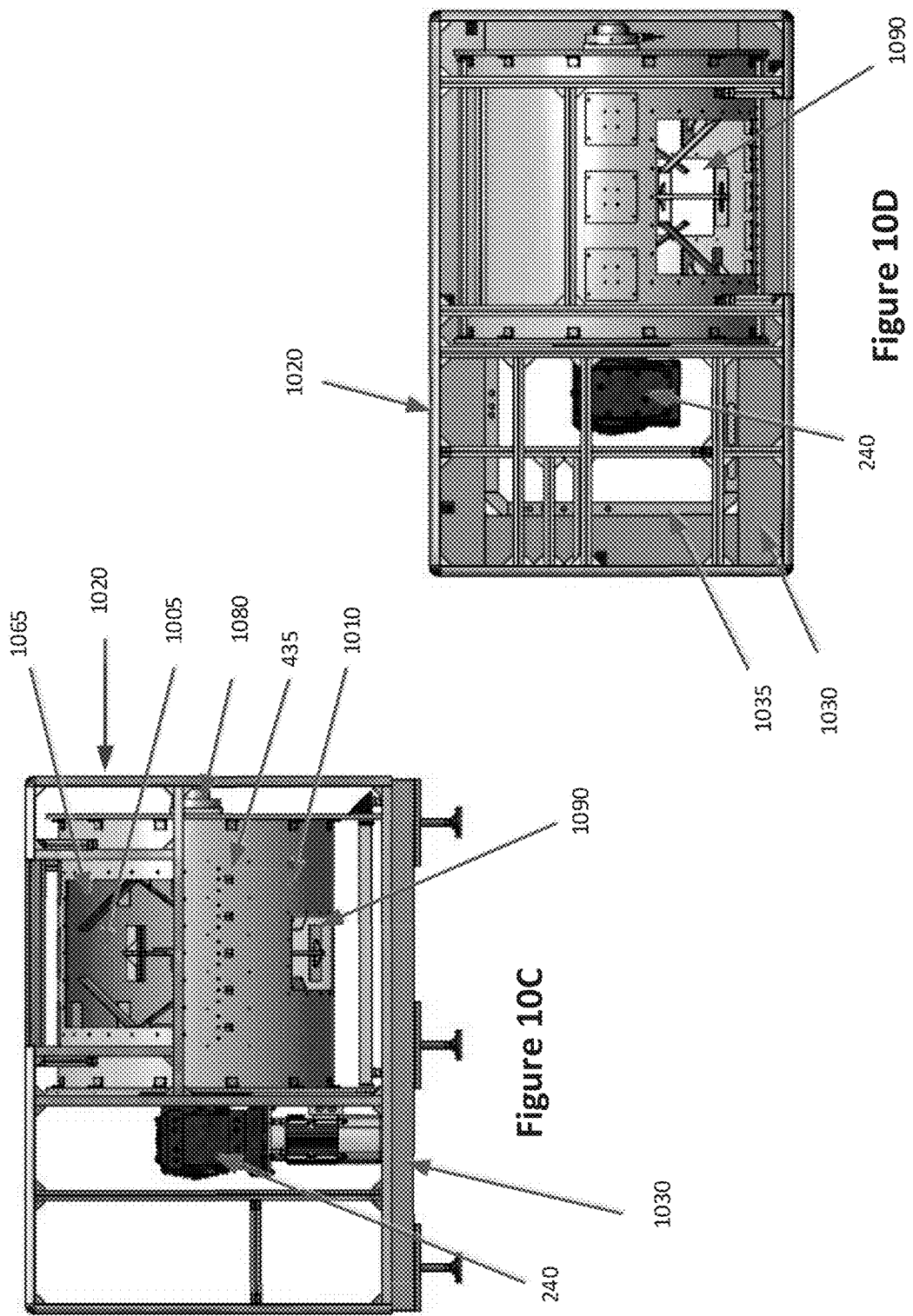

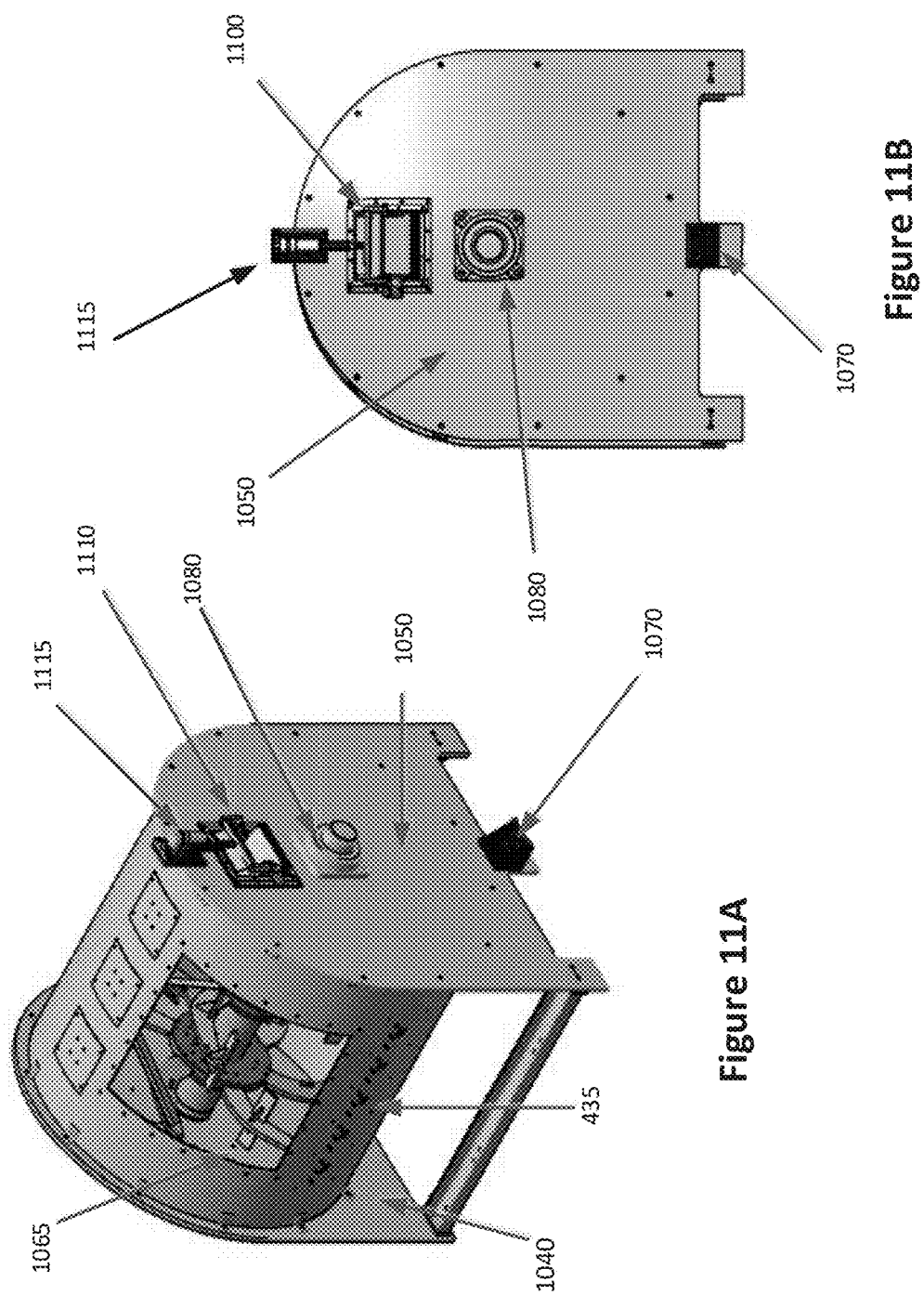

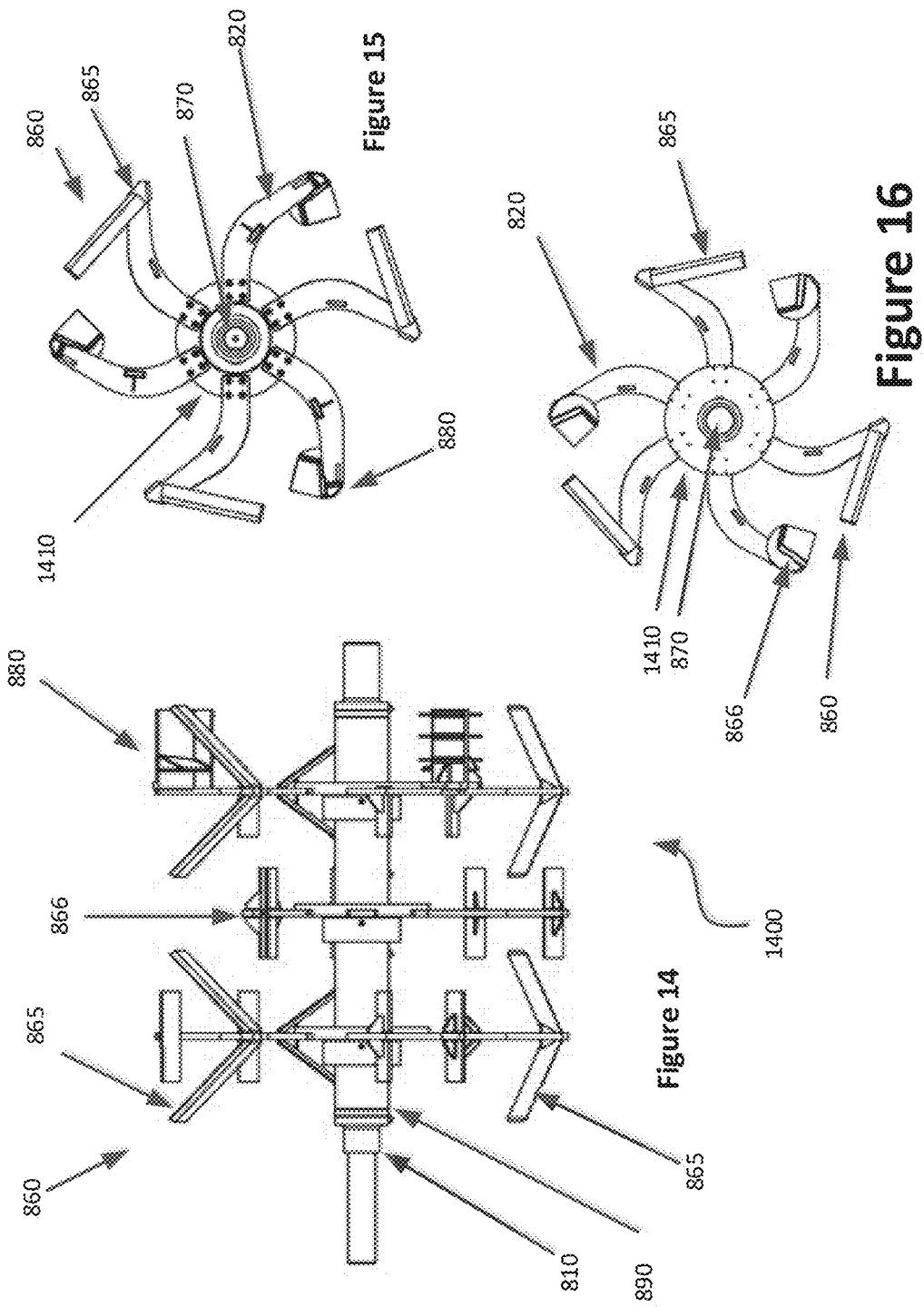

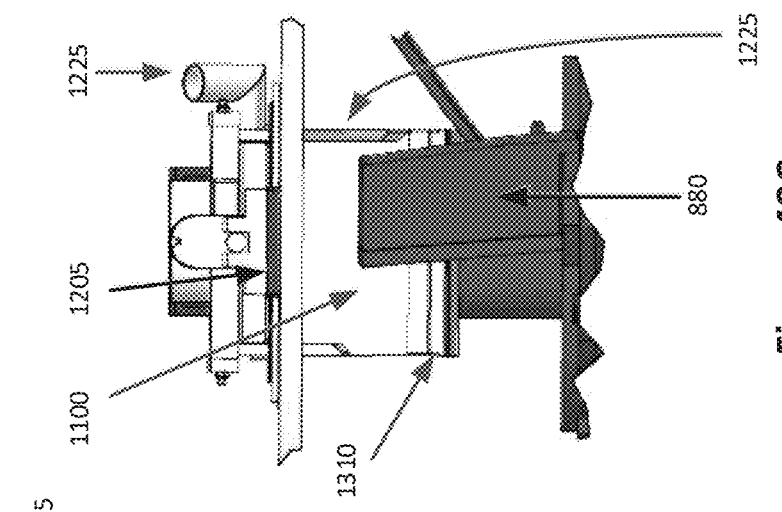
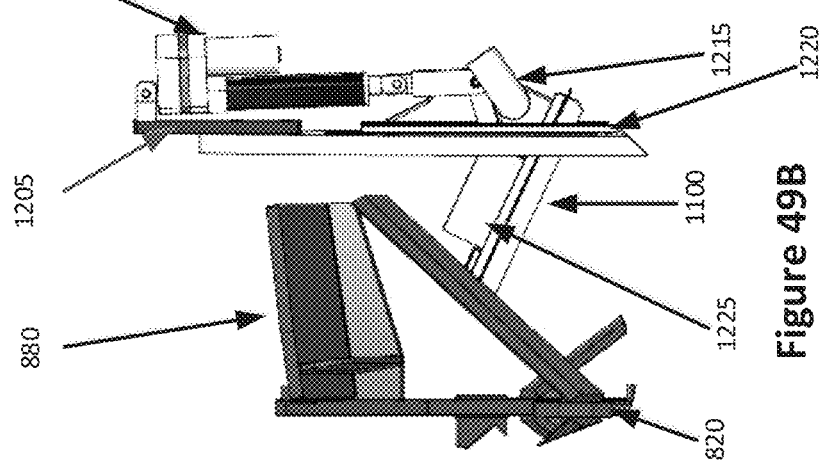
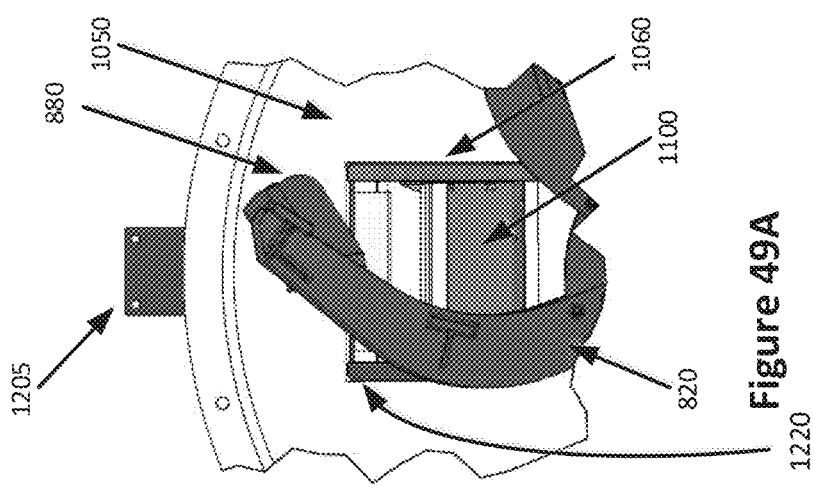
Figure 49C
Figure 49B
Figure 49A

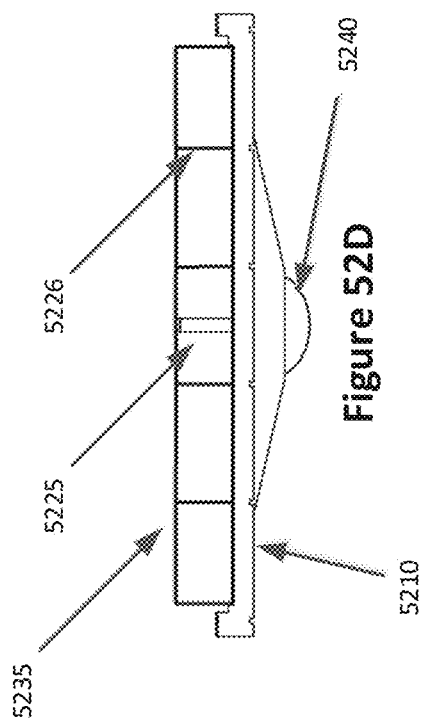
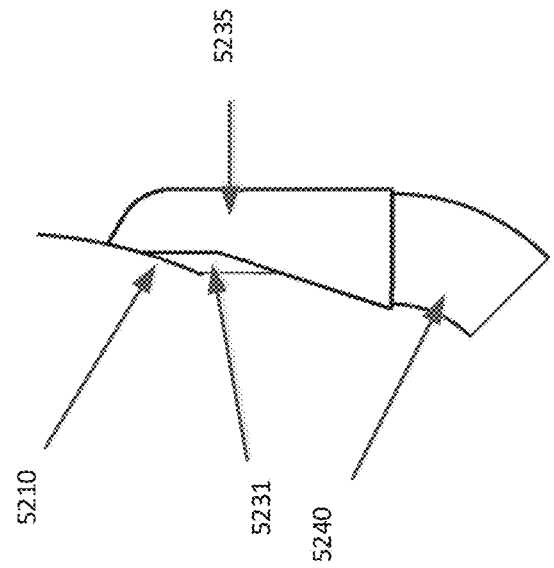
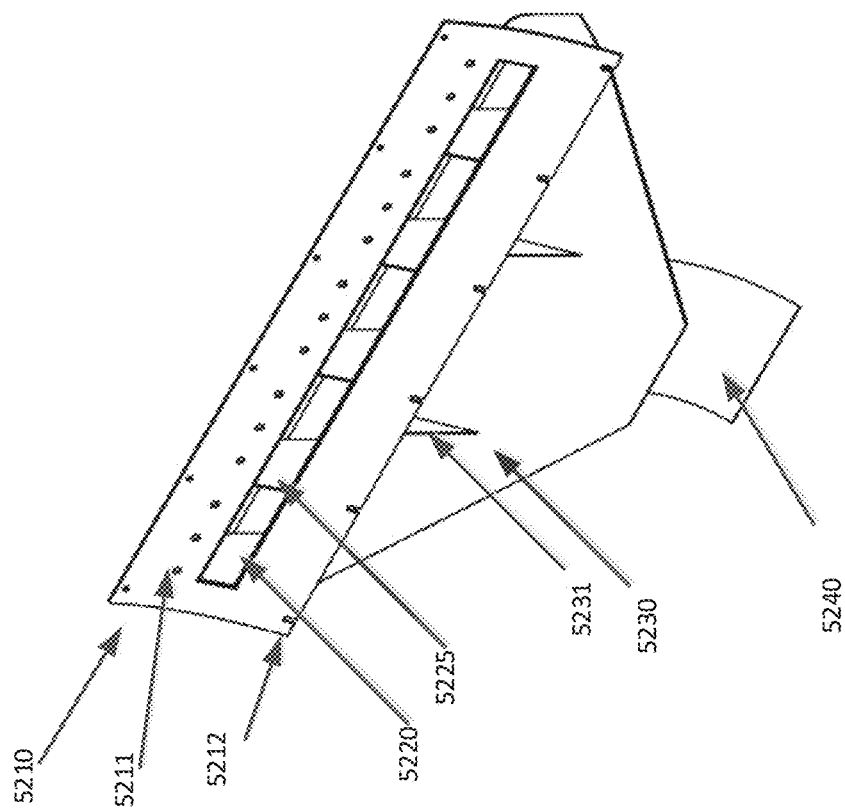
Figure 52D
Figure 52E
Figure 52C

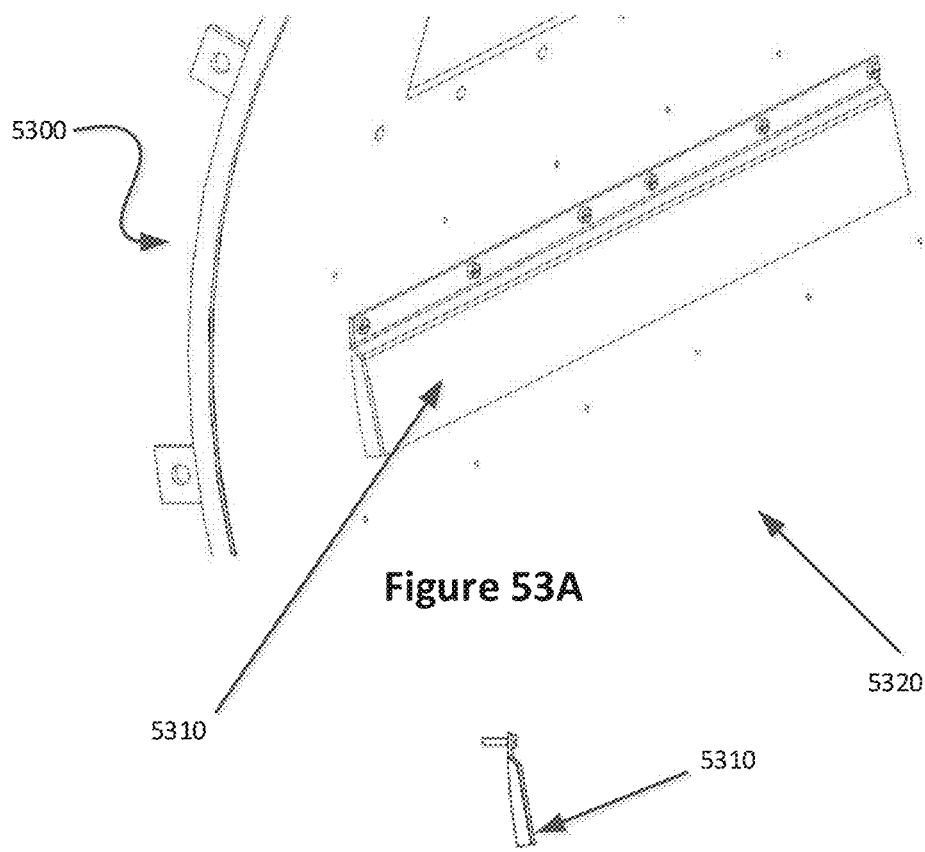
Figure 53A
Figure 53B
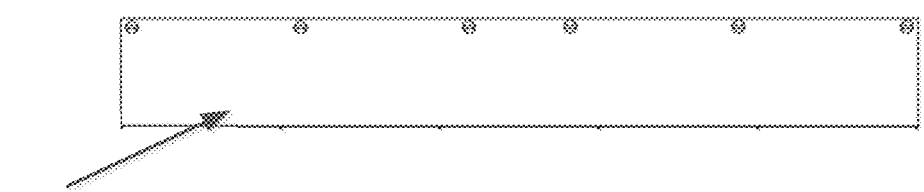
Figure 53C
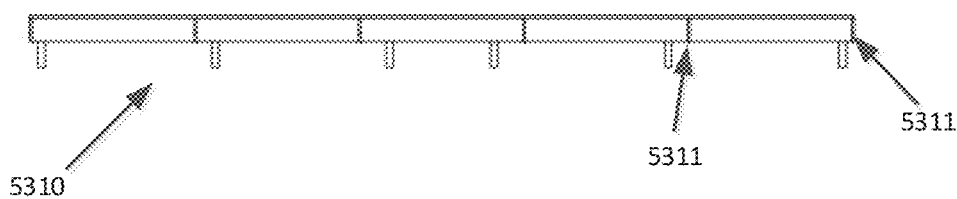
Figure 53D

SYSTEM AND METHOD FOR FOOD WASTE DECOMPOSITION

CROSS REFERENCE TO RELATED APPLICATIONS

The present application is the U.S. national phase of International Application No. PCT/AU2018/050517 filed May 25, 2018, which designated the U.S. and claims priority to and the benefit of Australian Application No. 2018900780, filed Mar. 9, 2018, and the benefit of Australian Application No. 2018901669, filed May 11, 2018, all of which are hereby incorporated by reference in their entirety as if fully set forth below in their entirety and for all applicable purposes.

TECHNICAL FIELD

Embodiments relate generally to systems, methods, machinery and processes related to food waste processing, and in particular to decomposition of such food waste.

BACKGROUND

Food waste is a problem in many areas. Not only is there a cost associated with unused or wasted food, there can be a significant financial or environmental impact associated with such waste. Many hotels, restaurants and supermarkets or produce markets must deal with disposal of food waste on a daily basis. Similarly, food processing facilities such as seafood, poultry or meat processing plants, fruit and vegetable processing facilities may also produce organic animal and/or vegetable waste that must be disposed of. This may involve temporary storage of the waste on or near the premises, which takes up space, can result in unpleasant odours and may attract vermin. Alternatively, the food waste can be transported away from the premises, but this represents an additional business cost and shifts the task of disposal to another party.

Some machines exist that can process food waste. However, some such machines process the food waste by physically breaking down the food waste while heating it in order to "cook" or denature it. Such heating is typically done at high temperatures in excess of 100 degrees Celsius. Such heating requires a lot of energy and the power consumption of such machines can represent a significant cost. Additionally, such machines can take a relatively long time, such as days, to process the food waste into a form that can be disposed of effectively.

It is desired to address or ameliorate one or more shortcomings or disadvantages associated with prior techniques for food waste processing, or to at least provide a useful alternative thereto.

SUMMARY

Some embodiments relate to a machine for food waste processing, comprising:
 a power supply;
 a control system coupled to the power supply;
 a mixing drum defining a mixing chamber and having a volumetric capacity of 2000 litres or less;
 a mixing shaft having mixing blades extending from the mixing shaft, the mixing shaft being configured to rotate to move the mixing blades within the mixing chamber;
 an ioniser coupled to the power supply and arranged to provide a source of air that is rich in reactive oxygen species;
 a heater and a fan coupled to the power supply and arranged to receive the source of air, the heater and fan cooperating to provide a source of heated gas rich in ionised oxygen to the mixing chamber, wherein the heated gas is between about 50 and about 70 degrees C. an/d or wherein the environment in the processing drum is heated to maintain a temperature in the range of 50 to 70 degrees C.;
 a motor arranged to draw power from the power supply and to drive rotation of the mixing shaft;
 wherein the mixing drum defines an input aperture to receive food waste and an outlet to disgorge processed waste residue;
 wherein the control system is configured to operate the motor to drive the mixing shaft for multiple hours while monitoring operating parameters of the machine in order to produce a processed waste residue, optionally wherein the residue comprises or consists essentially of substantially dried and/or inert particulate.

The control system may be configured to monitor the power draw of the motor and to determine a time of peak power draw of the motor.

The control system may be configured to determine that the processed waste residue is ready for disgorgement from the outlet based on one or more process completion conditions.

The one or more completion conditions may include a predetermined time elapsing after the time of peak power draw. The predetermined time may be between about 4 hours and about 7 hours, for example.

The machine may comprise a humidity sensor to sense humidity in the mixing chamber, and wherein the one or more completion conditions include a humidity level in the mixing chamber being below a humidity threshold.

The machine may comprise a temperature sensor to sense air temperature in the mixing chamber or at an exhaust outlet of the mixing drum, and wherein the one or more completion conditions include a sensed temperature level of the temperature sensor being within a predetermined temperature range.

The outlet may be disposed in an outer wall of the drum at a position that is vertically above a position of the mixing shaft.

The mixing shaft may have at least one scoop coupled thereto, the at least one scoop being configured to carry processed waste residue to the position of the outlet.

The control system may be configured to automatically initiate disgorgement of processed waste residue in response to determining that the processed waste residue is ready for disgorgement.

The control system may monitor a weight of the drum during disgorgement to monitor the weight of disgorged residue and to determine the weight of residue remaining in the drum, wherein the control system is configured to cease disgorgement of processed waste residue when the weight of residue remaining in the drum reaches a predetermined minimum threshold level, whereby an amount of at least 20 kg of processed waste residue remains in the drum after disgorgement ceases, optionally at least 50 kg of processed waste residue remains in the drum after disgorgement ceases, optionally at least 100 kg of processed waste residue remains in the drum after disgorgement ceases.

Some embodiments relate to a process for rapid food waste decomposition, comprising:

loading a mass of food waste into a processing chamber defined by a processing drum of a waste processing machine that comprises a shaft and a plurality of blades coupled to the shaft and extending away from the shaft;

rotating the shaft to cause the blades to break down food waste present in the processing drum;

supplying heated air into the processing drum while the shaft is rotating, wherein the environment in the processing drum is heated to a temperature in the range of 50 to 70 degrees C. and/or wherein the heated air is supplied at a temperature of between about 50 to about 70 degrees Celsius, wherein the heated air is rich in radicalised and/or ionised oxygen;

extracting air from the drum to remove airborne moisture from the drum;

monitoring processing conditions relating to the processing drum while the shaft is rotating;

determining that the processing conditions satisfy process completion criteria; and removing residue of the processed food waste from the processing chamber.

The removing may be controlled in order to leave a minimum weight of residue in the processing drum.

The removing may comprise transferring the residue into a hatch in an end wall of the drum.

The minimum weight of residue may be determined as the greater of: a predetermined percentage of the total weight of organic material in the drum at the time of loading the mass of food waste into the processing drum; or a preset minimum weight.

The hatch may be disposed at a level that is vertically above the level of the shaft. The transferring may comprise elevating the residue to the level of the hatch. The transferring may comprise scooping residue into the hatch using at least one of the blades.

The processing conditions may comprise at least one of: power draw of a motor driving the shaft; air temperature inside the processing chamber; humidity of air inside the processing chamber; elapsed time since a time at which the last mass of food waste was loaded into the processing chamber; a current weight of residue in the processing chamber relative to a starting weight of loaded food waste at the time at which the last mass of food waste was loaded into the processing chamber; a percentage weight reduction of the loaded food waste.

The process may further comprise monitoring power draw of a motor driving rotation of the shaft over time to determine a time of peak power draw over a processing period.

The monitoring power draw may comprise setting a beginning of the processing period as the time at which the last mass of food waste was loaded into the processing chamber.

The process further comprise resetting the beginning of the processing period in response to determining that a further mass of food waste has been loaded into the processing chamber.

The process may further comprise monitoring an open or closed status of a loading hatch of the waste processing machine.

The process may further comprise monitoring an output of load sensors coupled to the processing drum to determine a weight of the mass of food waste loaded into the processing chamber.

Removing the residue may comprise continuing to rotate the shaft and discontinuing supplying the heated air.

When the completion criteria are satisfied, the weight of the loaded mass of food waste may be reduced by between about 50% and 90%, optionally by between about 60% and 90%, optionally by between about 70% and 90%.

When the completion criteria are satisfied, the moisture content of the residue may be about 30% or less, optionally between about 30% and about 10%.

Some embodiments relate to a food waste processing system, comprising:

a food waste processing machine comprising a loading hatch, a processing drum and an outlet hatch;

a loader to receive a bin of food waste to be loaded into the food waste processing machine and to manipulate the bin to load the food waste into the processing drum through the loading hatch;

a reader disposed on or adjacent the food waste processing machine or the loader and arranged to read a unique identifier from a machine-readable element on or carried by the bin;

a controller to control operation of the food waste processing machine and the loader and to receive an output of the reader, wherein the controller is configured to determine the unique identifier based on the output of the reader and to transmit the unique identifier to a server to enable tracking of usage of the waste processing machine.

Some embodiments relate to a method of waste processing, comprising:

receiving a batch load of food waste into a processing drum;

operating the processing drum for a period of time and, during the operating, physically breaking down, aerating and warming the food waste, wherein the warming comprises heating an environment in the processing drum to a temperature less than 100 degrees C. and comprises extracting moisture from the environment, and wherein the aerating comprises blowing air that is rich in radicalised and/or ionised oxygen onto the food waste;

determining that processing conditions in the processing drum are satisfied for completion of operation of the processing drum;

removing residue of food waste from the processing drum while leaving at least 50 kg of residue in the processing drum.

Some embodiments relate to a method of waste processing, comprising:

receiving a batch load of food waste into a processing drum;

introducing into the processing drum a quantity of food waste residue from processing of a previous batch load of food waste;

operating the processing drum for a period of time and, during the operating, physically breaking down, aerating and warming the food waste, wherein the warming comprises heating an environment in the processing drum to a temperature less than 100 degrees C. and comprises extracting moisture from the environment, and wherein the aerating comprises blowing air that is rich in radicalised and/or ionised oxygen onto the food waste;

monitoring operation of the processing drum;

determining based on the monitoring that processing conditions in the processing drum are satisfied for completion of operation of the processing drum;

removing residue of food waste from the processing drum.

The removing may be performed while leaving between about 200 kg and about 50 kg of residue in the processing drum. The determining may comprise determining a time of peak power draw of a motor driving rotation of a mixing shaft within the processing drum, and determining that a predetermined time period has elapsed since the time of peak power draw. The predetermined time period may be a selected period in the range of about 4 to 12 hours. The selected period may be in the range of about 4 to 7 hours.

The method may further comprise introducing the removed residue to an anaerobic digester.

The environment in the processing drum may be heated to achieve a target temperature in the processing drum in the range of 50 to 70 degrees C. The target temperature may be about 60 degrees C., for example.

The determining may comprise determining that a predetermined time has elapsed from a time of peak power draw of the processing drum.

Some embodiments relate to a waste processing system comprising a processing drum having an outlet hatch, wherein the outlet hatch is configured, when open, to direct a stream of air along an upper surface of the hatch in order to facilitate egress of processed waste through the hatch.

Some embodiments relate to a waste processing system comprising:
  an outlet hatch at an outlet end of a processing drum, the outlet hatch being positioned above a level of a processing shaft in the drum and having an outlet to direct processed waste passing through the hatch downwardly toward a collection bin; and
  a level sensor positioned to detect a level of waste residue in the collection bin when the collection bin is positioned below the outlet of the outlet hatch.

The system may further comprise a position sensor at or near the outlet end of the processing drum and arranged to detect a presence or absence of the collection bin below the outlet of the outlet hatch.

Some embodiments relate to a waste processing drum, comprising:
  a mixer to rotate within the drum about a horizontal axis;
  a horizontally extending series of apertures in a curved lower side wall of the drum;
  air directors or hoods to direct air passing through the apertures into the drum downwardly along the side wall.

The air directors or hoods have a low profile to avoid projecting into an interior of the drum by more than about 30 mm, optionally about 20 mm.

Some embodiments relate to an organic waste processing machine, comprising:
  a controller;
  a processing drum comprising an agitator;
  a heater;
  a first fan responsive to the controller to force air through the heater and deliver heated air to the processing drum;
  a second fan responsive to the controller to extract air from the processing drum;
  wherein the controller controls the first and second fans to induce a negative pressure in the processing drum relative to an ambient pressure outside the processing drum.

The machine may further comprise an ioniser to generate an air stream rich in ionised oxygen from ambient air, wherein the air forced through the heater by the first fan is the air stream rich in ionised oxygen. The negative pressure may be at least 0.01 mbar.

Some embodiments relate to a method of operation of a waste processing machine, comprising:
  operating a processing drum of the waste processing machine;
  drawing in ambient air through an ioniser to generate a source of air that is rich in ionised oxygen and supplying the source of air that is rich in ionised oxygen into the processing drum;
  determining that processed waste residue is to be offloaded from the processing drum;
  controlling the ioniser to cease generating the source of air that is rich in ionised oxygen;
  diverting ambient air from the ioniser to an air knife adjacent an outlet of the processing drum to assist in offloading waste residue though the outlet.

The air knife may be disposed in a hatch at the outlet of the processing drum. The method may further comprise opening the hatch and transferring waste residue from the processing drum through the hatch into a waste bin disposed below the hatch. The determining may comprise determining a time of peak power draw of a motor driving rotation of a mixing shaft within the processing drum, and determining that a predetermined time period has elapsed since the time of peak power draw. The predetermined time period may be a selected period in the range of about 4 to 12 hours. The selected period may be in the range of about 4 to 7 hours.

Some embodiments relate to a waste processing drum, comprising: a cylindrical wall and first and second opposed end walls to define a substantially closed cylindrical processing chamber except for a waste ingress opening, at least one laterally extending air inlet aperture positioned lower than the waste ingress opening and at least one laterally extending air inlet aperture positioned lower than the waste ingress opening and at least one laterally extending air exhaust aperture positioned higher than the waste ingress opening.

The at least one exhaust aperture may comprise multiple exhaust apertures that span a length of between 60-95% of the lateral length of the drum. The at least one air inlet aperture may comprise multiple air inlet apertures that span a length of between 50-80% or 60-90% of the lateral length of the drum.

Some embodiments relate to an organic waste processing machine comprising the waste processing drum described above.

BRIEF DESCRIPTION OF DRAWINGS

FIG. 5A is front elevation view of a waste processing machine comprising a waste loader system according to some embodiments;

FIG. 5B is side elevation view of a waste processing machine comprising the waste loader system;

FIG. 9A is a perspective view of a waste processing machine according to some embodiments, shown without the waste loader system;

FIG. 9B is a side view of a waste processing machine of FIG. 9A;

FIG. 9C is a front view of a waste processing machine of FIG. 9A;

FIG. 9D is a top view of a waste processing machine of FIG. 9A;

FIG. 10A is perspective view of a partial interior of the waste processing machine of FIG. 9A;

FIG. 10B is side view of a partial interior of the waste processing machine of FIG. 9A;

FIG. 10C is front view of a partial interior of the waste processing machine of FIG. 9A;

FIG. 10D is top view of a partial interior of the waste processing machine of FIG. 9A;

FIG. 11A is a perspective view of a waste processing machine drum of the waste processing machine of FIG. 9A;

FIG. 11B is a side view of a waste processing machine drum of the waste processing machine of FIG. 9A;

FIG. 14 is a front view of a waste processing mixer;

FIG. 15 is a first end view of the waste processing mixer of FIG. 14;

FIG. 16 is a second (opposite) end view of the waste processing mixer of FIG. 14;

FIG. 49A is a partial view from inside the processing chamber of an outlet hatch in an open position and with a residue scoop in a depositing position;

FIG. 49B is a side view from inside the processing chamber of the outlet hatch in an open position and with the residue scoop in a depositing position;

FIG. 49C is a top view from inside the processing chamber of the outlet hatch in an open position and with the residue scoop in a depositing position;

FIG. 52C is a perspective view of an air inlet plenum;

FIG. 52D is a top sectional view of an air inlet plenum;

FIG. 52E is a side view of an air inlet plenum;

FIG. 53A is a perspective view of an air inlet shield within a waste processing chamber;

FIG. 53B is a side view of an air inlet shield;

FIG. 53C is a front view of an air inlet shield;

FIG. 53D is a top view of an air inlet shield;

DETAILED DESCRIPTION

Embodiments relate generally to systems, methods, machinery and processes related to food waste processing, and in particular to decomposition of such food waste. Specific embodiments employ a mixing element, such as a shaft comprising multiple mixing or processing blades projecting therefrom, that rotates within a processing chamber within which the food waste is deposited. Such embodiments break down the food waste over time by the mechanical action of the mixing element in combination with a source of heated air. The heated air is heated to have a temperature of around 50 to 70 degrees C., in some embodiments. Such heated air is rich in ionised oxygen, such as radicalised oxygen, for example.

Embodiments also relate to food waste processing systems that allow usage tracking of a waste processing machine. Such embodiments include a reader disposed on or adjacent the food waste processing machine or a waste loader and arranged to read a unique identifier of a machine-readable element on or carried by a waste loading bin used to load waste into the waste processing machine.

Waste processing machines described herein are suited for organic (including food) waste processing on-site with the source of the waste. For example, such machines can be located in a hotel premises, near a food court or at a chicken farm, fishery or abattoir premises, for example, so that there is no immediate need to transport the organic waste to another site for disposal. Waste processing machines described herein are configured to process the waste over a time less than 24 hours to reduce the weight and volume of the waste and produce a waste residue that is relatively dry and easy to dispose of. The volume may be reduced by at least 50 to 60% and up to about 80% of the original volume of the organic material loaded into the machine, for example. The resultant residue is free of noxious or string odours and can be stored for long periods of time in dry environments without rotting.

Described embodiments can help to: reduce costs associated with food and waste management; reduce contributions to greenhouse gas emissions; improve site cleanliness and safety through the removal or avoidance of rotting waste, which can attract vermin and insects; reduce odours associated with food and organic waste storage; and reduce the quantity of collection bins required on site.

Figure 1:
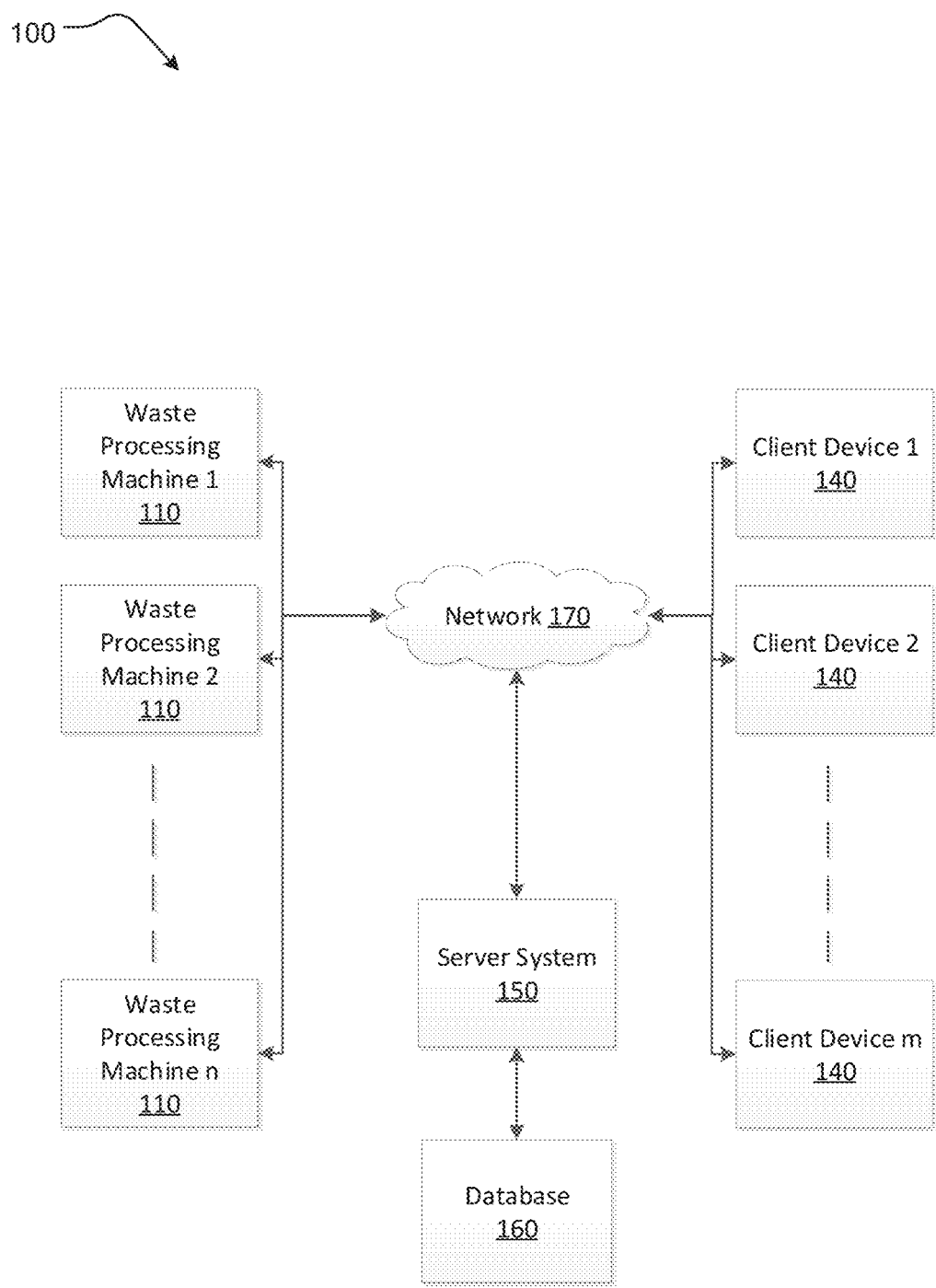
FIG. 1 is a block diagram of a distributed waste processing system comprising one or more waste processing machines according to some embodiments.

FIG. 1 is a block diagram of a distributed waste processing system 100. The distributed waste processing system 100 includes a series of waste processing machines 110 in communication over a network 170. Network 170 may include public and/or private data communication networks or subnetworks, including wired and wireless networks or subnetworks, for example. The network 170 communicates with a server system 150 and a database 160. Data from the waste processing machines 110 may be sent to the server system 150 over the network 170 to be stored on the database 160. One or more client computing devices 140 may access the database 160 and server system 150 through the network 170 to retrieve information stored by the waste processing machines 110. This stored information in database 160 may include service logs, performance statistics, real time sensor data, or other operational information sent by the waste processing machines 110, for example.

The client devices 140 may also send instructions to the waste processing machines 110 via the network 170 to start or stop waste processing machine processes, specify threshold values, control operational parameters or control other functions of the waste processing machines 110, for example. For this purpose, the one or more client devices 140 may store and execute application software configured to display operational information of one or more of the waste processing machines 110 and to facilitate interaction of a supervisor with one or more of the waste processing machines 110.

Figure 2:
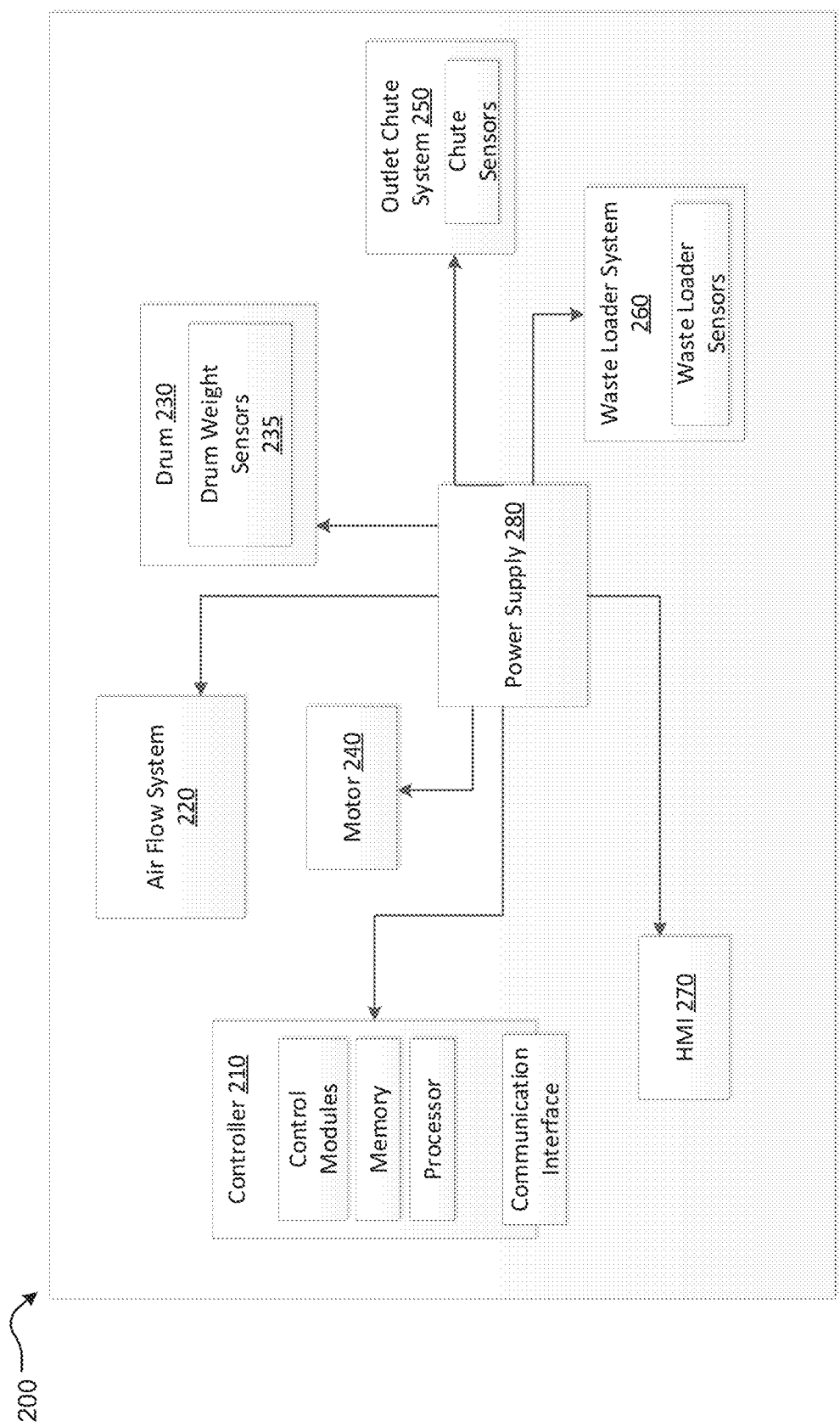
FIG. 2 is a block diagram of a power supply arrangement of a waste processing machine according to some embodiments.

Embodiments of the waste processing machines 110 are now described in further detail, with reference to various drawings. For example, FIG. 2 is a block diagram of power-consuming components 200 of a waste processing machine 110, illustrating a power-supply configuration for the waste processing machine 110. Generally, the power-consuming components 200 all draw power from a power supply 280 in the waste processing machine 110. Power supply 280 draws on an external 3-phase AC power supply, such as 240V or 110V mains power, for example.

Power is supplied by power supply 280 through standard insulated electrical cabling throughout the waste processing machine 110, sufficient to resist operating temperatures of the waste processing machine 110. In some embodiments, the power supply 280 may be supplemented or configured to run from generators, power storage devices such as batteries, solar panels, or other suitable electrical power supply means. In some embodiments, power may be supplied directly from the power supply 280 to certain ones of the system components 200. In other embodiments, a power hub or bus 330 may be supplied. In some embodiments, power is supplied to smaller components, such as drum or chute sensors, through a hub or bus 330 in communication with the controller 210.

Each waste processing machine comprises a controller 210, an air flow system 220, a waste processing drum 230 with drum weight sensors 235, a motor 240 to drive a mixing shaft in the drum 230, an outlet chute system 250, a waste loader system 260 and a human-machine interface (HMI) 270. The controller 210 generally controls operation of or receives output signals from the other power-consuming components 200 of the waste processing machine 110. The controller 210 directly or indirectly controls supply of power to the power-consuming components 200 from the power supply 280.

Figure 3:
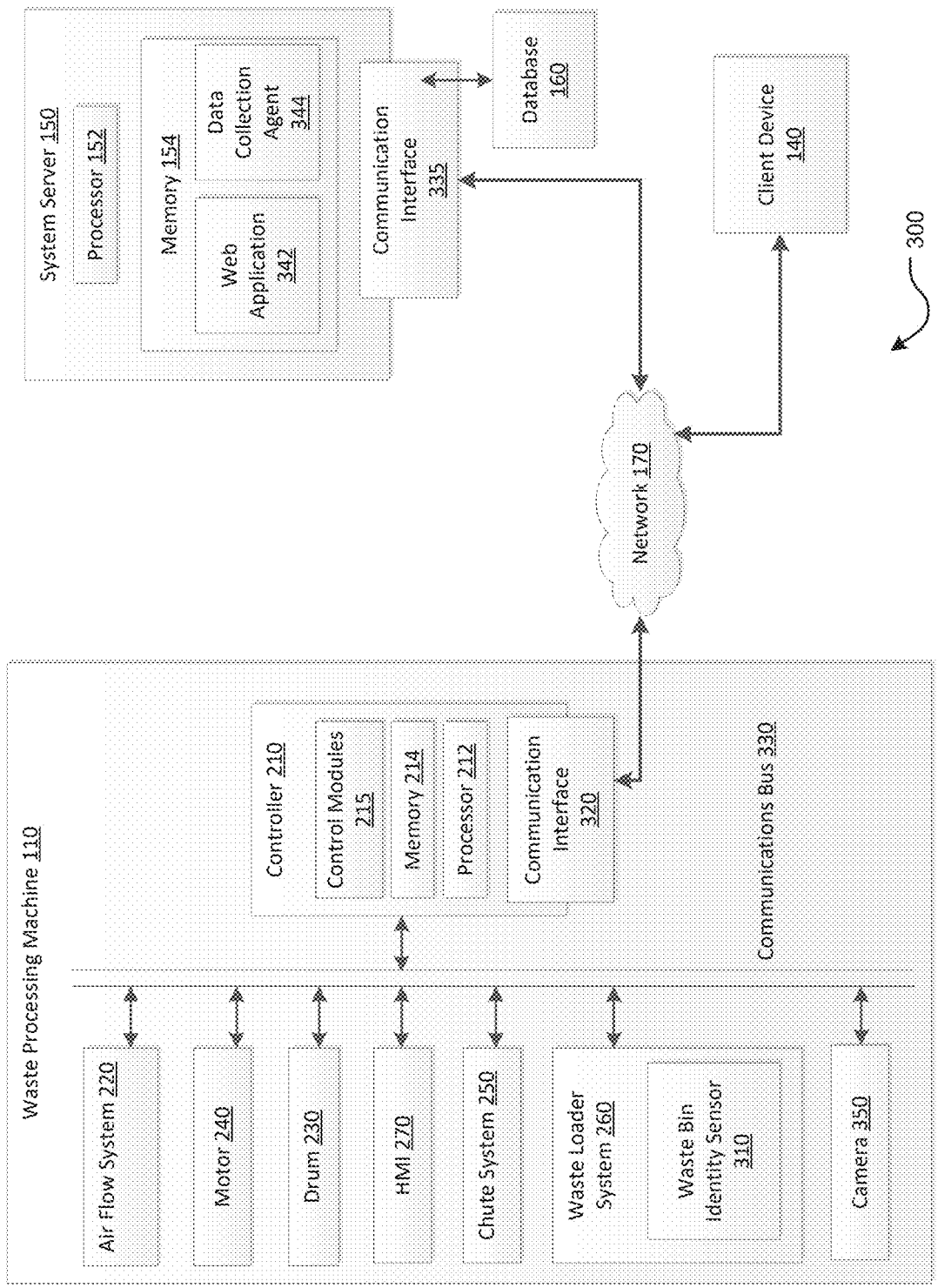
FIG. 3 is a block diagram of a control and communication arrangement of a waste processing machine according to some embodiments.

FIG. 3 is a block diagram illustrating data or signal communication and/or control between computing and sensor components 300 of the distributed waste processing system 100. Controller 210 may be or comprise a computing device on board the waste processing machine 110 that communicates with the various components within the waste processing machine 110 to receive information and pass instructions. The controller 210 comprises at least one computer processor 212 and memory 214 (storing program instructions executable by the processor 212) that in combination allow the execution of one or more control modules 215 by the controller 210 to exert operational monitoring and control of the operation of the waste processing machine 110.

In some embodiments, controller 210 may be implemented using a suitable programmable logic controller, such as a Siemens™ SIMATIC S7-1200. The HMI 270 provides an interface for an onsite operator to access the data stored on-board the controller 210 and input control instructions via the controller 210 for exerting operational control over one or more operations of the waste processing machine. In some embodiments, the HMI 270 may be implemented using a Weintek™ MT8090XE HMI, for example.

The controller 210 also communicates with the server system 150 through a network 170. Although FIG. 3 illustrates a particular arrangement of the waste processing machine 110, system server 150, client device 140, and network 170, this disclosure contemplates any suitable arrangement of waste processing machine 110, system server 150, client device 140, and network 170. As an example and not by way of limitation, one or more of client devices 140, system server 150, and waste processing machine 110 may be connected to each other directly, bypassing network 170. As another example, controller 110 and system server 150 may be physically or logically co-located with each other in whole or in part.

Figure 34A:
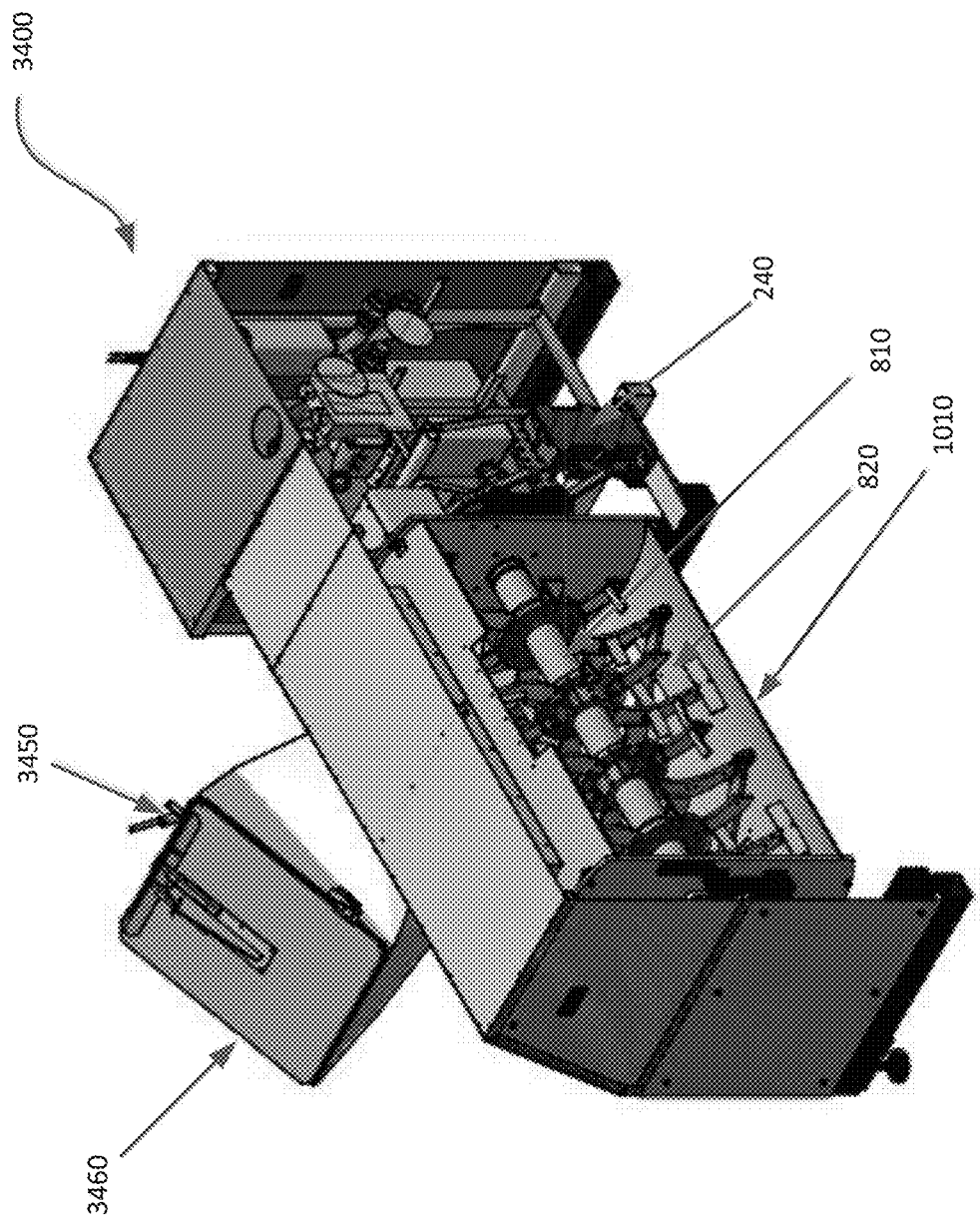
FIG. 34A is a rear perspective sectional view of a waste processing machine according to some alternative embodiments.
Figure 34B:
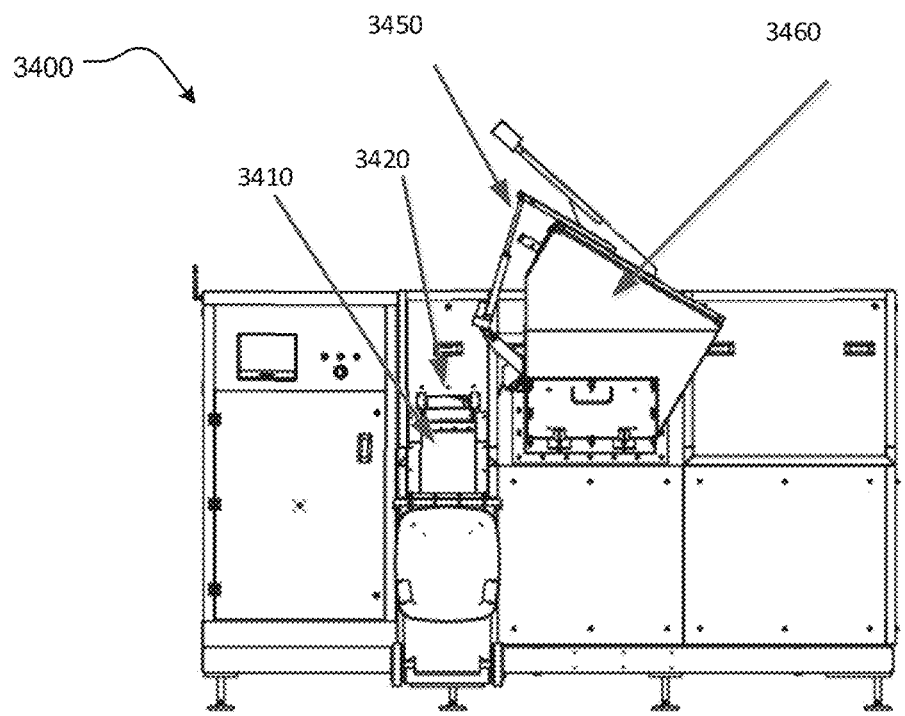
FIG. 34B is a front view of the waste processing machine of FIG. 34A.
Figure 34C:
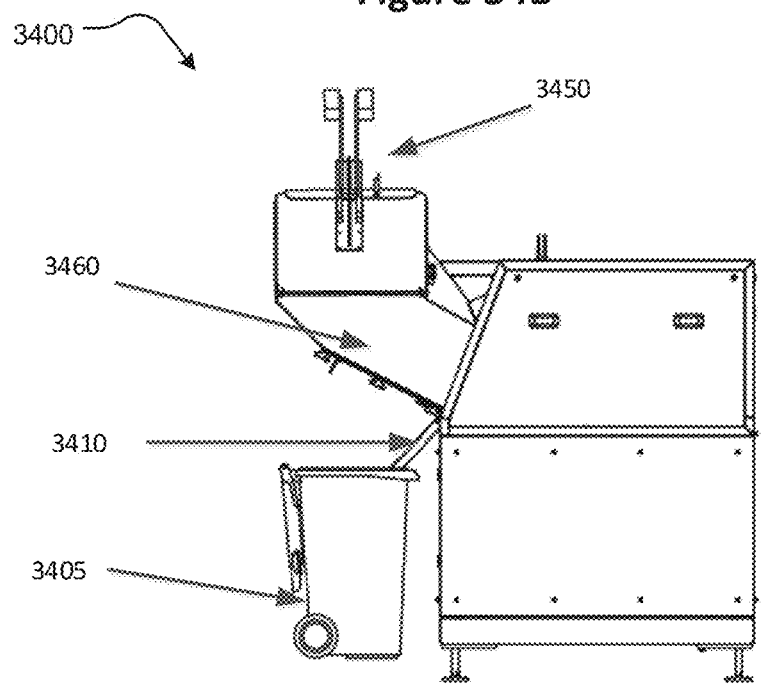
FIG. 34C is a side view of the waste processing machine of FIG. 34A.
Figure 34D:
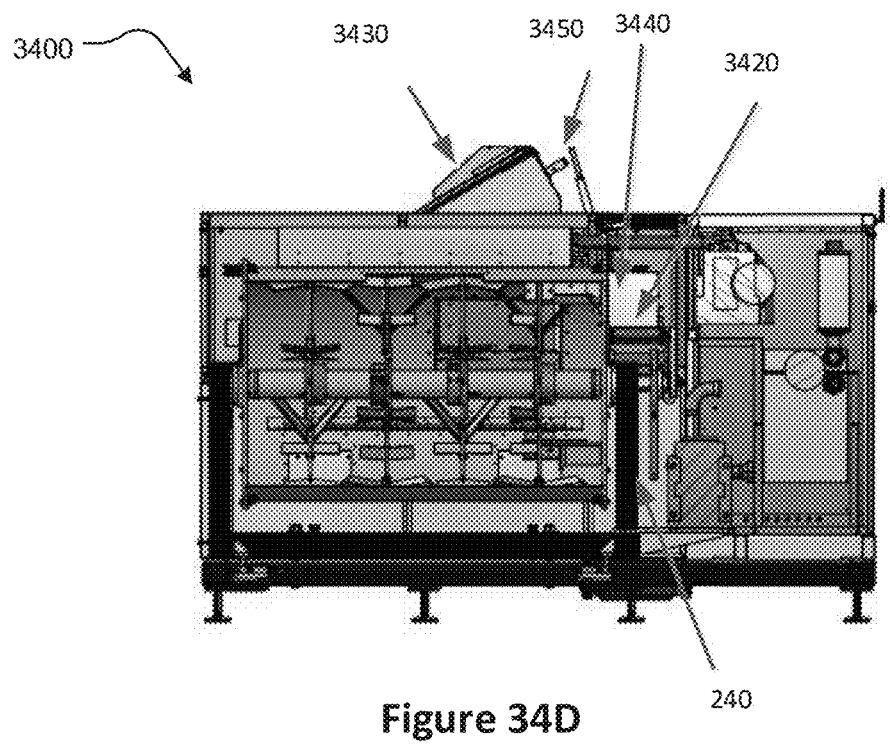
FIG. 34D is a front sectional view of the waste processing machine of FIG. 34A.
Figure 34E:
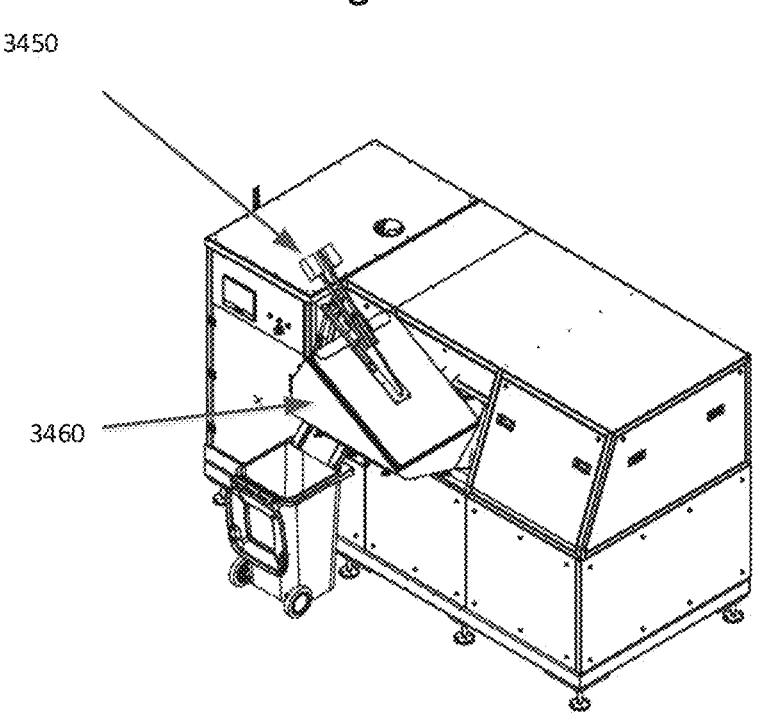
FIG. 34E is a front perspective view of the waste processing machine of FIG. 34A.

The server system 150 comprises at least one computer processor 152 and memory 154 (local and/or remote from processor 152) that stores executable program instructions for execution by processor 152. The executable program instructions stored in memory 154, when execute, function as software modules implementing a web application 342 and data collection agents 344. The web application provides 342 provides dashboards to display and report on status information of one or more waste processing machines 110 in the distributed waste processing system 100. The web application 342 also allows an administrator to remotely administer waste processing machines 110 by passing on commands from an administrator to the controller 210 of a specific waste processing machine 110. The instructions may include instructions to stop in an emergency, instructions to offload processed waste or instructions to load a positioned waste bin 3405 (FIG. 34C), for example. Most of the operations of individual waste processing machines 110 may be automated so as to allow the distributed waste processing system 100 to function as autonomously as possible. Controls through the system server 150 may be used for proactive monitoring or for responding to unexpected machine conditions. The web application 342 may be implemented using an ASP.NET web application framework, for example.

Controller 210 comprises or cooperates with a communication interface 320 that allows the controller 210 to pass information to and receive information from the Network 170. In some embodiments, the communication interface 320 may be implemented using a 3G cellular router and a fixed public IP SIM card, for example. In other embodiments, the communication interface 320 may be implemented using a wired router connected to a wide area network. The system server 150 also comprises a communication interface 335 that may be implemented in some embodiments using a wired router in connection with a wide area network. Both the communication interfaces 320 and 335 may be implemented using other suitable alternative wired or wireless technologies.

Within the waste processing machine 110, a communication bus 330 may be implemented to allow the transfer of data and commands between the various components of the waste processing machine 110 and the controller 210. In some embodiments, some components of the waste processing machine 110 may communicate wirelessly with the controller 210 and may not rely on the communication bus 330 to receive or transmit signals.

Voltage inverters may be installed in the waste processing machine 110, to supply a specifically required AC voltage to system components. Such components may include the motor 240, the intake fan 420, and the exhaust fan 450. The voltage inverters may be configurable to cater for different energy requirements, with different configurations available with an interface on the voltage inverter, or remotely over a network 170. The voltage inverters may comprise variable-frequency drives or low voltage converters.

In some embodiments, three separate voltage inverters are installed within the waste processing machine 110. In such embodiments, each voltage inverter provides a separately regulated power to one of the motor 240, the intake fan 420, and the exhaust fan 450; allowing each particular motor's power requirement to be separately controlled to meet their individual ratings, and for ease of maintenance.

In some embodiments, the voltage inverters may comprise Siemens™ SINAMICS V20 Basic converters.

In some embodiments, the waste processing machine 110 may also include a camera 350 mounted within the drum 230 or near the inlet aperture (i.e. loading hatch) of the drum 230 to provide images of waste being loaded and/or processed. Images captured by the camera 350 may be transmitted by the controller 210 to the system server 150 for storage in database 160. A client device 140 may access the images stored in database 160 via the system server 150.

The system server 150 is also configured to communicate with a database 160. The database 160 may be implemented on or accessed through a separate server or the same server as system server 150. The database 160 may be used to store sensor data generated by all the waste processing machines 110 that are a part of the distributed waste processing system 100. The software modules implementing the data collection agent 344 may mediate the collection of sensor data from various waste processing machines 110 and then store the received data to the database 160. In some embodiments, processes implementing the data collection agent 344 may poll each waste processing machine 110 every 3 seconds over a Modbus UDP protocol to query all the relevant sensor and other data generated by each waste processing machine 110, for example. In some embodiments, processes implementing the data collection agent 344 may poll each waste processing machine 110 every 15 minutes via an FTP protocol, for example. The data collection agent 344 may segment its queries over more than one polling cycle to maintain latency of collected data without generating communication bottlenecks over the network 160. For example, data-intensive but low-priority queries could be undertaken at a lower frequency cycle such as one query every 15 minutes, for example. On the other hand, data-light but high-priority queries could be undertaken at a higher frequency, such as one query every 3 seconds, for example.

The data stored in the database 160 may be retrieved and accessed through the web application 342. In some embodiments, the system server 150 may be implemented using a Windows™ operating system, for example. In some embodiments, the database 160 may be implemented using a Microsoft™ SQL Server, for example. Other suitable operating systems and database implementations may be used instead.

Motor: The motor 240 may comprise an electric DC motor providing sufficient torque to rotate the waste processing mixer 1400 when loaded with a maximum waste load (e.g. 500-600 kg for a 1000 litre drum), at a configurable (selected) rotation speed. In some embodiments, the rotation speed of the mixer 1400 is selected to rotate the waste processing mixer 1400 at about 5 RPM. This rotation speed is selected to provide a relatively high level or rate of effective waste decomposition for relatively minimum or lower power draw by the motor 240. In other embodiments, another speed, such as 10 RPM may be selected. The rotation speed of the mixer 1400 may be selected to maximize energy efficiency, processing efficiency, or both. The rotation speed of the mixer 1400 may be selectively varied throughout the course of processing a waste load.

In some embodiments, the motor 240 may comprise a belt drive motor, or electric AC motor, such as a direct drive motor.

Air flow system: The air flow system 220 supplies heated and ionised air into the drum 230, and exhausts spent ionised oxygen and decomposition fumes out of the machine. The air flow system 220 may comprise an air intake side having an intake air filter 410, ioniser 415, intake fan 420, valve 425, air heater 430, and an exhaust side which may comprise an exhaust air filter 445 and exhaust fan 450. The drum 230 receives low-humidity, heated and ionised air from the intake side and exhausts air from the exhaust side. The exhaust air typically has higher humidity than the air received at the drum 230 at the intake side because of the moisture entering the air from the food waste as it is processed in the drum 230.

The air flow system components are connected through air conduit sections 610. The air conduit sections 610 may be comprised of aluminium, plastic, PVC, stainless steel, or other suitable materials.

In some embodiments, pressure sensors form part of the air flow system 220, positioned within the drum 230, sending pressure data to the controller 210. Expected pressure ranges may be between −3 to +3 mbar, with an ideal pressure within the drum 230 being slightly negative, for example at least around −0.01 mbar relative to an external environment of the processing drum. A sufficiently negative pressure may ensure optimal airflow from the internal chamber 1005 into the exhausting system, rather than airflow into the environment through the inlet aperture 1065.

Intake Air Filter: The intake air filter 410 may comprise a conical air filter of a suitable type to ensure pollution or contaminants from environmental air are filtered prior to being drawn in to the system. The intake air filter 410 is coupled directly to the intake of the ioniser. The intake air filter 410 is easily accessed through outer housing panels of the waste processing machine 110, allowing maintenance or replacement of the intake air filter 410. This configuration also ensures the intake air filter 410 receives a minimal exposure to contaminants and unfiltered air, which may impede the ionisation process and operation of the ioniser 415. In some embodiments, the intake air filter 410 may be a flat panel air filter or cylindrical air filter. In some embodiments, the intake air filter 410 may be contained within a filter housing, with defined inlet portions, allowing air flow to be directed across the filter in an optimal filtering direction.

Exhaust Air Filter: The exhaust air filter 445 may comprise a conical air filter sufficient to filter waste particulate from the air within the chamber 1005, to minimise or prevent airborne waste particulate from being dispersed into the atmosphere. The exhaust air filter 445 may be contained within a filter housing arranged to provide easy maintenance access, allowing easy filter replacement. The filter housing may be constructed from aluminium, PVC, stainless steel, or other suitable materials, for example. In some embodiments, the intake air filter 410 may be a flat panel air filter or cylindrical air filter. In some embodiments, the exhaust air filter housing has defined inlet portions, allowing air flow to be directed across the filter in an optimal filtering direction.

Ioniser: The ioniser 415 ionises and/or radicalises oxygen in the air stream and provides air rich in reactive oxygen species to the processing chamber 1005 of drum 230 through the air flow system 220. The ioniser 415 may be a low energy plasma device, utilising a mixed ion reactive approach to generate variety of reactive oxygen species. The addition of ionised or radicalised oxygen to the waste load accelerates the natural decomposition process of the organic waste, and allows reduction of waste volume through the waste processing machine 110 by between 60-90%. In some embodiments, the ioniser 415 may be as described in Japanese patent publication number 2017-189413, the contents of which is hereby incorporated by reference. In some embodiments, the ioniser 415 may be as described in Japanese patent publication number 2017-189413 but without the adjustment mechanism described in the Japanese patent publication. In some embodiments, the ioniser 415 may comprise a MIRA™ ioniser available from Glencal Technology Co Ltd of Japan.

Examples of ionised oxygen produced by the ioniser 415 may include superoxide anion radicals ($O_2^-$), hydrogen peroxide ($H_2O_2$), and hydroxyl radicals ($OH^-$).

It is thought that the addition of ionised or radicalised oxygen in the decomposition process expedites the release of water from the waste load by breaking down otherwise resistant cell structures in the food waste (plant cells, for example). It is thought that this effect contributes significantly to the short decomposition timeframe of waste loads by the waste processing machine 110.

Additionally, it is thought that the addition of ionised or radicalised oxygen in the decomposition process reduces the output of volatile chemicals throughout decomposition, and accordingly neutralises odours in the processed waste residue particulate.

Intake Fan: The intake fan 420 may draw air in through a fan inlet 620 and blow the air out through a fan outlet 625. The intake fan 420 is configured to receive instructions from the controller 210. The air flow speed, power operation, and other functions of the air intake fan 420 may be configurable and controlled through the controller 210. The intake fan 420 may be affixed on at least one supporting member of the machine frame 1020, providing clearance from other air system components and further allowing access for servicing and maintenance.

Exhaust Fan: The exhaust fan 450 may comprise a similar or identical unit to the intake fan 420. The exhaust fan 450 is arranged to draw air, spent ionised oxygen, and airborne waste residue, through one or more exhaust ducts towards the air exhaust air filter 445, and to blow the filtered exhaust air into the nearby outside environment. The exhaust fan 450 may be affixed on the interior of the machine frame 1020, providing clearance from other air system components and further allowing access for servicing and maintenance.

Air valve: The air valve 425 is arranged to direct air flow to the air heater 430 under normal processing operation, and to the air knife assembly 460 under an offloading operation. The air valve 425 receives control instructions from the controller 210. In some embodiments, the air valve 425 directs the entirety of the air flow from the air intake fan 420 to the air knife assembly 460 to facilitate offloading of waste residue to a receiving bin, during an offloading operation.

In some embodiments, the air valve 425 directs a partial flow of air to the air knife assembly 460, while also providing a partial flow of air to the air heater 430. In such embodiments, the air intake fan 420 may be instructed by controller 210 to increase air flow and pressure to accommodate for the shared air stream.

Air Heater: The air heater 430 is provided to heat the received stream of ionised air from ioniser 415 to a configured temperature to provide a desired temperature within the processing chamber 1005. The air heater 430 may be controlled by the controller 210 and arranged to receive temperature control and operation instructions. The air heater 430 may heat the air stream to a temperature marginally exceeding the predetermined target chamber temperature (e.g. by 10-20%) to ensure that an acceptable chamber temperature range is met when the air stream enters the larger volume of the interior of the chamber 1005. The input of ionised air stream into the air heater 430 through air conduit sections 610 may be physically located on the top or bottom of the air heater, depending on space and optimisation requirements. In some embodiments, the air stream is provided at the bottom of the air heater 430, with the hot air outlet provided at the top, to maximise air flow efficiency as the heated air stream rises. The air supply conduits on the intake side may be insulated in order to minimise temperature loss between the heater 430 and the drum 230.

The target temperature range of air in the processing chamber 1005 of the waste processing machine 110 is selected to warm the food waste as it is being subjected by the mixing blades to physical forces to break it down, but not to heat it so much as to effectively "cook" the waste. For example, the target temperature range of 50-70 degrees (optionally around 55-65 degrees) has the advantage of warming the waste to a level where moisture in the food waste can readily enter the air in the processing chamber as vapour, while not heating it so much as to substantially denature the potentially nutritional contents of the waste. The processing of a waste load is achieved by the churning action of the waste processing mixer 1400, in conjunction with the accelerated decomposition afforded by the heated ionised air supply—rather than a high (e.g. 100+ degrees C.) overall temperature which may break down a waste load by cooking or thermally decomposing the waste.

In some embodiments, the target temperature range in the processing chamber 1005 is between 50° C.-70° C., with an average temperature of around 60° C. In some embodiments, the target temperature range in the processing chamber 1005 is between 55° C.-65° C., with an average temperature of around 60° C. In some embodiments, the temperature range may be dynamically controlled by the controller 210 throughout the course of a decomposition cycle. The temperature range may be dependent on the particular type of waste to be processed, and may be adjusted in order to provide ideal decomposition conditions. In some embodiments, the air heater 430 may be controlled by controller 210 to temporarily provide air through the intake side at an increased temperature to compensate for heat loss during the opening of the waste processing machine 110 during waste load top ups, and to accommodate the additional heat requirement for the additional waste load. Such a temporary increase may be controlled to occur for 15 to 45 minutes and may involve increasing the outlet temperature at the heater 430 by 10% to 50%, for example. In a further example, the temporary increase may be controlled to occur for around 20 to 30 minutes and may involve increasing the outlet temperature at the heater 430 by 15% to 40%.

In some embodiments, particularly those capable of larger waste processing volumes, additional heating and/or insulation means may be provided. Such additional heating and/or insulation means may serve to more effectively retain heat within the processing chamber 1005. In such embodiments, the additional heating means may comprise a heating web comprising multiple resistive heating elements (such as wires), installed around the chamber shroud 1010. The heating web may be powered by the power supply arrangement 200. In such embodiments, the heating web may be distributed throughout a fibre insulation baffling or webbing to improve heat retention and to evenly distribute the generated heat.

Other additional heating embodiments may comprise a hot water heating system. The hot water heating system may be installed in cavities attached to or installed in the chamber shroud 1010, for example. In such embodiments, heated water or steam may be directed through enclosed channels within the shroud 1010 to provide a supplementary heating effect to processing chamber 1005. The enclosed channels may direct the steam or heated water into selected (or selectively positioned) reservoir cavities, thereby providing specifically positioned heat sources. Alternatively, the enclosed channels may be arranged to provide a dispersed ambient heat increase around the totality of the chamber shroud 1010.

In some embodiments, an internal baffling system is installed in order to maximise the heating of an air stream. The baffling may comprise a series of internal vanes arranged to direct the flow of the airstream around a circuitous flow path. The use of a baffling system may allow greater exposure for the air stream to absorb heat from the air heater 430 by increasing the internal distance travelled by the airstream, and the corresponding time that the airstream is exposed to the heating elements. This may reduce the need to overheat the air, and accordingly lower energy usage. In some embodiments, the baffling vanes may comprise heating elements. In some embodiments, the baffling vanes may further convect heat to directly heat the airstream. In such embodiments, the heated vanes increase the heating surface area to the air stream and more efficiently raise the overall air stream temperature.

Inlet plenum: The heated air stream is directed from the air heater 430 into the drum 230 by the inlet plenum 435. The inlet plenum 435 comprises a series of apertures along the lower rear interior wall of the drum 230 that allow heated air to be provided directly into the waste load of the chamber 1005, as shown in FIG. 4B, for example. In some embodiments, the outlet of the inlet plenum 435 into the chamber 1005 further comprises an angled shield. The presence of the angled shield that directs the heated and ionised air downward along the lower wall of the drum 230 helps to avoid waste particulate obscuring the plenum apertures. The inlet plenum may be positioned close the waste load or within the expected volume of waste, to allow the maximum amount of contact between the heated ionised air stream and the waste load during the peak effectivity window of the ionised oxygen. The peak effectivity window of the ionised oxygen may be variable depending on the ioniser 415, and may be configurable by the controller 210. In some embodiments, the peak effectivity window of the ionised oxygen may be up to 6 seconds.

The mixing action of the waste processing mixer 1400 allows greater penetration of the air stream into a waste load present in the chamber 1005 of the drum 230, providing greater surface area exposure to the heated ionised air stream. The heat and movement of the air stream, in addition to the ionised or radicalised oxygen, allows for effective evaporation of liquid from the waste load.

Exhaust Vents: Exhaust vents 440 comprise at least one port providing an outlet from the chamber 1005 of the waste processing machine 110. In some embodiments, the exhaust vents 440 may be positioned external to the chamber, such as immediately outside the loading aperture, to minimise or avoid exhausting heated ionised air within its peak effectivity window. In some embodiments, the exhaust vents 440 are positioned either side of the inlet hatch 1710, minimising the exhausting of active ionised air and providing position to exhaust spent air away from the inlet hatch 1710. When the loading hatch is open, the exhaust fan 450 may continue to operate, in order to minimise human exposure to waste fumes.

In some embodiments, the drum ceiling may be substantially flat, and the overall drum profile may comprise a 'U' shape with a curved lower portion capped by a ceiling. In such embodiments, the at least one exhaust vent 440 may comprises an exhaust plenum and may be positioned in the ceiling (i.e. top inside surface) of the drum 230. In such embodiments, the exhaust vent 440 may be situated in the top corners of the drum profile, providing a clearance from the mixing blade arms 820 to minimise the risk of drawing excess waste particulate in the exhaust vents 440.

In some embodiments, the exhaust vents 440 comprise a combination of ports and exhaust plenums.

Air conduit sections: The components of the air flow system 220 may be connected through air conduit sections 610. The air conduit sections 610 may comprise conduits and joining sections composed of steel, aluminium, plastic, PVC, corrugated tube, or other suitable materials. In some embodiments the air conduit section material is selected based on minimising heat loss throughout the system. In some embodiments the air conduit sections 610 comprise flexible tube portions, facilitating ease of access to air flow system components for maintenance, servicing, or removal.

Figure 4:
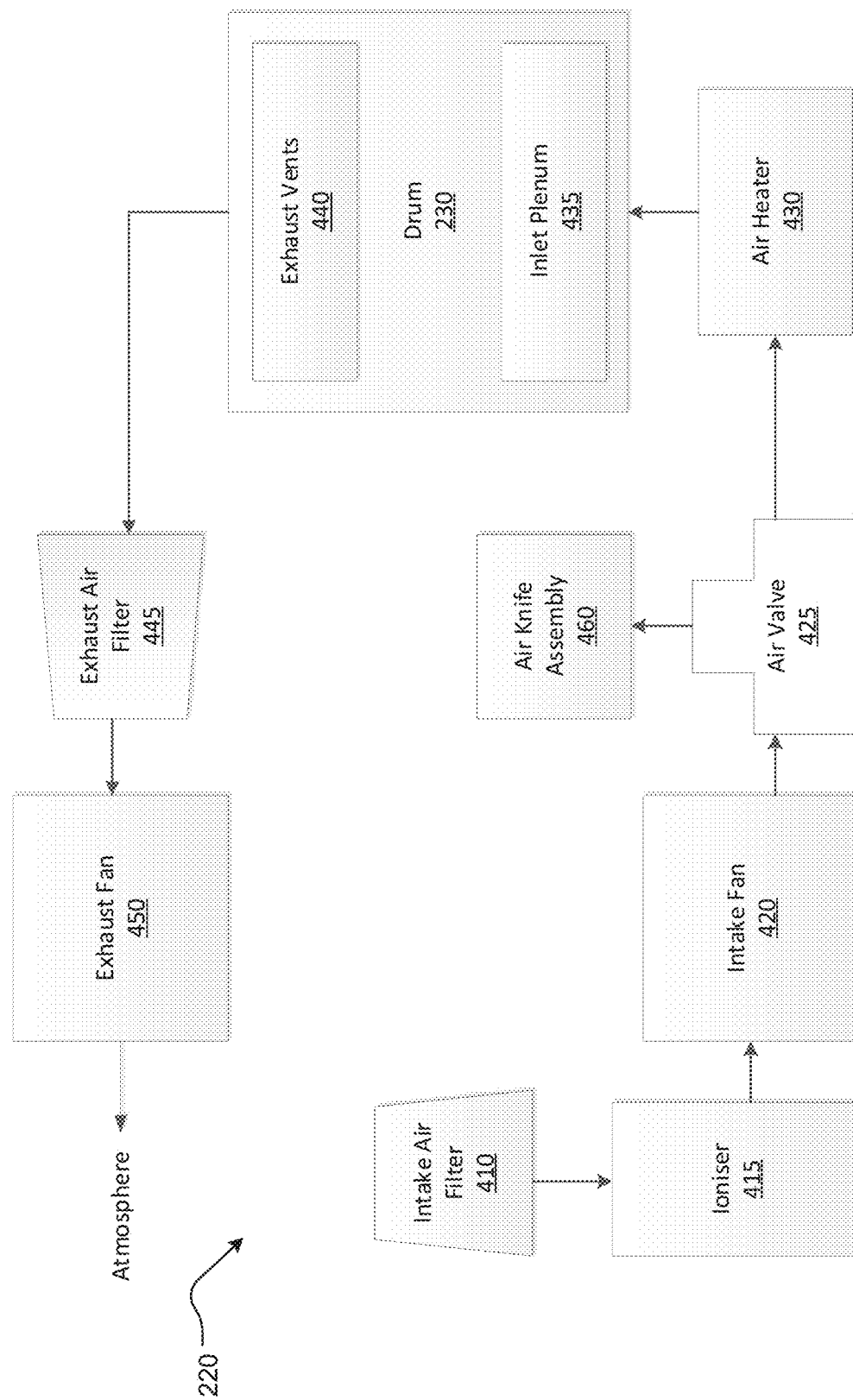
FIG. 4 is a block diagram of an air flow system of a waste processing machine according to some embodiments.
Figure 5C:
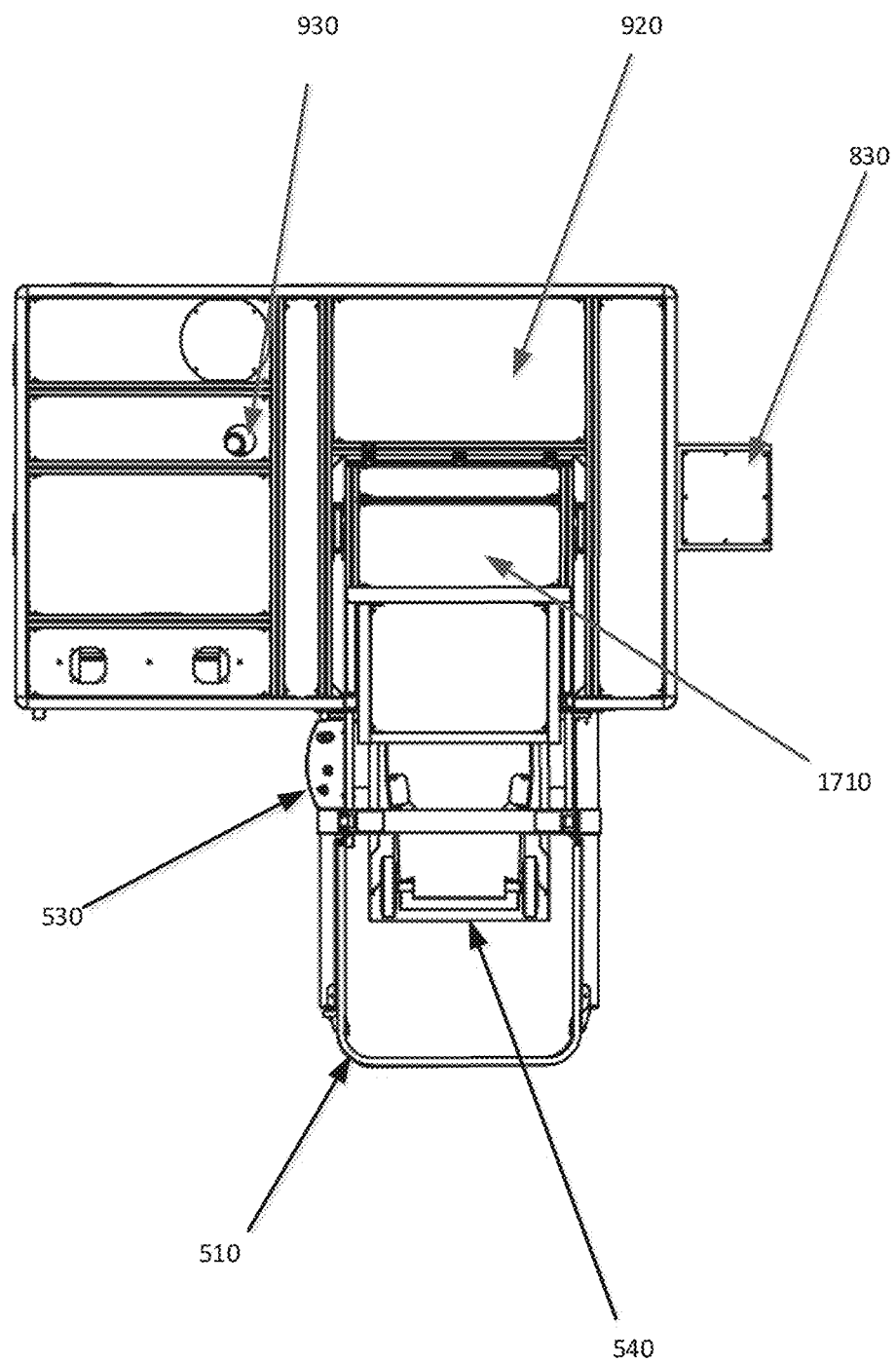
FIG. 5C is top view of a waste processing machine as shown in the FIGS. 5A and 5B.
Figure 6:
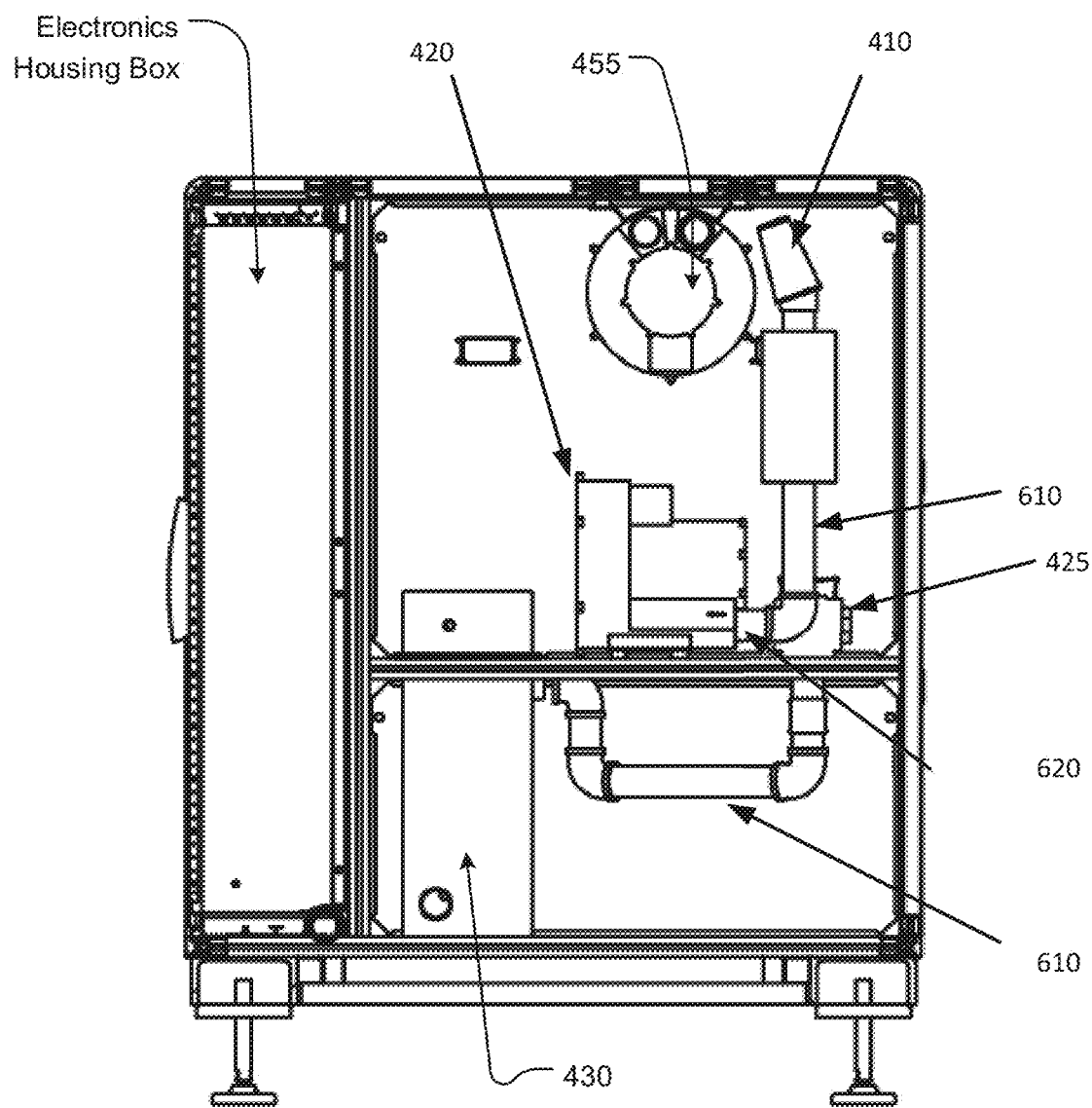
FIG. 6 is a sectional view of a waste processing machine along section line A-A of FIG. 5A.
Figure 7:
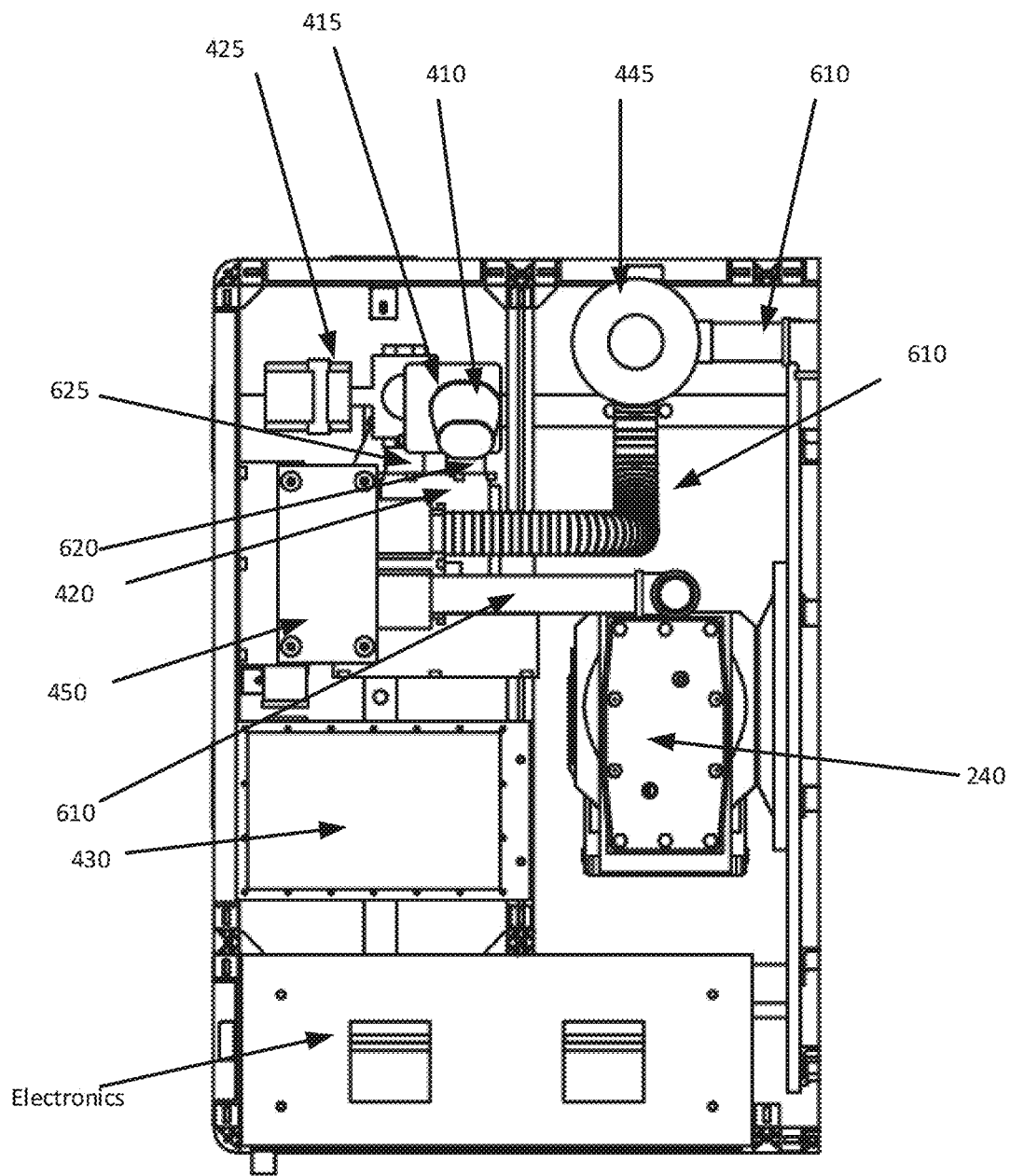
FIG. 7 is a partial sectional view of a waste processing machine along section line B-B of FIG. 5B.
Figure 8:
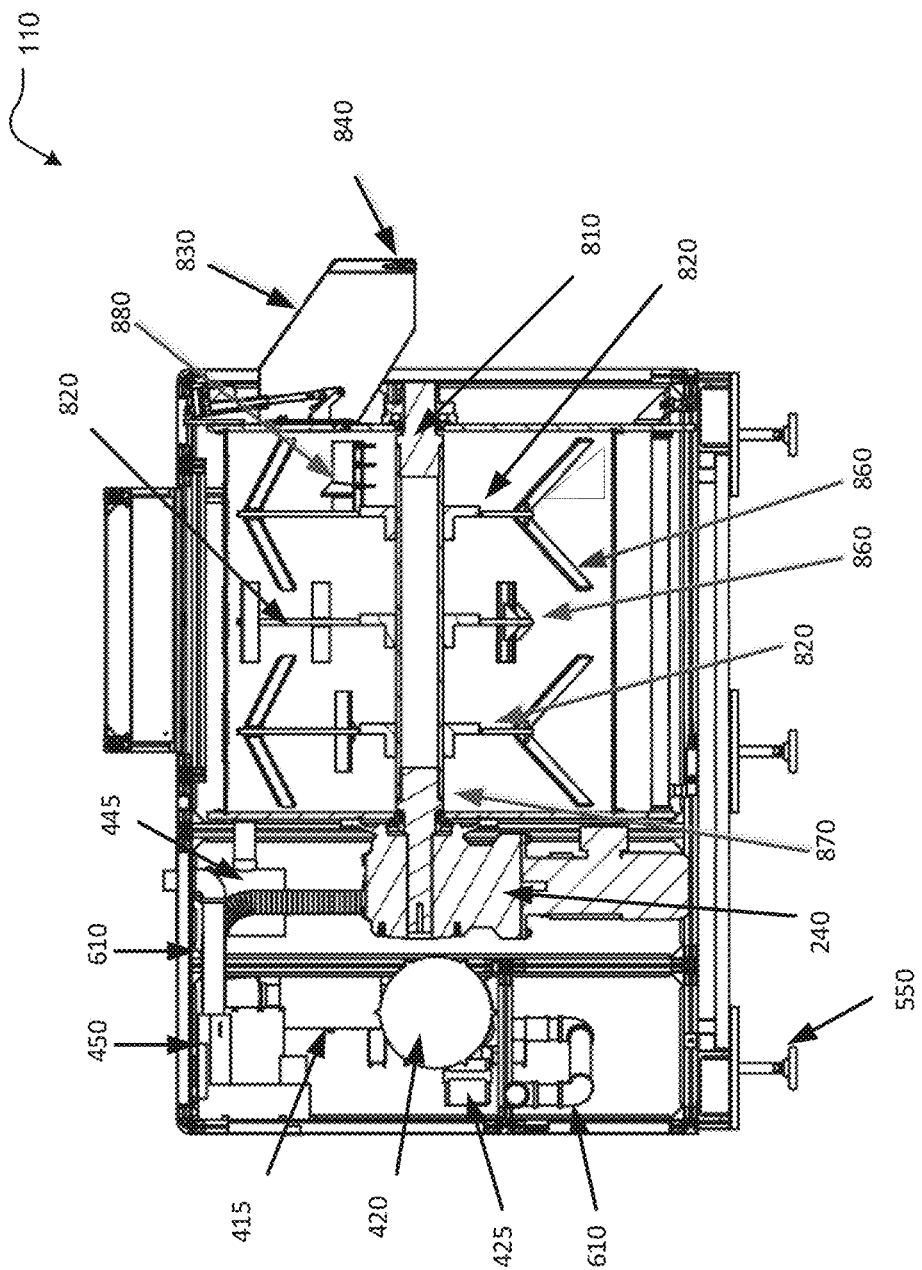
FIG. 8 is a sectional view of a waste processing machine along section line C-C of FIG. 5B.
Figure 12B:
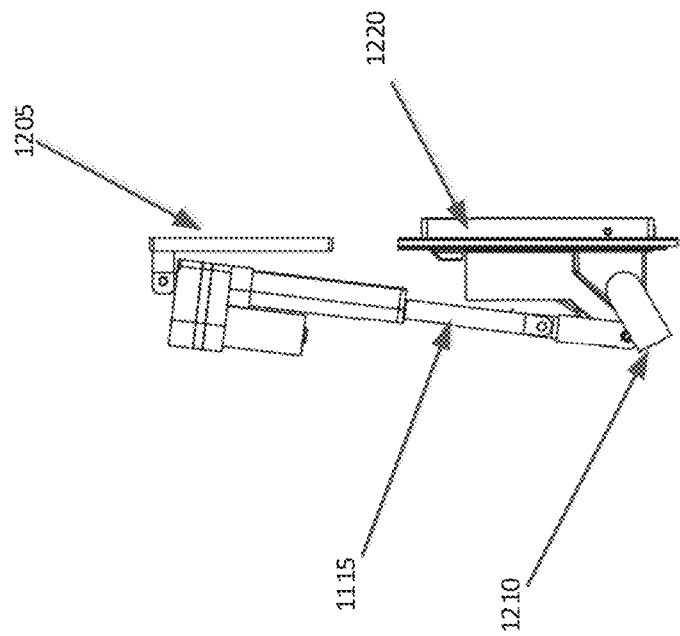
FIG. 12B is a side view of the outlet chute system of FIG. 12A, shown with the outlet hatch in the closed position.
Figure 12A:
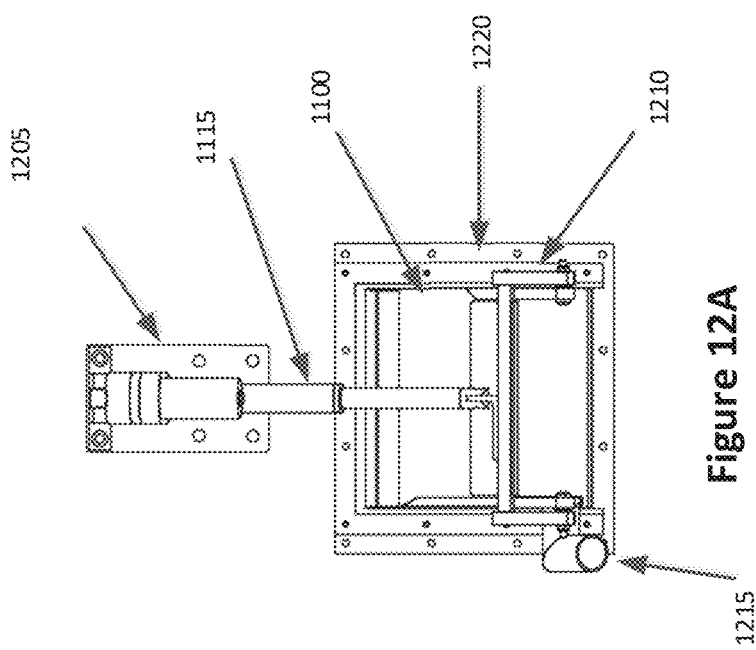
FIG. 12A is a front view of an outlet chute system of a waste processing machine according to some embodiments, shown with an outlet hatch in the closed position.
Figures 13A, 13B:
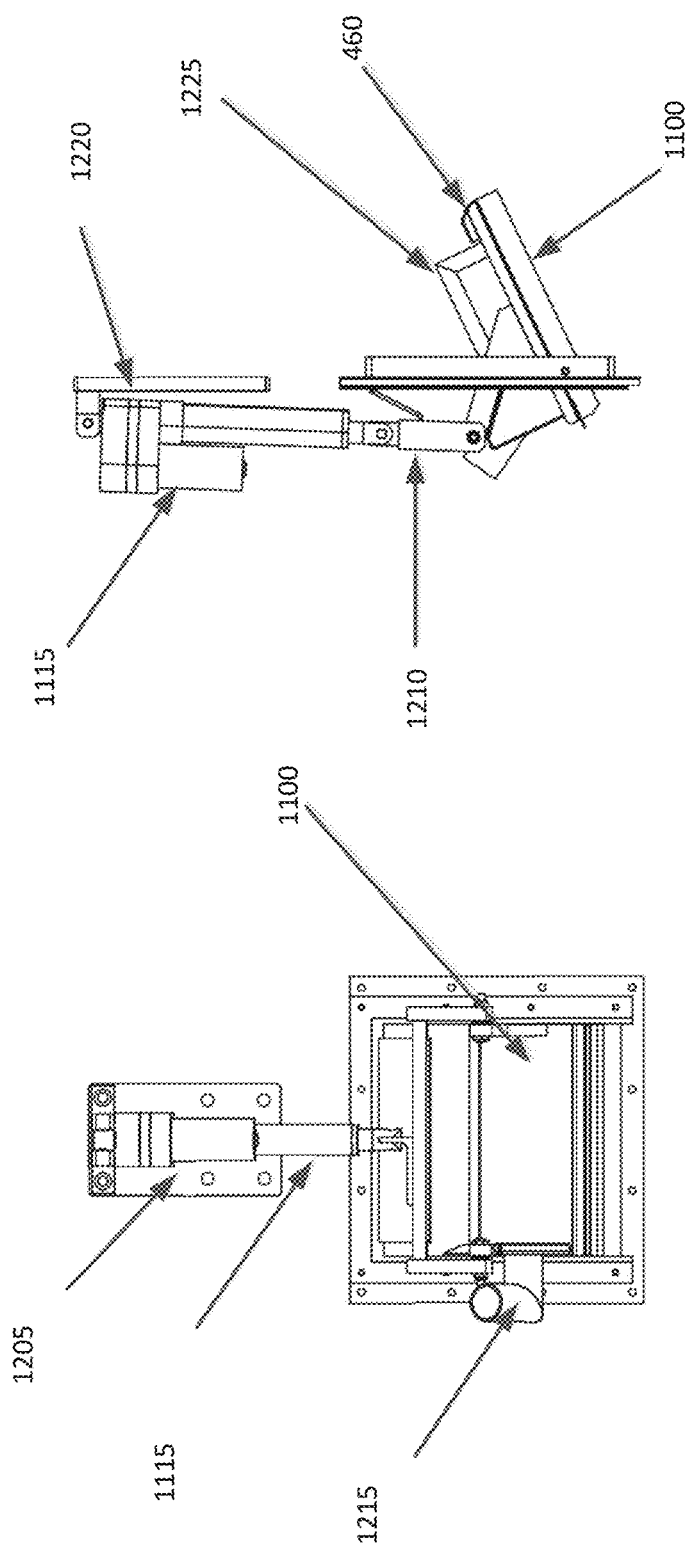
FIG. 13A is a front view of the outlet chute system of FIG. 12A, shown with the outlet hatch in the open position.
FIG. 13B is a side view of the outlet chute system of FIG. 12A, shown with the outlet hatch in the open position.
Figure 13D:
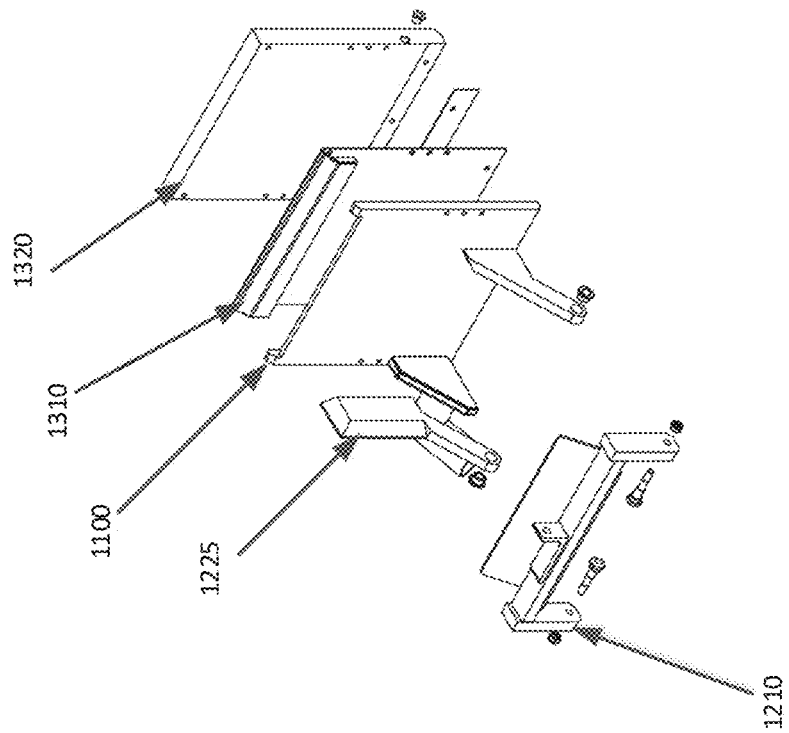
FIG. 13D is an exploded perspective view of the outlet hatch of FIG. 12A.
Figure 13C:
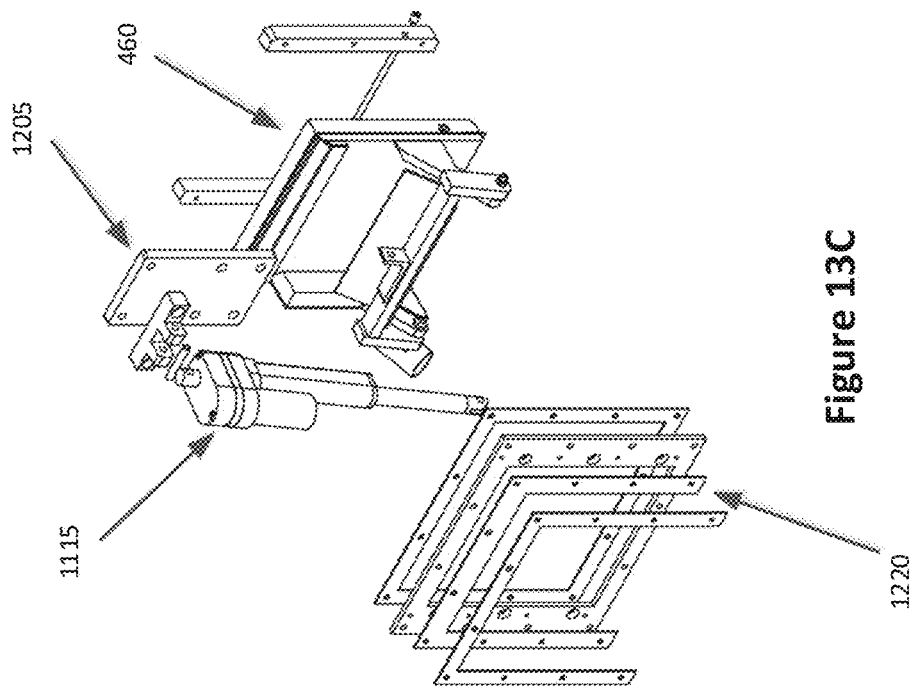
FIG. 13C is an exploded perspective view of the outlet chute system of FIG. 12A.
Figure 17:
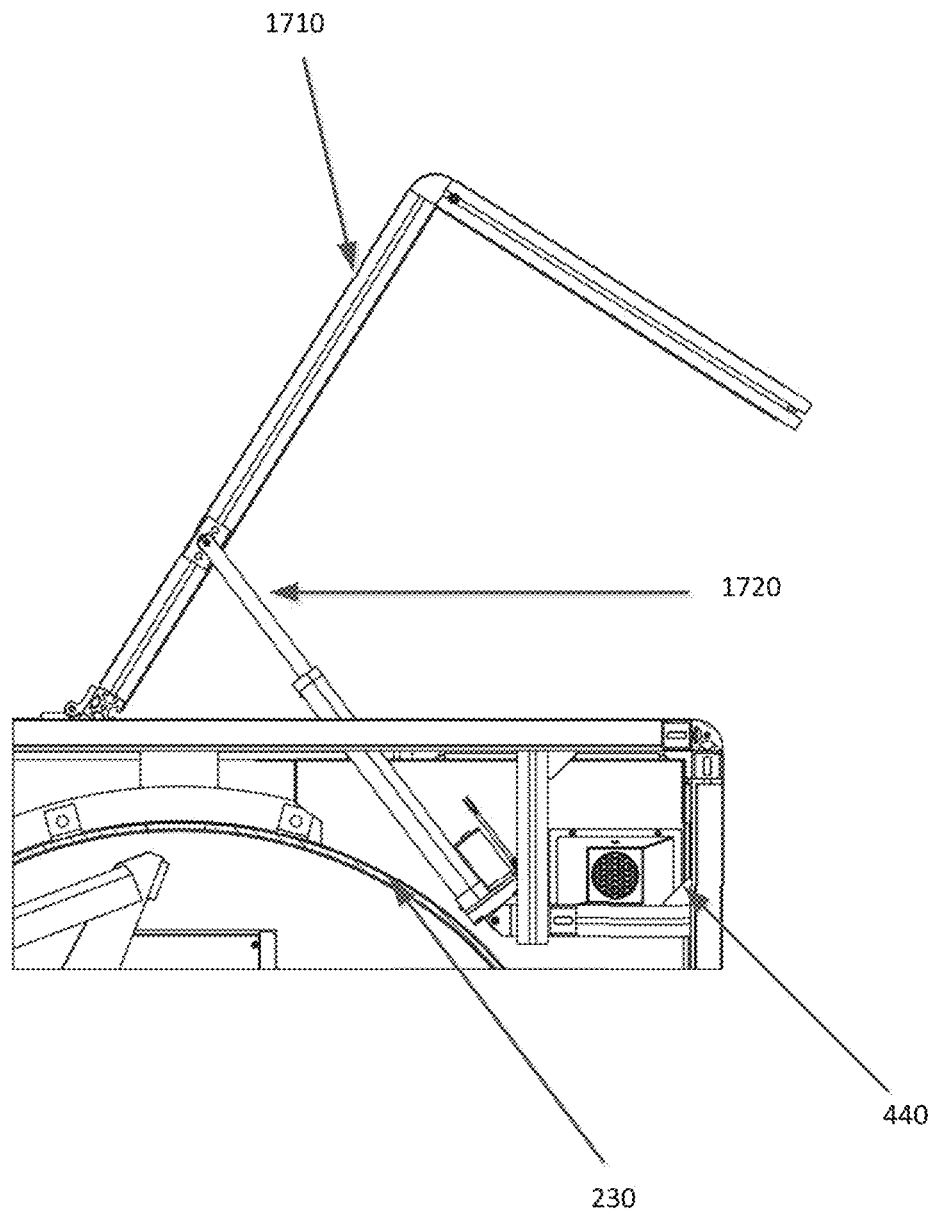
FIG. 17 is a side sectional view of a waste processing machine inlet hatch according to some embodiments.

FIG. 4 depicts an overall system diagram indicating positions and connections of an air flow system 220. In this embodiment, environmental air is drawn in through the intake air filter 410 by activation of the intake fan 420, and into an ioniser 415. After the ionisation of the filtered air stream takes place, the ionised air is directed by the air intake fan 420 through the valve 425 into either the air knife assembly 460 (during offloading or disgorgement of the waste residue) or the air heater 430 (during a normal waste processing and decomposition cycle). After the ionised air stream is heated to provide a desired chamber temperature by the air heater 430, the heated ionised air stream is directed through the inlet plenum into the chamber 1005.

From the chamber 1005, waste air is exhausted through the exhaust vents 440. In the pictured embodiment of FIG. 4, the exhaust vents 440 comprise both an exhaust plenum and exhaust ports located proximally close to the inlet hatch 1710. The exhaust fan 450 draws the waste air through the exhaust vents 440 and into the exhaust air filter 445. Waste particulate is trapped within the exhaust air filter 445 before the filtered exhaust air stream is directed out into the atmosphere.

In some embodiments, the ioniser 415 may be positioned after the valve 425 and before the air heater 430 to avoid sending ionised air through the air knife assembly 460.

Waste Loader System: The waste loader system 260 comprises a bin cradle 540, loader cage 510, loader support arm 520, and loader control interface 530. The waste loader system 260 is configured to receive a variety of standard sized wheel-bins, and to load their waste contents into the drum 230 of the waste processing machine 110.

When activated, the bin cradle 540 may be elevated along grooved tracks of the loader cage 510 to elevate a contained bin to a defined height, and is then angled by the loader support arm 520 to empty the contents of a bin into the drum 230 when the inlet hatch 1710 is opened.

The bin cradle 540 provides a supporting frame to the waste loader system 260 and shields the waste loader system operator from potentially hazardous moving parts of the system.

In some embodiments, the waste loader system 260 may comprise a modified Simpro Dumpmaster™, capable of receiving standard sized wheel-bins of up to 250 kg, and be capable of a tipping height of up to 1.8 metres. In such embodiments, modifications may include rerouting the stock loader control interface 530 to allow control by the controller 210, thereby allowing integration of the tipping action of the waste loader system 260 with inlet hatch actuation and other systems.

In some embodiments, modifications to the Simpro Dumpmaster™ include removal of a guard projection from the angled portion of the loader support arm 520, allowing a closer fit between the machine frame 1020 and the waste loader system 260. In some embodiments, a waste bin identity sensor 310 is provided in the waste loader system 260 to detect the presence and identity of bin 3405 loaded into the waste loader system 260. The waste bin identity sensor 310 may detect the presence of a bin, including its alignment or positioning, to ensure successful loading of waste.

A reader may be present on the waste processing machine 110 to detect a Radio Frequency identification (RFID) tag, near-field communication (NFC) tag or other machine-readable item on a bin, to read a unique bin identifier on the bin 3405. The database 160 may hold records associating the unique bin identifiers with a subscriber or user of the distributed waste processing system 100. In some embodiments, when the waste loader system 260 loads waste from bin 3405; the unique bin identifier may be read and transmitted to the controller 210. After loading the contents of the bin 3405, the variation in the total weight of contents of the drum may be determined using information from weight sensor 235 by the controller 210. The variation in the total weight of contents of the drum may be associated with the read unique bin identifier as the weight of the contents deposited. The read unique bin identifier value and the weight of contents value may be transmitted by the controller 210 to the database 160 along with a timestamp and a unique identifier for the particular waste processing machine 110. The recorded unique bin identifier values and the weight of contents values may be used to invoice or bill users of the distributed waste processing system based on the weight of the waste processed through specific waste bins allocated to the users. In some embodiments, the waste loader system 260 may require authentication by a user before waste is loaded into the drum. The authentication may occur through the HMI 270 or a near field communication device (not shown) mounted on the waste loader system 260.

Authentication by a user before loading waste may serve the function of identifying the user of the distributed waste processing system 100 and may eventually be used for billing or invoicing purposes. In some embodiments, information about the identity of the user of the distributed waste processing system or the unique bin identifier may also be used to identify the origin of waste loaded at a particular time. In cases of malfunction of the waste processing machine 110, this information could allow the discovery of the source of waste that could be the cause of the malfunction of the waste processing machine 110. For example, loading of metal objects in the drum may impede the operation of the waste processing machine. With information of identity of the user or the unique bin identifier, the user or subscriber responsible for loading of the metal object may be identified.

Inlet Hatch: The inlet hatch 1710 comprises a set of housing panels 920 arranged perpendicularly, forming a 90° angle at the top of the machine housing 910. The inlet hatch 1710 may be hinged to allow actuation by an inlet actuator arm 1720 in response to control signals from controller 210, providing access to the chamber 1005 by way of the chamber waste inlet aperture 1065. The inlet hatch 1710 may be controlled by controller 210 to open and close automatically during the loading process, or manually as required to inspect the drum 230 during servicing operations.

In some embodiments, the inlet hatch comprises a shielding layer, installed on the interior of the housing. The shielding layer may reduce the risk of processed waste residue and new waste loads from falling outside of the waste inlet aperture 1065.

In some embodiments, additional shielding may be installed on the inlet hatch 1710 on either side of the hatch, such that in an open position the shielding would minimise human interference and risk of injury from the top or sides of the waste processing machine 110. In other embodiments, this shielding forms part of the bin loader 3430.

In some embodiments, the periphery of the inlet hatch 1710 may include a rubber environmental seal, reducing the risk of waste entering the outside environment; minimising pollution and odours.

Machine Housing: The waste processing machine 110 is housed within a machine housing 910 that may comprise a series of housing panels 920 affixed to a machine frame 1020.

The housing panels 920 may be sheet metal panels made of aluminium, stainless steel, acrylic, or other suitable materials. The housing panels 920 may be powder coated for heat resistance and protection against environmental weathering. In some embodiments, the housing panels 920 are protected by paint, wrap coatings, or other suitable means.

The housing panels 920 may be affixed and removed from the machine frame 1020 in sections, allowing access to all inner components of the waste processing machine 110 for maintenance or servicing. In some embodiments, housing panels 920 may be installed on hinges suitable to open and close regularly accessed areas of the machine housing 910, such as the power and controls systems.

The housing panels 920 may be fitted with handles or housing panel hand grips, 940 allowing easier removal of housing panels 920.

Housing panels 920 may define one ventilation aperture or a series of ventilation apertures 930 for air flow system 220 components such as air conduits 610 to vent waste air into the atmosphere.

The machine frame 1020 comprises a plurality of frame sections arranged to provide an overall structure for the housing panels 920. The machine frame 1020 may be made of aluminium, stainless steel, or other suitable materials sufficient to provide structural integrity against environmental or operational damage.

In some embodiments, the machine frame 1020 includes a number of frame sections arranged as structural supports for waste processing machine components, such as air flow system 220 components.

The machine frame 1020 may be installed upon a mounting floor 1030, comprising a flat surface provided to form the base of the waste processing machine 110. The mounting floor 1030 may provide a stable surface to mount waste processing machine components on, including the drum 230, air flow system components, and the machine housing 910. The mounting floor 1030 may also serve to prevent environmental contamination by processed waste residue or unprocessed waste falling out of the chamber drum 230 or outlet chute 830.

In some embodiments, the mounting floor 1030 defines a mounting floor aperture 1035 beneath the drum chamber shroud 1010, which may assist in ventilation and providing access to environmental air to be drawn into the air flow system 220.

A plurality of frame support feet 550 are affixed to the underside of the mounting floor 1030 and machine frame 1020. The frame support feet 550 elevate the machine housing 910 a distance above the ground, allowing for improved environmental air flow through the mounting floor aperture 1035, reducing potential damage to the machine housing from contact with the hard ground surfaces, and reducing potential damage to ground surfaces by the moving, installation, or removal of the waste processing machine 110.

Drum: The drum 230 comprises a chamber shroud 1010, a first chamber wall 1040, and a first chamber wall 1050 defining an internal chamber 1005. The drum 230 may be made of aluminium, steel, stainless steel, or other suitable materials. The chamber size, as defined by the drum 230, may be of a suitable size to contain 1000 L at maximum capacity. In some embodiments, the chamber size may be of a size to contain a different maximum waste volume, such as 1600 L, 2000 L, 2400 L, 3000 L, 4000 L, 5000 L or 10,000 L for example. In some embodiments, the drum 230 may be configured to have other volumetric capacities. For example, in some embodiments, the chamber size may be of a size to contain a maximum waste volume of between about 500 L and about 20,000 L.

The drum 230 acts as a mixing drum where waste loads are combined with existing processed waste residue inside the chamber 1005 and subjected to the process of mixing, churning, aerating, and exposure to the heated ionised air stream in order to rapidly decompose the food waste.

The chamber shroud 1010 comprises a cylindrical tube section with a chamber waste inlet aperture 1065 allowing waste loads to be deposited within the chamber 1005 to undergo processing. In some embodiments, the chamber shroud 1010 comprises a 'U' shaped profile, having a curved bottom, and providing a flat roof allowing better clearance for drum weight sensors 235, exhaust vents 440, and other internal chamber components. In some embodiments, a drum service aperture 1090 is provided, forming a removable plate within the lower portion of the drum, to be removed to gain access to the chamber 1005 for maintenance or service purposes.

First and second chamber walls 1040, 1050 act as end walls of the drum 230 and provide external support to the chamber shroud 1010, affixing it to the mounting floor, and elevation in order to allow for larger bins to fit beneath the outlet chute 830.

The first chamber wall 1040 is positioned next to the motor 240, and has suitable apertures allowing the mixing shaft 810 to extend through the wall 1040 and rotate within the chamber 1005. The second chamber wall 1050 has a mixing shaft end mounting fixture 1080 for mounting the end of the mixing shaft while allowing it to freely rotate under the drive force of the motor 240. The first chamber wall 1050 may also define a chamber outlet aperture 1060 for the outlet hatch 1100 and external fixtures for the outlet actuator arm fixing plate 1205 and outlet chute 830. The chamber outlet aperture 1060 may be of a sufficient height on the first chamber wall 1050 to ensure clearance for standard wheeled bins, such as bin 3405, to be positioned open beneath the outlet chute 830.

The chamber walls 1040, 1050 and the chamber shroud 1010 may be permanently joined together by welding, or other suitable processes, such that they form a substantially leak proof seal preventing waste particulate from falling out of the chamber 1005. In some embodiments, the chamber walls 1040, 1050 and the chamber shroud 1010 may be separable for maintenance, cleaning, or servicing purposes.

In some embodiments, drum support feet 1070 may be installed on the lower portion of chamber walls 1040, 1050, providing additional mounting or support between the drum 230 and the mounting floor 1030.

The drum 230 has at least one drum weight sensor 235, which may comprise at least one load cell, allowing accurate weight measurements of the drum contents, and at least one temperature sensor, allowing temperature readings to be taken from the air streams at the air inlet plenum and the exhaust plenum. The sensors may be installed directly within the chamber 1005 or may be disposed on a mounting protruding into the chamber 1005.

Load cells are provided to enable accurate measurement of the weight of drum contents. The load cells provide weight readings to the controller 210. In some embodiments, three load cells are used to provide more accurate measurements. The load cells may be installed on or under chamber walls 1040, 1050, within the chamber shroud 1010, or on at least one drum support foot 1070.

The load cells may provide continuous weight data to the controller 210 in order to calculate load weight (for newly added food waste loads), offload weights, operational weights, and overall weight variations (e.g. reductions) before, during and after processing. Load cell data received by controller 210 may be used in reporting the overall performance waste processing machine 110.

In some embodiments, three load cells are provided to take an overall drum weight, which may be averaged for accuracy. In such an embodiment, load cells may be placed under points on the front and back facing sections of the machine frame 1020, and under the drum support foot 1070

The load cells may be used to specify a minimum drum weight, allowing for a threshold (or minimum) amount of processed waste residue to remain within the chamber 1005 during offloading operations. Leaving an amount of processed waste residue within the chamber 1005 has been shown during experimental operation to allow for more efficient decomposition of new waste loads and appears to help maintains consistency of the nutritional and chemical content of processed waste.

In some embodiments, the threshold amount of waste residue to be retained in the drum 230 may be 25-30% of the total maximum weight capacity of the drum. In some embodiments, the threshold amount may be a fixed weight value, such as around 100 kg to around 150 kg for a 1000 L drum. In some embodiments, the threshold amount may be 25-30% of the peak weight of a new waste load, or a fixed weight value, whichever is greater.

When the load cells detect the weight of the drum 230 being at or below the minimum threshold value, the waste processing machine 110 may cease offloading operations through the outlet chute system 250. Weight measurements may be taken at various points throughout a processing operation to track the drum weight and compare it against the threshold weight value.

In some embodiments, a remotely accessible camera may be installed within the chamber 1005, to provide images of drum or waste conditions.

In some embodiments, the chamber shroud 1010 may include a series of apertures along the back end, diagonally opposite from the chamber waste inlet aperture 1065, forming an inlet plenum 435 for entry of the ionised heated air into the chamber 1005. In some embodiments, the apertures may be formed on the front end, proximally beneath the chamber waste inlet aperture 1065.

In some embodiments, exhaust vents 440 are installed on the upper region of the chamber shroud 1010, in either a cylindrical or 'U' shape configuration.

Waste Processing Mixer: The waste processing mixer 1400 comprises a rotatable shaft 810, affixed to a motor drive connection 870 (which is in turn connected to motor 240), and at least one mixing blade fixing plate 1410 each supporting at least one mixing blade arm 820. The mixing blade arms have at least one mixing blade end 860 at radial ends of the arms. The waste processing mixer 1400 is configured to churn and break apart a waste load deposited within the chamber 1005, and to allow the waste load to receive maximum exposure to the heated ionised air stream from the air flow system 220.

The mixing shaft 810 comprises a cylindrical tubular member connecting to the motor 240 to provide a rotational movement as an axle, allowing the mixing blade arms to churn through the waste load deposited within the chamber 1005. The mixing shaft 810 may be a solid or hollow member constructed from stainless steel, aluminium, or other suitable materials. In some embodiments, additional shaft covering sections 890 are provided to protect the mixing shaft 810 from damage, and providing fixtures for the mixing blade fixing plates 1410.

The mixing shaft 810 is held in place within the chamber 1005 with one end being fixed by the motor 240 and the opposing end through the mixing shaft end fixture 1080, which maintains the horizontal position of the mixing shaft 810 while permitting free rotational movement.

In some embodiments, the mixing shaft 810 may be a hollow metal cylindrical member, with a plurality of apertures along the length. In such embodiments, the air flow system 220 may be arranged to provide a heated ionised air stream through the mixing shaft 810.

The mixing blade fixing plates 1410 are installed at various points along the length of the mixing shaft 810. The mixing blade fixing plates 1410 provide a stable and removable fixture for the mixing blade arms 820. This allows for simplified installation and servicing of a number of mixing blade arms 820 at one time through removal and reinstallation of the mixing blade fixing plates 1410. In some embodiments, the mixing blade fixing plates 1410 allow for up to six mixing blade arms 820 to be affixed. The mixing blade fixing plates 1410 may be constructed from stainless steel, aluminium, or other suitable materials.

In some embodiments of a 1000 L drum, three mixing blade fixing plates 1410 are provided along the length of the mixing shaft 810, each with six mixing blade arms 820 affixed to their surface.

The mixing blade arms 820 comprise a length of flat metal, curved towards the direction of rotation of the mixing shaft 810. The mixing blade arms 820 are of a suitable length to reach close to the walls of the chamber 1005, while still providing a minimum clearance distance from the surfaces of the chamber 1005 and the protective hood over the ionised air inlet couple to inlet plenum 435. The mixing blade arms 820 may be constructed from stainless steel, aluminium, or other suitable materials. The mixing blade arms 820 may be affixed to the mixing blade fixing plates 1410 by rivets, screws, bolts, by welding, or other suitable fixation means.

The direction and degree of curvature of the mixing blade arms 820 may allow the arms to more effectively act against the resistance of a waste load, minimising risk of wear and damage to the blade arms as compared to a substantially straight blade arm.

The mixing blade ends 860 are provided to churn and break down a waste load during a processing operation. A variety of configurations of mixing blade ends 860 may be provided within a waste processing machine 110.

In some embodiments, the mixing blade ends 860 are configured as plough ends 865, comprising two angled members, meeting at a central middle point attached to a mixing blade arm 820 (diverging in a trailing direction of rotation) and suitable to push and direct waste material around in the chamber 1005. In some embodiments, plough ends 865 are asymmetrically arranged to direct waste material towards a desired area within the chamber 1005.

In some embodiments, the mixing blade ends 860 are configured as, or include, paddle ends 866. Such paddle ends 866 may comprise a flat panel portion, affixed in a perpendicular orientation relative to the mixing blade arm 820, which is arranged to provide a churning or pushing motion to the waste load within the chamber 1005.

The mixing blade ends 860 may be constructed from stainless steel, aluminium, or other suitable materials. The mixing blade ends 860 employ blades of different shape and configuration to generate different churning effects with in the chamber 1005 during rotation.

In some embodiments, the mixing blade ends 860 may all be configured in a similar fashion on each mixing blade fixing plate 1410. In other embodiments, the mixing blade ends 860 alternate between configurations on each mixing blade fixing plate 1410.

Figure 48:
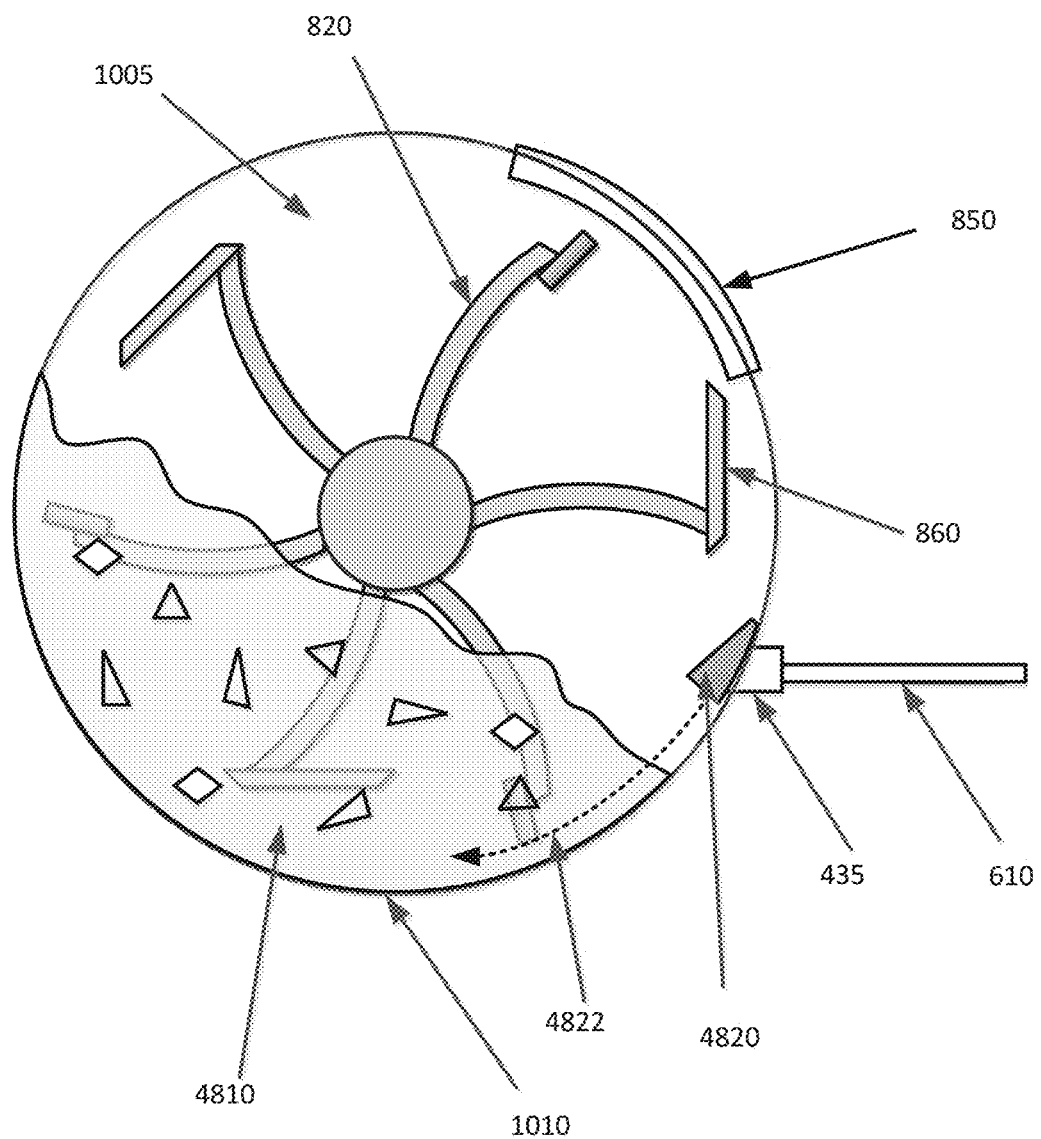
FIG. 48 is a schematic representation in end view to illustrate a typical position of a waste load (toward the end of a processing cycle) within the processing chamber of a waste processing machine.
Figure 50:
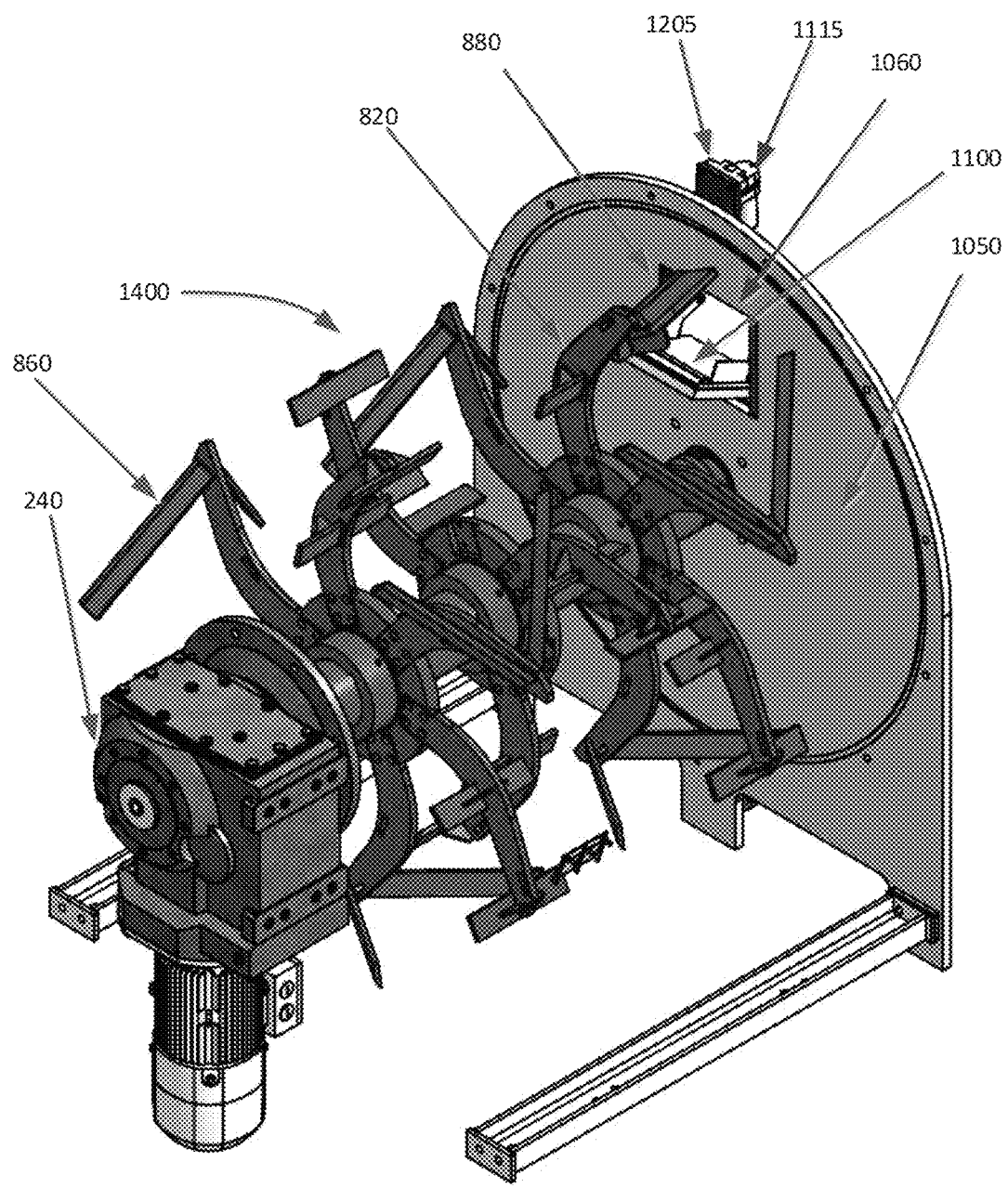
FIG. 50 is a partial perspective view of mixing components of the waste processing machine according to some embodiments, showing relative positions of the components, with the outlet hatch in an open position and with the residue scoop in a depositing position to illustrate unloading of the processing chamber.

In some embodiments, the mixing blade ends 860 may be arranged or configured to push the waste load towards different portions of the chamber 1005. FIG. 48 indicates one such embodiment, where a manipulated waste load 4810 within the chamber 1005 is pushed by the direction of rotation of the shaft and the mixing blades towards the rear of the chamber (opposite the loading hatch), while allowing a small space for the ionised air to exit the inlet plenum 435 through an air director or hood 4820 (in a direction downwardly along the drum wall as indicated by arrow 4822 in FIG. 48) and then interact with the waste. This arrangement allows significant exposure of the food waste to the heated ionised air stream.

In other embodiments, the mixing blade ends 860 are arranged or configured to push the waste load towards the outlet hatch 1100, allowing easier waste collection by a residue scoop 880.

In some embodiments, the mixing blade arms 820 are arranged to have gaps or to be spaced from each other in order to provide clear access to the chamber by a waste loader system 260, and to allow a waste load to be deposited within the drum 230 with minimal obstruction. This may be accomplished by limiting the amount of mixing blade arms 820 on one or more mixing blade fixing plates 1410 that are closest to or spatially (rotationally) aligned with the waste inlet aperture 1065. In some embodiments, this is accomplished by affixing three mixing blade arms 820, each having a paddle end 866, positioned 120° apart around the mixing blade fixing plate 1410, for example. This arrangement may provide an optimally spaced blade configuration, while still maintaining efficacy for waste processing.

The controller 210 may track the position of the mixing shaft 810 (e.g. via a position sensor associated with the shaft 810), such that when a loading operation commences via the waste inlet aperture 1065, the mixing blade arms 820 closest to the waste inlet aperture 1065 are rotated so that the blade ends 860 do not obstruct loading of waste into the processing chamber 1005. For example, the blade ends 860 may be positioned at a furthest relative point away from the loading aperture so that a mid-way point between the blade ends 860 roughly aligns centrally with the loading aperture, thereby ensuring minimal obstruction for a newly deposited waste load.

Residue scoops 880 are provided on mixing blades arms 820 affixed to the mixing blade fixing plate 1410 closest to the outlet hatch 1100, configured to carry processed waste residue from the bottom of the chamber up and over, to a point above the outlet hatch 1100, allowing the angle of the residue scoop to deposit waste residue on the outlet hatch 1100 by gravity. The residue scoops 880 may be a constructed from stainless steel, aluminium, or other suitable materials.

Outlet Chute: The outlet chute 830 is provided to channel processed waste residue from the chamber 1005 to a receiving bin on the outside of the waste processing machine 110. The outlet chute 830 comprises an air knife assembly 460, outlet actuator arm 1115, guard flange 1225 outlet air intake 1215, outlet actuator arm pivot 1210, outlet actuator arm fixing plate 1205, outlet hatch 1100, and outlet chute 830.

The outlet hatch 1100 is deployed into the chamber 1005 by the outlet actuator arm 1115 in order to receive processed waste residue by a residue scoop 880. Deposited processed waste residue is then blown through the outlet chute 830 by the air knife assembly 460. The outlet chute 830 is shaped to provide an angled portion and a downward chute portion to direct the processed waste residue into a receiving bin. The outlet hatch 1100 may be mounted to a second chamber wall 1050, by at least one framing plate 1220.

The outlet hatch 830 may be configured to be deployed in an offloading operation by interaction with the HMI 270, or by remote access by a client device 140. In some embodiments a fixed offloading time is specified, preventing either offloading operations or the addition of new food waste into the chamber 1005 by a waste loader system 260. This fixed offloading time may allow for an uninterrupted process cycle to be completed, ensuring that the processed waste residue is ready for offloading and collection at an intended time.

In some embodiments, a notification may be sent to a client device 140 indicating that a fixed offloading time has been reached, or that an offloading cycle has been completed, and a bin of processed waste residue is now ready for collection.

The outlet actuator arm 1115 may be affixed to the drum 230 by the actuator arm fixing plate 1205, forming a stable base for actuation against the second chamber wall 1050. The outlet actuator arm 1115 may be a hydraulic arm controlled by the controller 210. The actuating force is transmitted from the outlet actuator arm 1115 by the outlet arm pivot 1210 against the outlet hatch 1100. The guard flange 1225 may be levered by the outlet arm pivot 1210 to further distribute actuation force against the length of the outlet hatch 1100 and to form a barrier, collecting processed waste residue deposited by a residue scoop 880.

The air knife assembly 460 comprises a vent cavity defined by the outlet hatch 1100, a vent lip plate 1310, and backing plate 1320. The backing plate 1320 may provide additional support to the air knife assembly 460. The air knife assembly 460 receives air stream from the air flow system 220 through the outlet air intake 1215. The outlet air intake 1215 directs air into the vent cavity between the outlet hatch 1100 and the vent lip plate 1310, the vent lip plate 1310 having a lip portion extending a distance over and around the top of the outlet hatch 1100. A space is defined between the end of the outlet hatch 1100 and the lip portion of the vent lip plate 1310 to allow the air stream to be channelled and directed by the lip portion down along the external facing of the outlet hatch 1100, forming an air knife. The air knife should be of sufficient pressure to move deposited processed waste residue along the outlet hatch 1100 and down through the chute, into a receiving bin.

The outlet chute 830 may be made of aluminium, steel, stainless steel, or other suitable materials. The outlet chute 830 may house at least one bin depth sensor 840. The bin depth sensor 840 detects the level of processed waste residue in a receiving bin positioned below the outlet chute 830.

FIG. 49 depicts the relative positioning of a residue scoop 880 above the outlet hatch 1100 when the outlet hatch 1100 is deployed to receive processed waste residue. In the pictured embodiment, the mixing blade arms 820 extend beyond the height of the chamber outlet aperture 1060 in order to provide clearance of the mixing blade ends 860 and the residue scoops 880, so as to not collide with the outlet chute 1100 in either open or closed configuration.

FIG. 49 further depicts a residue scoop 880 being angled outward and towards the outlet chute 1100 to provide a directional depositing effect when rotated over the deployed outlet chute 1100, allowing waste residue to be more accurately deposited on the chute 1100, and to maximize the amount of waste residue deposited per rotation of the waste processing mixer 1400. In some embodiments, the bin depth sensor 840 provides a continuous sensing data on the level of processed waste residue in a receiving bin.

In some embodiments, the bin depth sensor 840 detects the level of processed waste residue in a receiving bin having reached a pre-set depth threshold, indicating a full bin load.

Bin Proximity Sensor: A bin proximity sensor 950 may be provided to detect the presence of a receiving bin proximally close to the housing panel 920 under the outlet chute 830. The bin proximity sensor 950 communicates with the controller 210. Should the bin proximity sensor 950 detect the presence of a receiving bin 3405, the outlet chute system 250 may be activated to direct processed waste residue into the receiving bin 3405. Should the outlet chute system 250 be activated without the bin proximity sensor 950 sensing the presence of a receiving bin 3405, the outlet chute system 250 may not engage.

In some embodiments, the bin proximity sensor 950 indicates whether an object is within a predefined distance or not. In some embodiments the bin proximity sensor indicates the type of object identified within a predefined distance; for example, whether the object is a receiving bin or not. In some embodiments the bin proximity sensor 950 detects a specific type of receiving bin, such as a 120 L, 140 L, or 240 L receiving bin for example.

In some embodiments, the bin proximity sensor 950 senses an identification tag on the object within a predefined distance, associating that with information from the server system 150 to identify the user or entity receiving the processed waste residue, particularly where multiple users or entities share usage of the waste processing machine 110.

Alternative Embodiment: FIG. 34 depicts an alternative embodiment 3400 of a waste processing machine 110. Other than the differences noted herein, the waste processing machine embodiment 3400 operates in substantially the same way and has substantially the same structure and functions as the waste processing machine 110. In embodiment 3400, the chamber shroud 1010 is of an overall length and diameter to provide a total maximum waste processing weight of around 1000 kg, for example. In embodiment 3400, the mixing shaft 10 is of a length to provide clearance for four mixing blade fixing plates 1205 affixed with mixing blade arms 820. The embodiment of FIG. 34 also comprises a front facing outlet chute 3410, and side loading bin loader 3430.

The front facing outlet chute 3410 directs process waste into a receiving bin by an outlet conveyor 3420. The outlet conveyor 3420 receives waste from the chamber 1005 by a functionally similar outlet hatch 1100, and conveys it through a conveyor aperture 3440 in the machine housing 910.

The side loading bin loader 3430 is configured to deploy a bin loading arm 3450 to raise and tip a bin into a loading chute 3460, depositing waste down the loading chute 3460 into the chamber 1005.

The motor 240 of embodiment 3400 may comprise a belt drive motor, for example.

Processed Waste: Processed waste residue as produced by the waste processing machine 110 may comprise a solid and dry decomposed organic matter particulate. Water is evaporated from the waste load during the processing operation in the chamber 1005. From the evaporation of water, the accelerated decomposition by the heated ionised air stream, and the destructive action of the waste processing mixer 1400, the total weight and/or volume of input waste can be reduced to around 20% of the input waste load by the time the processing has been completed. For example, in a drum of about 1000 L volumetric capacity, an input waste load of around 450 kg may be added to residue of around 150 kg already in the drum (retained from previous waste processing), and that input waste load may be reduced by around 80% of its mass to about 90 kg. This would then only necessitate around 90 kg of residue being removed from the processing drum 230 in the next unloading step, if all remaining residue were to be removed. However, as noted elsewhere herein, it can be desirable to retain a certain minimum amount of processed waste residue in the processing drum in order to improve processing efficiency of a subsequent load of organic waste.

The processed waste residue may be of a relatively neutral or slightly basic pH, and not contribute to any corrosive damage, skin problems, or environmental issues. For example, the processed waste residue may have a pH of between about 6 and 11, between about 7 and 10, or between about 7 and 9. In some embodiments, the processed waste residue may have a pH that is at least slightly basic. For example, the processed waste residue may have a pH of at least about 7, at least about 7.5, or at least about 8.

It has been surprisingly found that according to at least some embodiments as described herein, the process can produce processed waste residue that is at least slightly basic such that introduction of the slightly basic processed waste residue with typically acidic fresh food waste can facilitate at least an initial reaction during processing to provide a further enhanced processing capability. In some embodiments, the processes described herein comprise introduction of the processed waste residue with fresh food waste for processing, or the processes comprise retaining a residual amount of processed waste residue in the processing chamber between two or more batch processes. For example, the amount of processed waste residue provided in the chamber (i.e. introduced or retained) for processing with unprocessed food waste (by weight % of total processed waste residue and unprocessed food waste) may be at least about 5, 10, 15, 20, 25, 30, 35, 40, 45, or 50. The amount of processed waste residue provided in the chamber for processing with unprocessed food waste (by weight % of total processed waste residue and unprocessed food waste) may be less than about 60, 55, 50, 45, 40, 35, 30, 25, 20, 15, or 10. The amount of processed waste residue provided in the chamber for processing with unprocessed food waste (by weight % of total processed waste residue and unprocessed food waste) may be in the range of any two of the above lower and/or upper amounts, for example between about 5 and 60, 10 and 55, 15 and 50, 20 and 45, or 25 and 35.

The processed waste residue may retain a high nutrient load, containing levels of nitrogen, phosphorous, potassium, and other metals and minerals, allowing for the processed waste to be used as a fertilizer for soil improvement.

A comparison of the processed waste residue with other known fertilisers is provided in the below table.

| Property | Waste Residue from waste processing machine | Fresh poultry litter | Composted garden organics | De-watered biosolids | Cattle feedlot manure | Piggery solids |
| --- | --- | --- | --- | --- | --- | --- |
| pH | 8.1 | 5.8-8.1 | 6.9 | 6.7 | 7 | 7.3 |
| Moisture (%) | 30.7 | 21-36 | 26 | 82 | 20-54 | 49 |
| Nitrogen (% dw) | 2.6 | 2.6-5 | 1 | 3.7 | 0.8 | 0.7 |
| Phosphorus (% dw) | 0.5 | 1.2-2.6 | 0.2 | 3.4 | 0.8 | 0.7 |
| Potassium (% dw) | 0.8 | 1.0-2.8 | 0.5 | 0.3 | 2.3 | 1 |
| Copper (mg/kg) | 5 | 25-160 | 57 | 600 | 40 | 200 |
| Zinc (mg/kg) | 27 | 239-580 | 151 | 600 | 323 | 170 |

In some embodiments, the nutritional content of the processed waste residue is sufficient to be used as animal fodder. In these embodiments, the processed waste residue may be fed directly to animals or livestock, or be mixed with other feed stock to provide a lower total concentration of nutrients depending on livestock requirements.

In some embodiments, the processed waste residue may be used as a feed stock for use in anaerobic digestion. The consistency of the nutritional and calorific contents of processed waste residue may allow for more consistent energy output in these purposes. Additionally, the stability and storage life of the processed waste residue may be beneficial to transport and use of the residue as a fuel source.

The processed waste residue may be provided as solid particulates. The solid particulates may comprise individual particulates in a size range of about 1 micron to about 5 mm. The individual particulates may be less than about (in microns) 5000, 2000, 1000, 500, 250, or 100, for example. The processed waste residue comprising the solid particulates may have a certain composition provided by a solids content, water (moisture) content and remaining void volume.

The solids content of the processed waste residue (based on total weight %) may be in the range of about 10 to 80, 20 to 70, or 30 to 60. The solids content of the processed waste residue (based on total weight %) may be at least about 10, 20, 30, 40, 50, 60, or 70. The solids content of the processed waste residue (based on total weight %) may be less than about 80, 70, 60, 50, 40, 30, or 20. The solids content of the processed waste residue may be in the range of any two of the above lower and/or upper amounts.

The processed waste residue may have a moisture content (by weight % of the total waste residue) of less than about 30, 25, 20, 15, 10, 9, 8, 7, 6, 5, 4, 3, 2, 1, 0.5, or 0.1. The moisture content (by weight % of the total waste residue) may be at least about 0.1, 0.5, 1, 2, 3, 4, 5, 6, 7, 8, 9, 10, 15, or 20. The moisture content (by weight % of the total waste residue) may be in the range of any two of the above lower and/or upper amounts, for example between about 1 and 30, 2 and 25, or 5 and 20.

For a given volume of solid particulates, the void volume (in % of total volume of the residue) may be at least 5, 10, 15, 20, 25, 30, 35, 40, 45, 50, 55, 60, 65, or 70. For a given volume of solid particulates the void volume (in % of total volume of the residue) may be less than about 75, 70, 65, 60, 55, 50, 45, 40, 35, 30, 25, 20, 15, or 10. For a given volume of solid particulates, the void volume (in % of total volume of the residue) may be provided in a range of any two of the above lower and/or upper amounts.

The processed waste residue may be a substantially ionised residue. The processed waste residue may be substantially sterile or inert, for example having a low microbe content.

The processed waste residue may have a low odour level. For example, the processed waste residue may have a low sulphide content. Sulphides may include hydrogen sulphide, carbonyl sulphide, methyl mercaptan, ethyl mercaptan, dimethyl sulphide, n-propyl mercaptan, thiophene, n-butyl bercaptan, and tetrahydrothiophene. The sulphide content of any individual or total combined amount of sulphides may be (in ppm) less than about 100, 90, 80, 70, 60, 50, 40, 30, 20, 10, 5, 1, 0.5, or 0.1.

The processed waste residue may have an organic solids content (by weight % of total residue) in an amount of at least about 30, 40, 50, 60, 70, 80, 90, or 95. In another embodiment, the proportion of organic solids in the solids content of the processed waste residue may be (by weight % of total solid content) in an amount of at least about 50, 60, 70, 80, 90, 95, 98, or 99. It will be appreciated that the organic solids content is derived from the input source including food scrap remains such as from various animal and vegetable sources. It will be appreciated that the organic content comprises various carbohydrates, fats, lignins, and proteins, for example. The processed waste residue may also have a low volatile organic content, for example other than butanone volatile organic compounds, and may be ($\mu g/m^3$) less than about 10, 9, 8, 7, 6, 5, 4, 3, 2, 1, 0.5, or 0.1.

Figure 18:
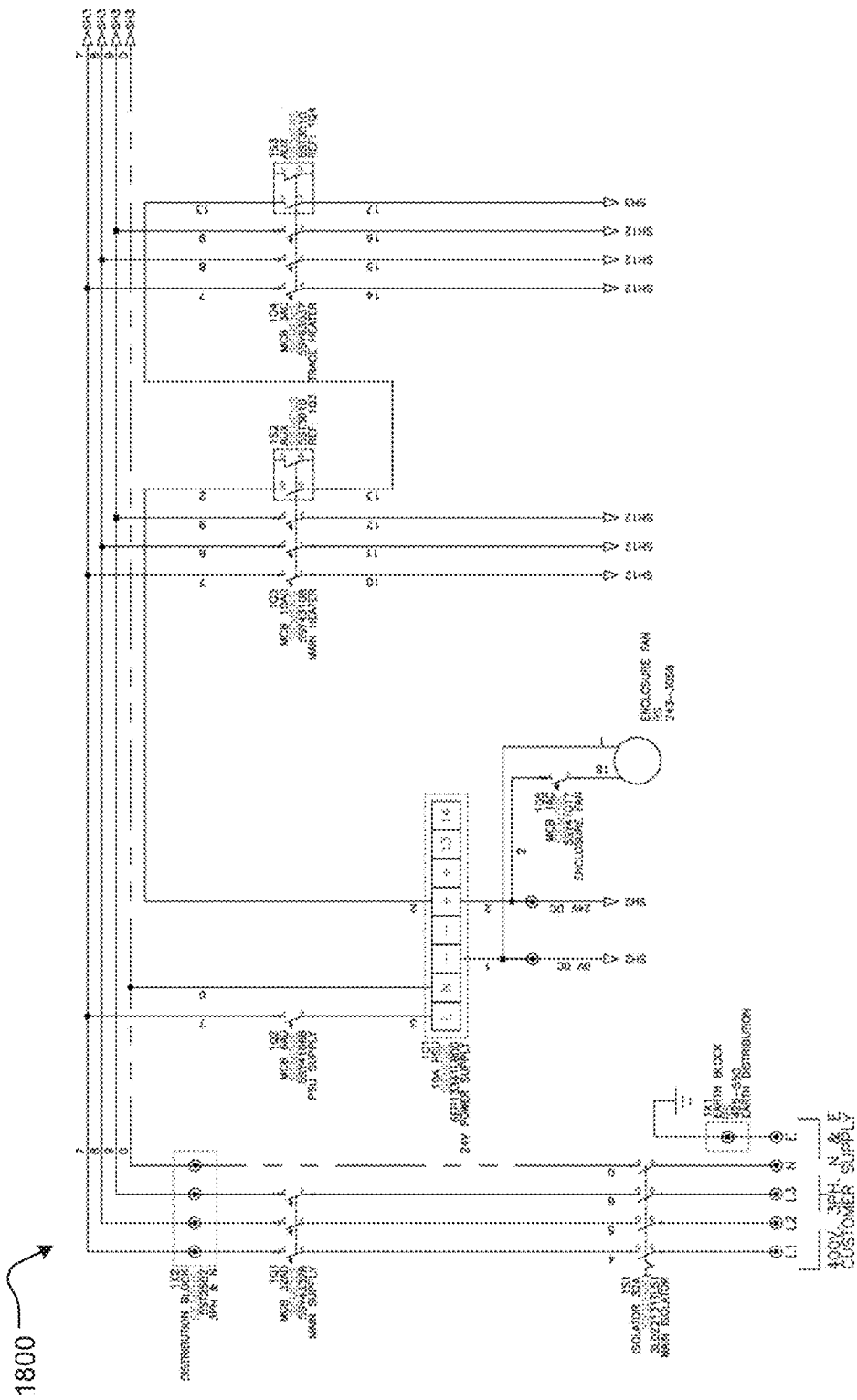
FIG. 18 is an electrical schematic diagram illustrating power distribution for a waste processing machine according to some embodiments.

FIG. 18 is an electrical schematic 1800 illustrating power distribution within the waste processing system 110 according to some embodiments. The schematic 1800 illustrates components of the power supply 280 that receive power input in 3 phase AC 400V form and use isolators, distributors, converters and other necessary electrical components to distribute power within the waste processing machine 110.

Figure 19:
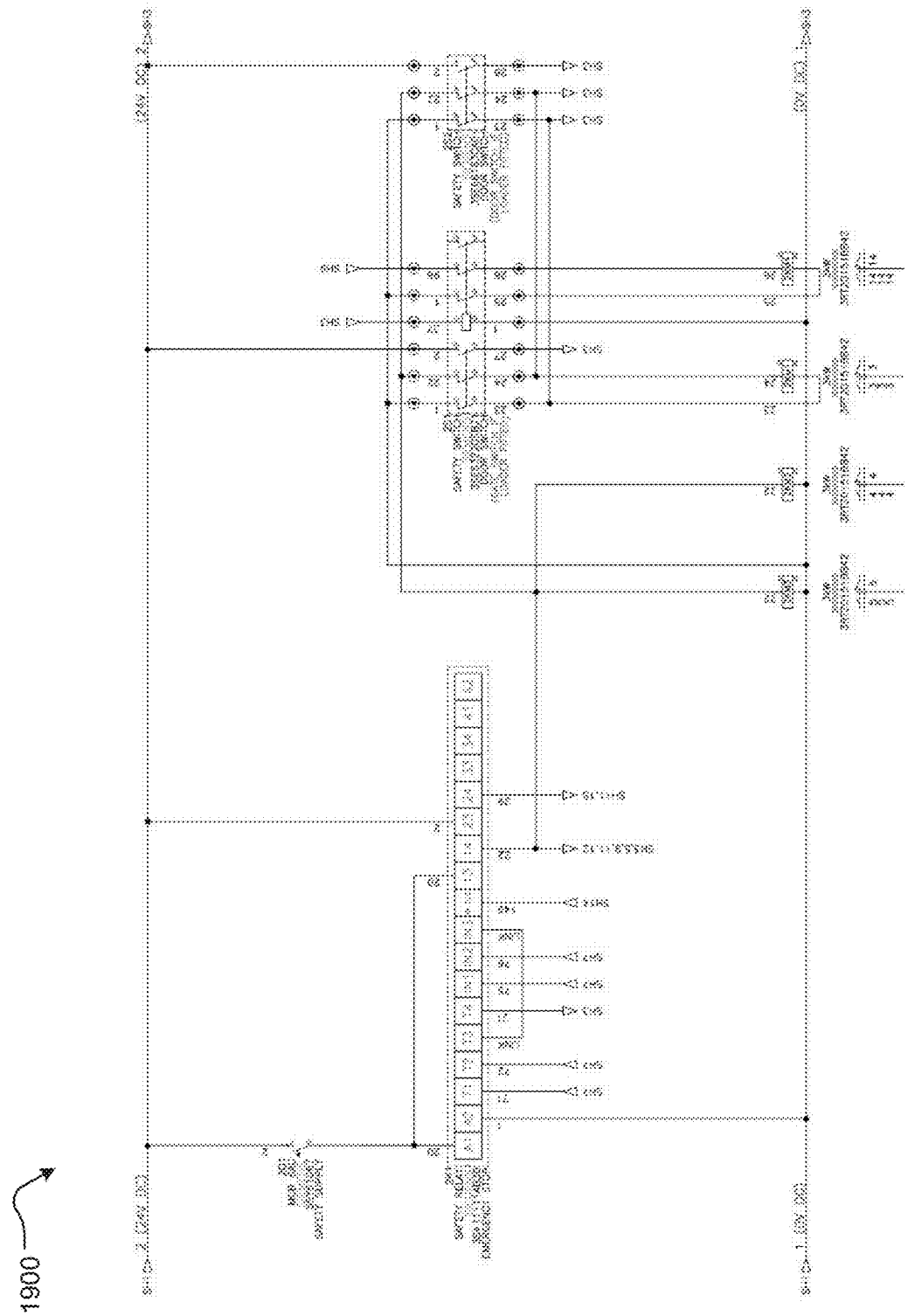
FIG. 19 is an electrical schematic diagram of a safety circuit within the waste processing machine.

FIG. 19 is an electrical schematic 1900 illustrating a safety circuit within the waste processing system 110 according to some embodiments. The safety circuit provides an electrical disengagement mechanism for the various electrical components within the waste processing system 110. The electrical disengagement mechanism may be activated in response to an open hatch or door or an emergency button located on the exterior of the waste processing machine 110 or in response to an emergency activation command from the system server 150.

Figure 20:
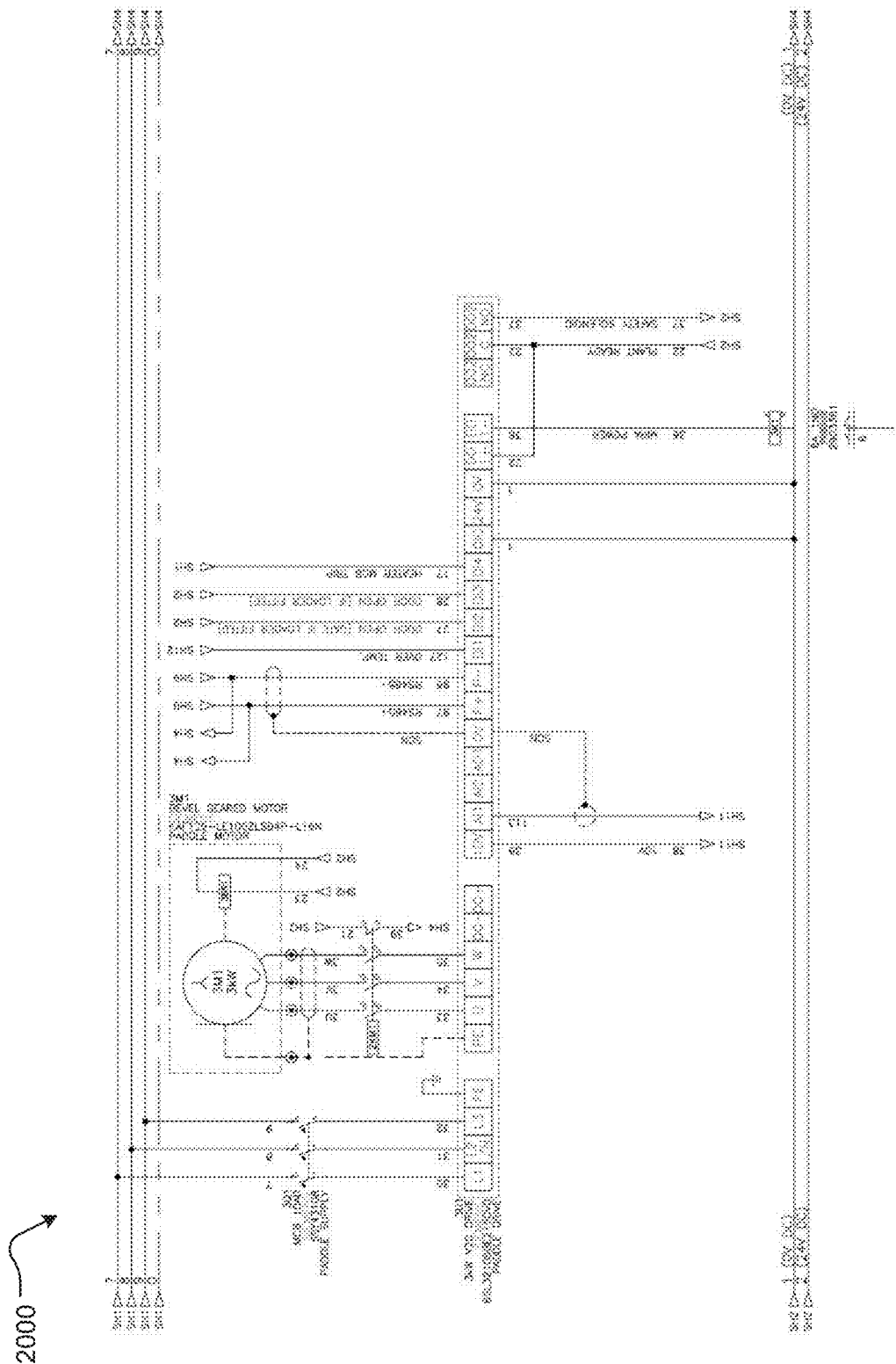
FIG. 20 is an electrical schematic diagram of a drum drive circuit within the waste processing machine.

FIG. 20 is an electrical schematic 2000 illustrating a drum drive circuit within the waste processing system 110 according to some embodiments. The drum drive circuit provides an electrical driving and control mechanism for the various motors driving the mixing assembly within the waste processing system 110.

Figure 21:
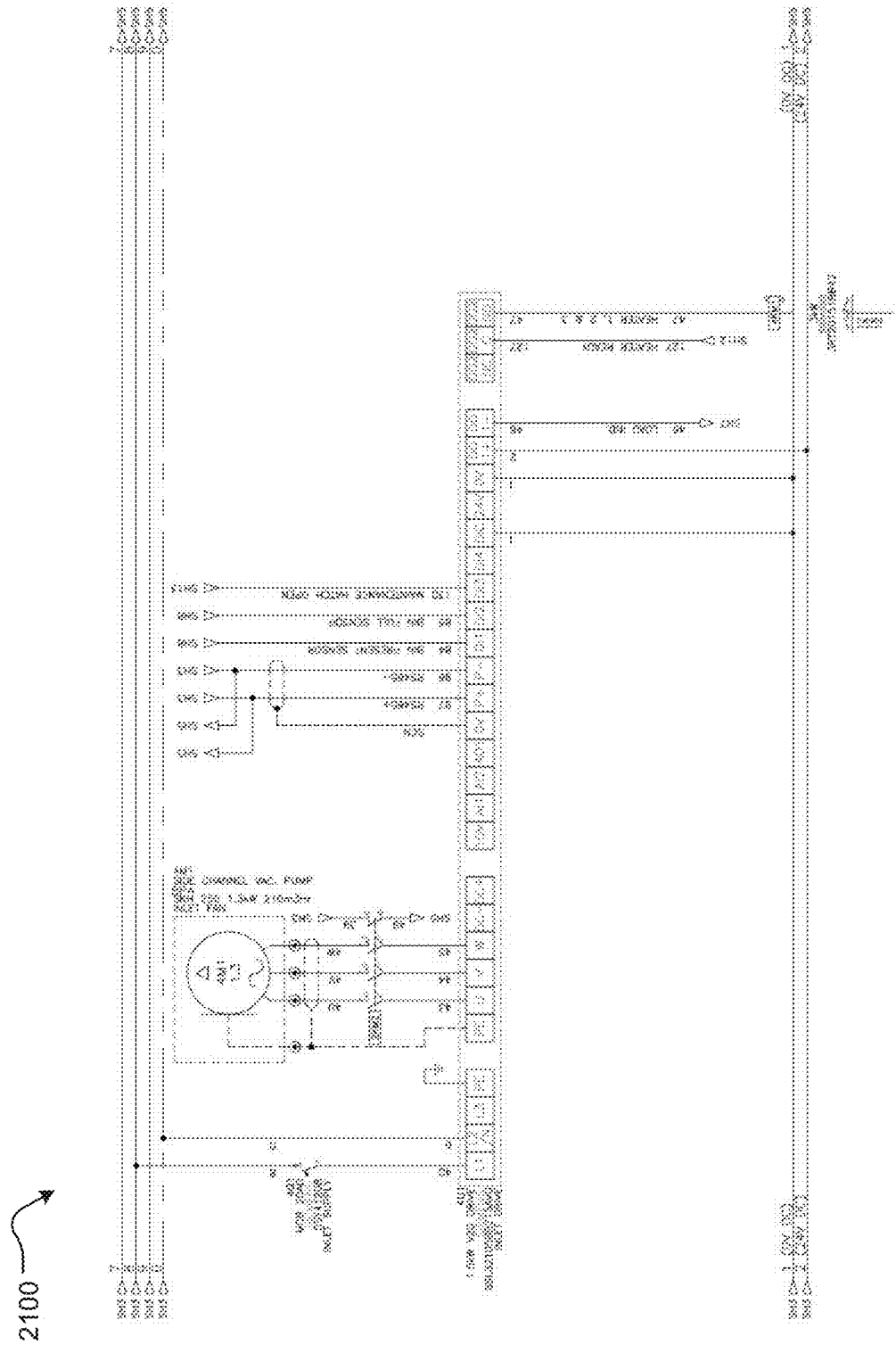
FIG. 21 is an electrical schematic diagram of an inlet fan drive circuit within the waste processing machine.

FIG. 21 is an electrical schematic 2100 illustrating an inlet drive circuit within the waste processing system 110 according to some embodiments. The inlet drive circuit provides an electrical driving and control mechanism for the various motors driving the inlet actuator arm within the waste processing system 110.

Figure 22:
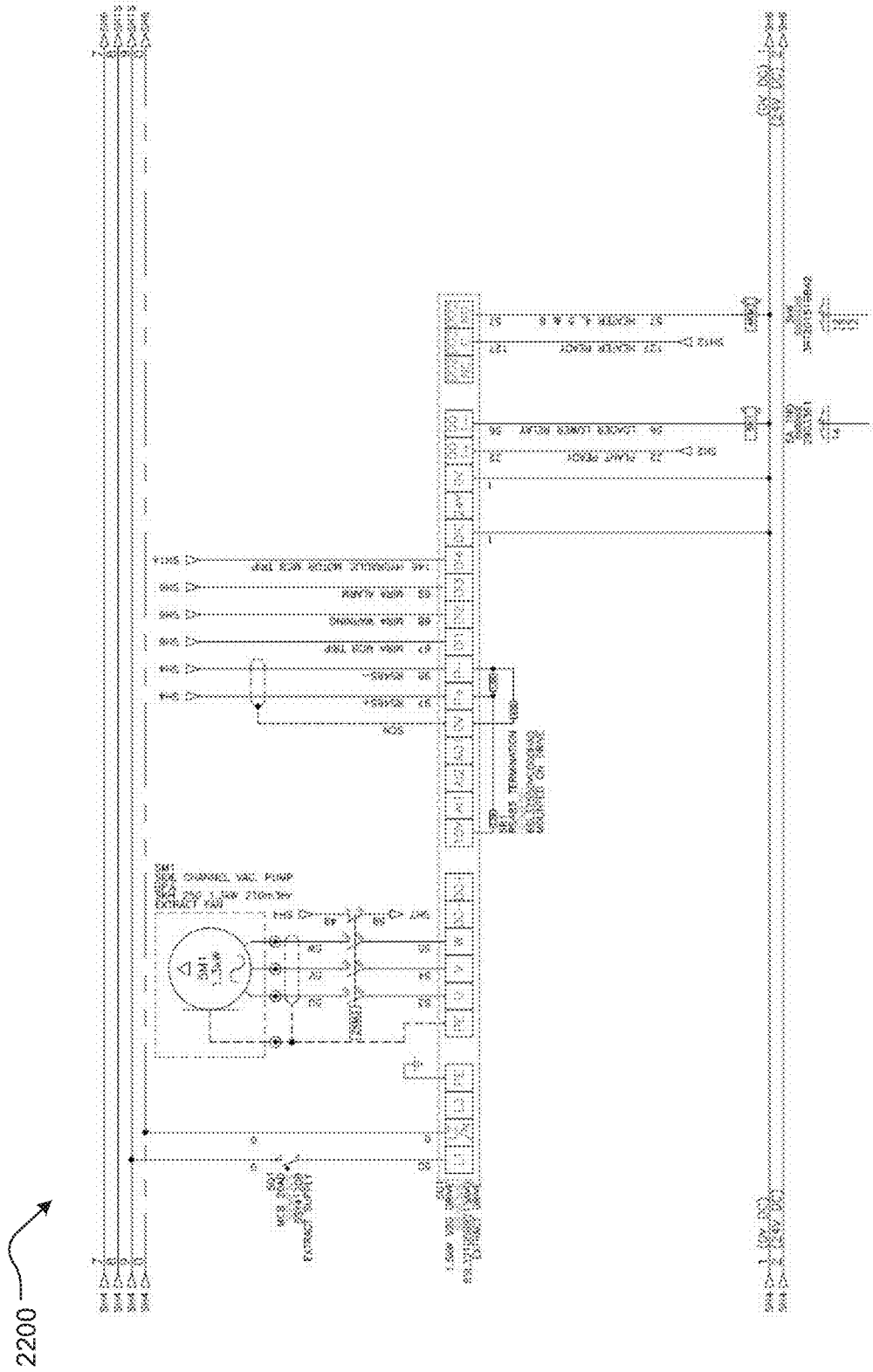
FIG. 22 is an electrical schematic diagram of an outlet fan drive circuit within the waste processing machine.

FIG. 22 is an electrical schematic 2200 illustrating an outlet drive circuit within the waste processing system 110 according to some embodiments. The outlet drive circuit provides an electrical driving and control mechanism for the various motors driving the outlet actuator arm within the waste processing system 110.

Figure 23:
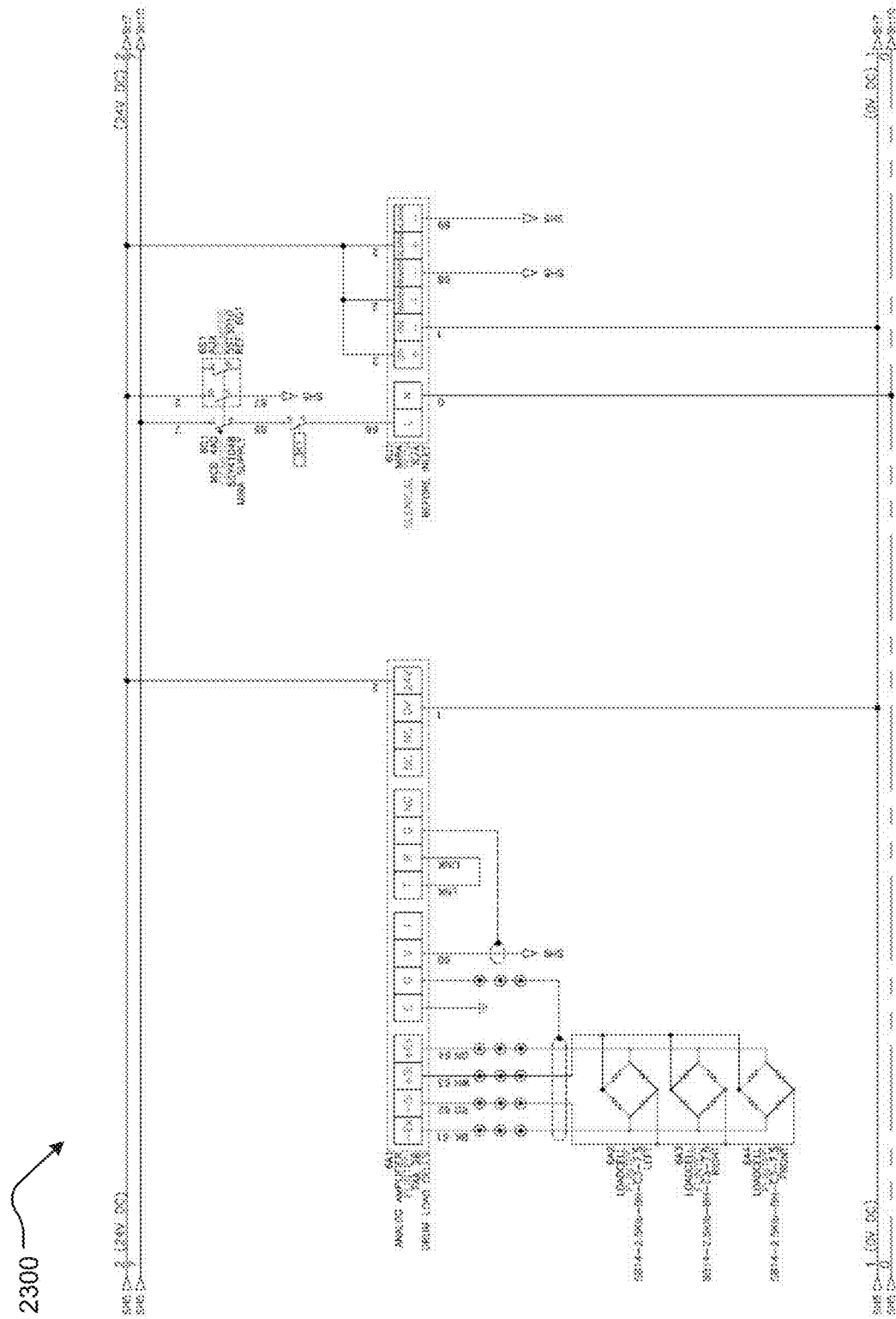
FIG. 23 is an electrical schematic diagram of a circuit providing power to an ioniser and load cells within the waste processing machine.
Figure 24:
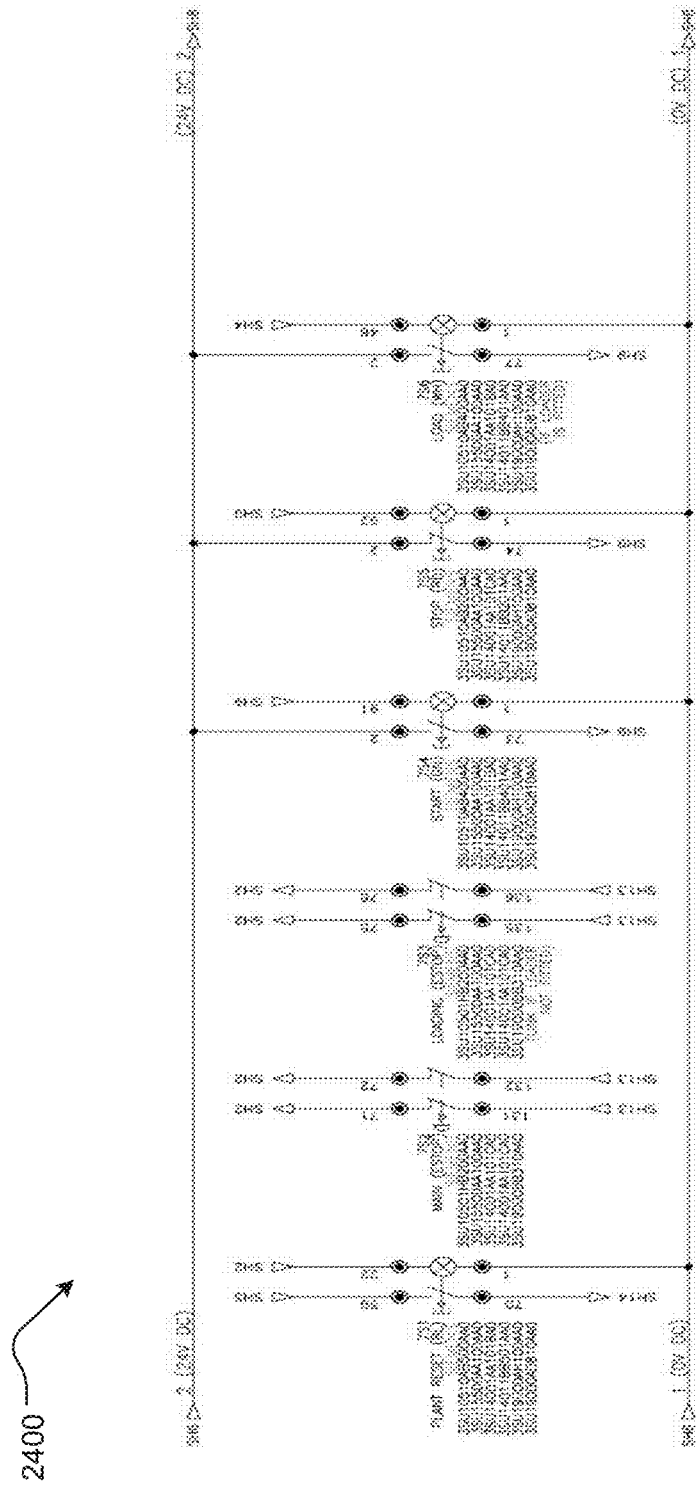
FIG. 24 is an electrical schematic diagram of an electrical circuit for machine push buttons on the waste processing machine.

FIG. 23 is an electrical schematic 2300 illustrating a circuit providing power to the ioniser and three load cells within the drum 230. FIG. 24 is an electrical schematic 2400 illustrating an electrical circuit behind the 6 machine push buttons on the waste processing machine 110. The push buttons include: a reset button, an emergency stop button, a loading emergency stop button, a start button, a stop button and a loading button.

Figure 25:
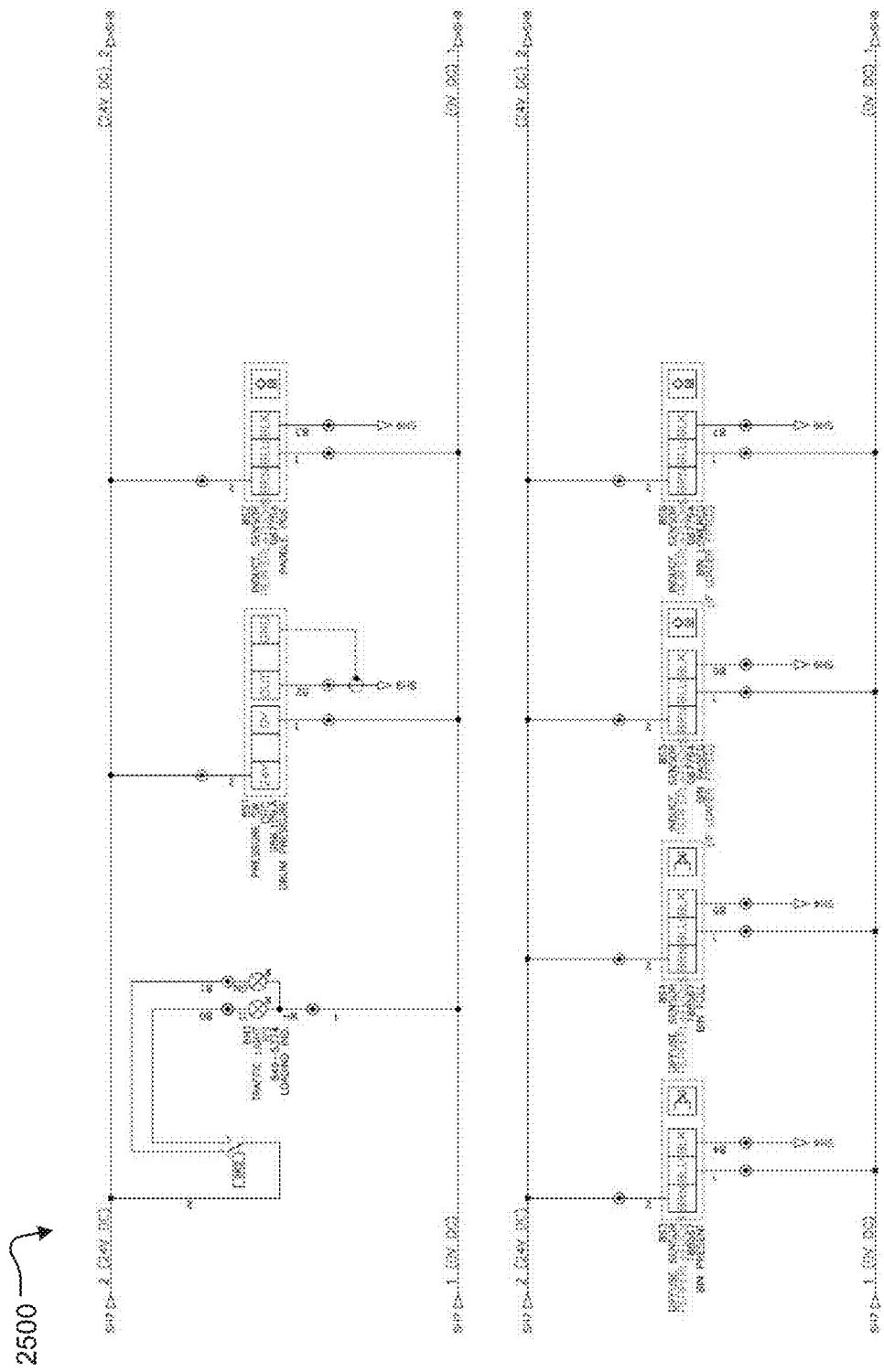
FIG. 25 is an electrical schematic diagram of an electrical circuit for sensors within the waste processing machine.

FIG. 25 is an electrical schematic 2500 illustrating an electrical circuit connecting the various sensors within the waste processing system 110. The various sensors include: waste loading bin proximity sensor, drum pressure sensor, paddle position sensor, waste outlet bin proximity sensor, waste outlet bin capacity sensor, waste loading arm position sensors and other relevant sensors in other embodiments.

In some embodiments, the sensors of the system comprise inlet air temperature sensors, inlet plenum temperature sensors, exhaust air temperature sensors, and drum pressure sensors. In some embodiments, exemplary sensor values expected during operation of the machine 110 may be indicated by the below table.

| Sensor | Expected Range |
|---|---|
| Drum Temperature | Ambient-60° C. |
| Air flow rate | 0-6 metres per minute |
| Air outlet temperature | Ambient-60° C. |
| Air inlet temperature | Ambient-60° C. |
| Drum Pressure | −3 to +3 mBa, target: −0.01 mBa |
| Air plenum temperature | 140° C. to 185° C. |

Figure 26:
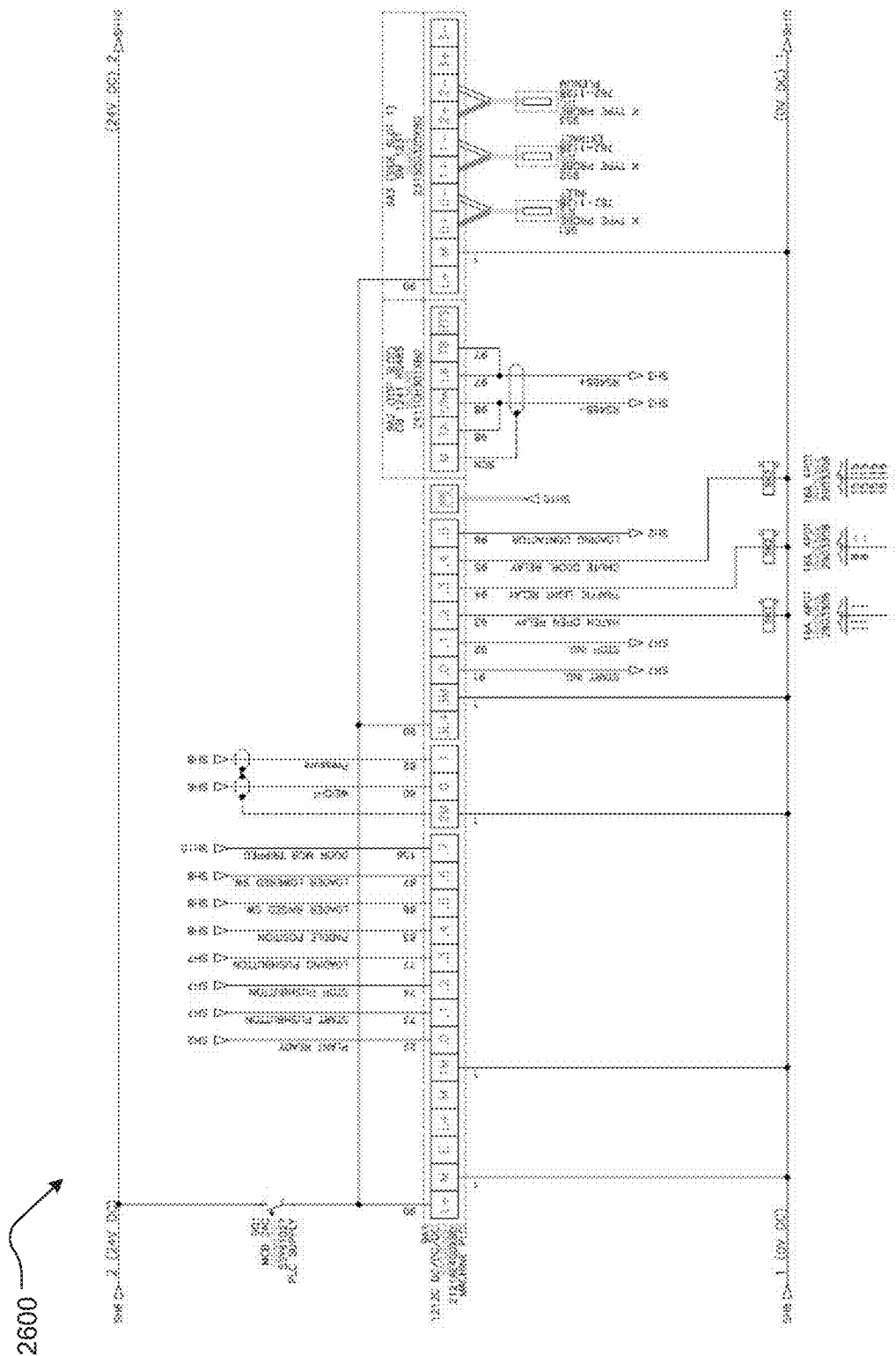
FIG. 26 is an electrical schematic diagram of an electrical circuit connecting a waste processing controller to the components of the waste processing machine.
Figure 27:
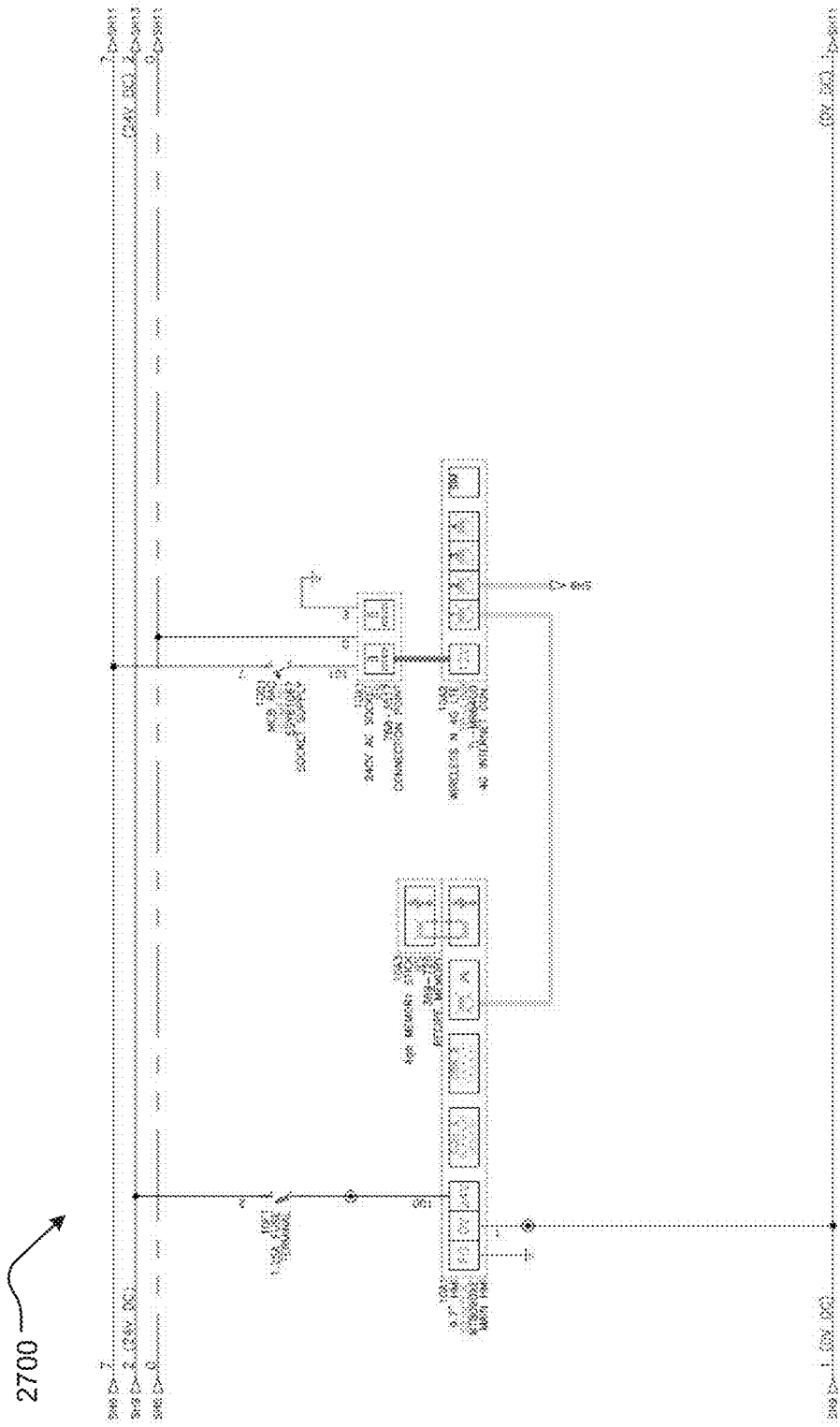
FIG. 27 is an electrical schematic diagram of an electrical circuit connecting the HMI to the components of the waste processing machine.

FIG. 26 is an electrical schematic 2600 illustrating an electrical circuit connecting the controller 210 to the various components of the waste processing machine 110. FIG. 27 is an electrical schematic 2700 illustrating an electrical circuit connecting the HMI 270 to the various components of the waste processing machine 110.

Figure 28:
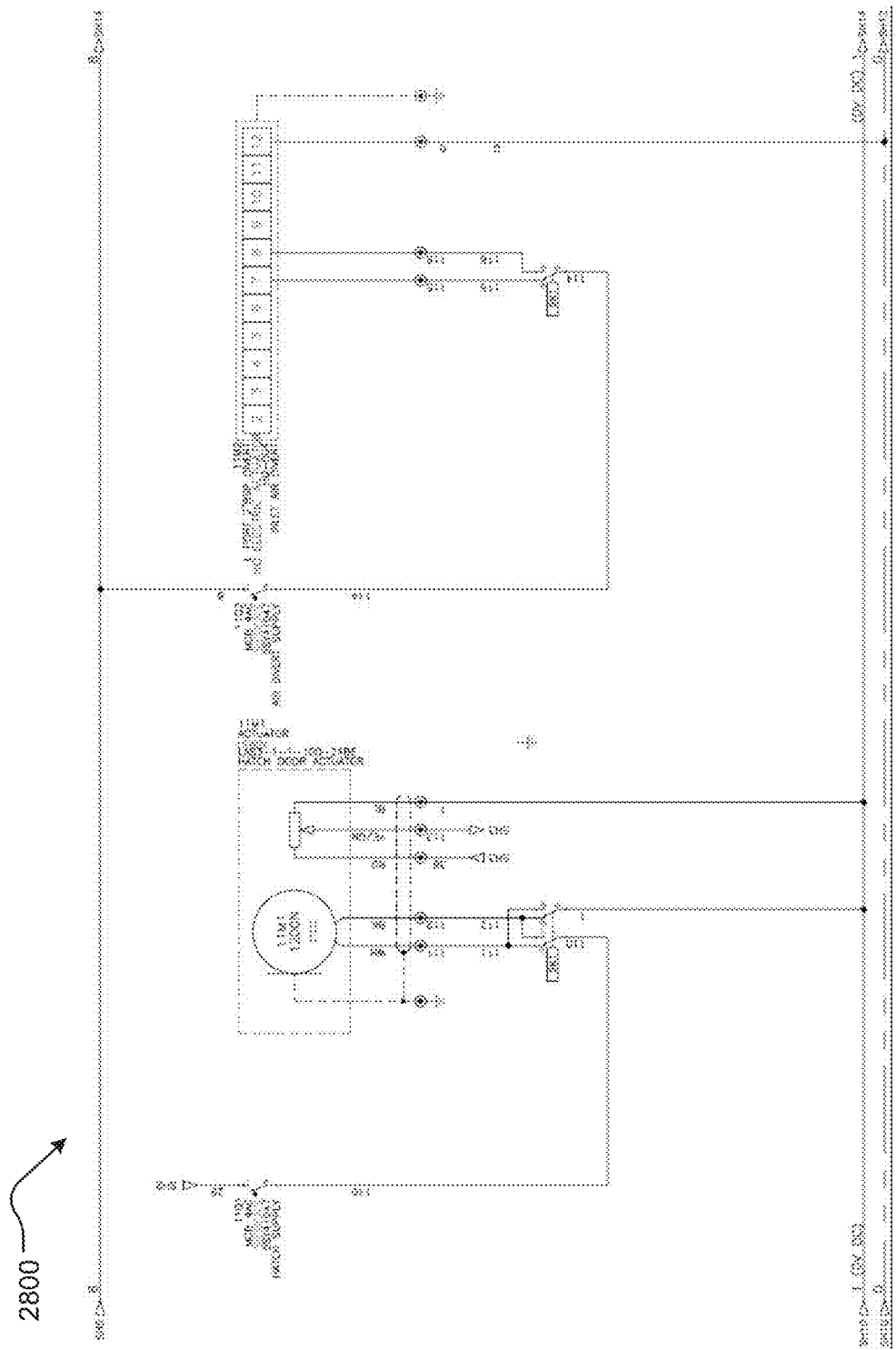
FIG. 28 is an electrical schematic diagram of an electrical circuit connecting the outlet actuator to the power supply and the controller to receive input commands.
Figure 29:
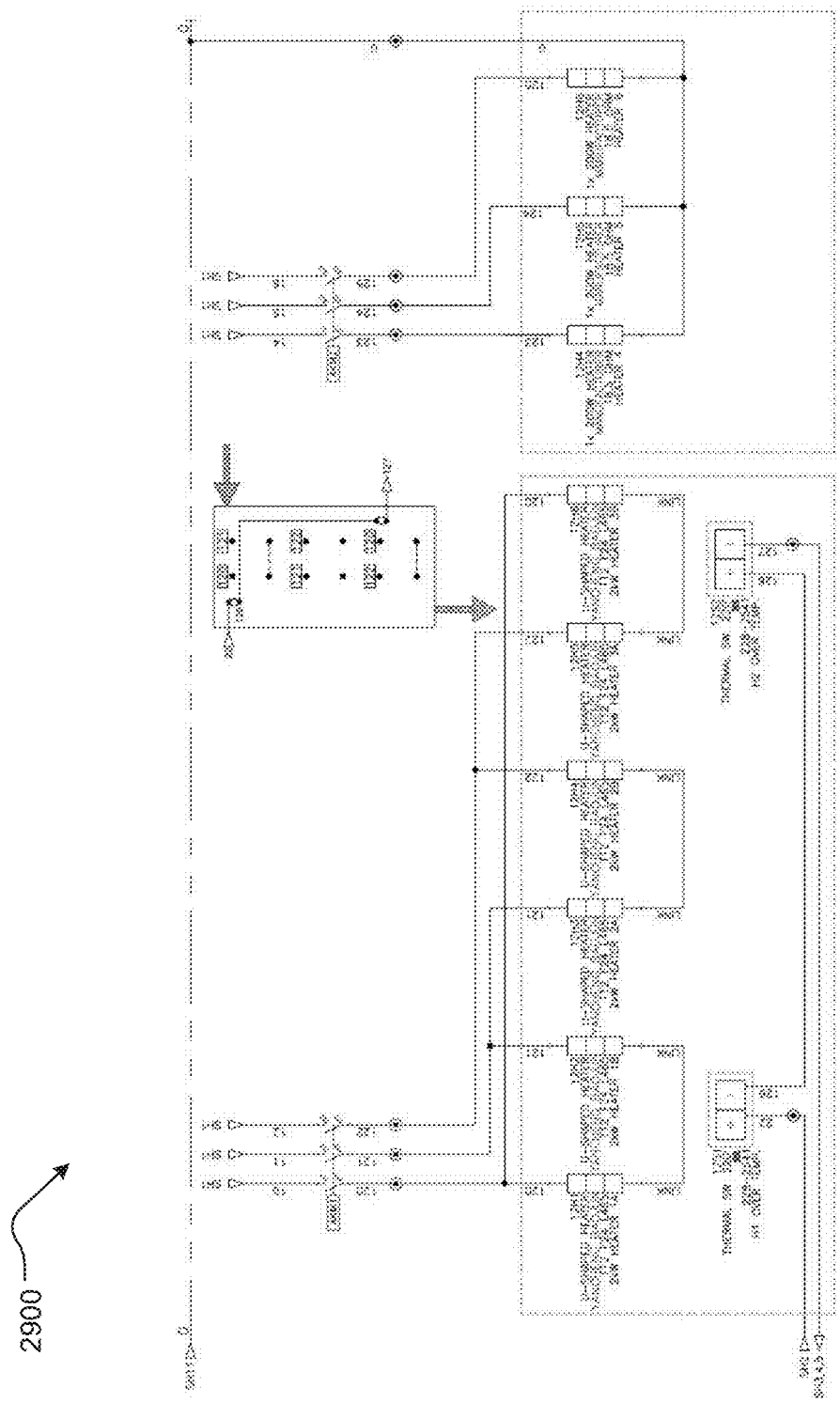
FIG. 29 is an electrical schematic diagram of an electrical circuit connecting the heaters of the air flow system to the power supply and controller.

FIG. 28 is an electrical schematic 2800 illustrating an electrical circuit connecting the outlet actuator to the power supply and the controller 210 to receive input commands FIG. 29 is an electrical schematic 2900 illustrating an electrical circuit connecting the various heaters of the air flow system 220 to the power supply and the controller 210.

Figure 30:
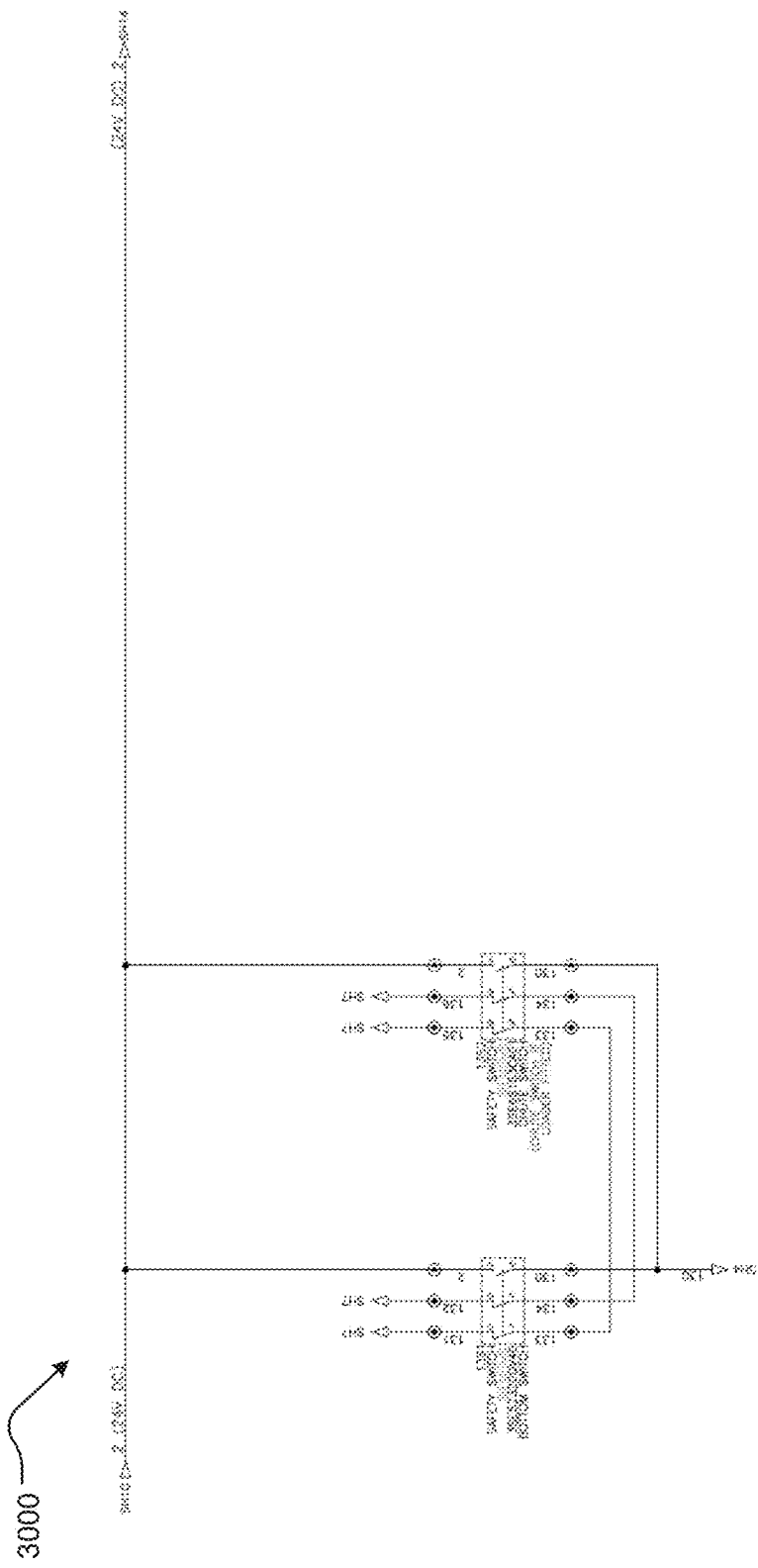
FIG. 30 is an electrical schematic diagram of an electrical circuit connecting the maintenance hatch safety switches to the safety circuit.
Figure 31:
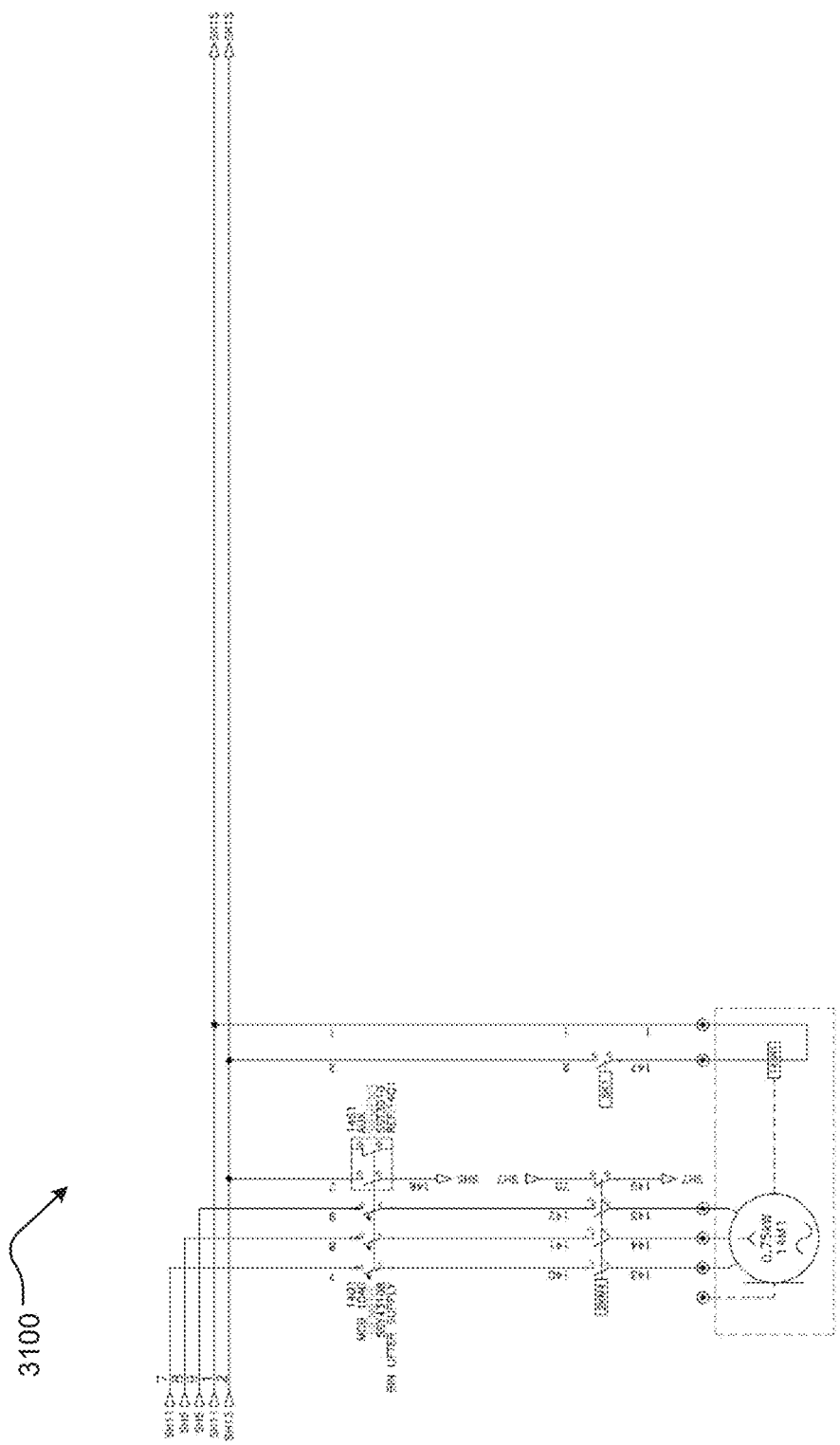
FIG. 31 is an electrical schematic diagram of an electrical circuit connecting the hydraulic motor and solenoid of the waste loader system.
Figure 32:
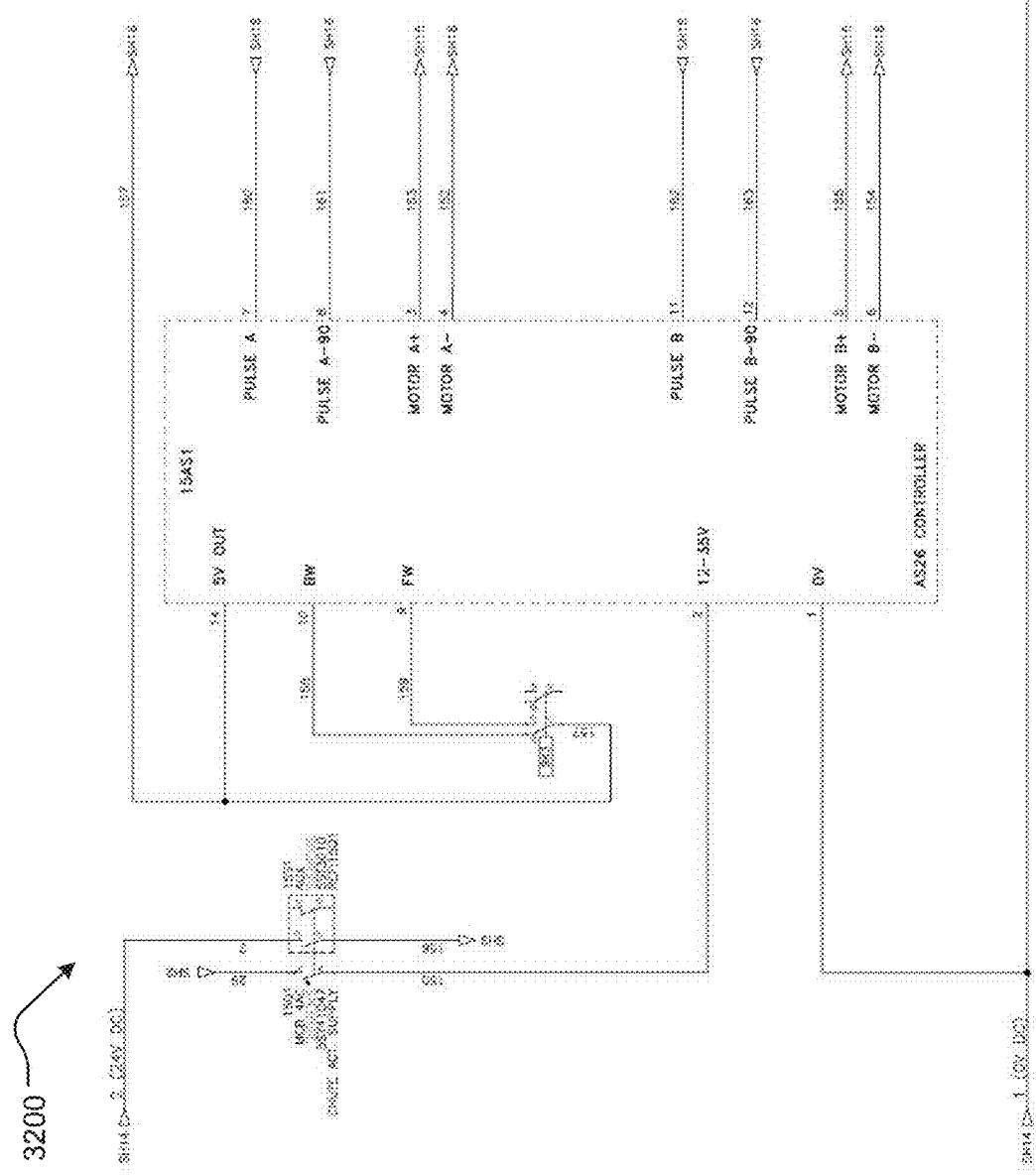
FIG. 32 is an electrical schematic diagram of an electrical circuit connecting an inlet hatch actuator controller of the waste loader system.
Figure 33:
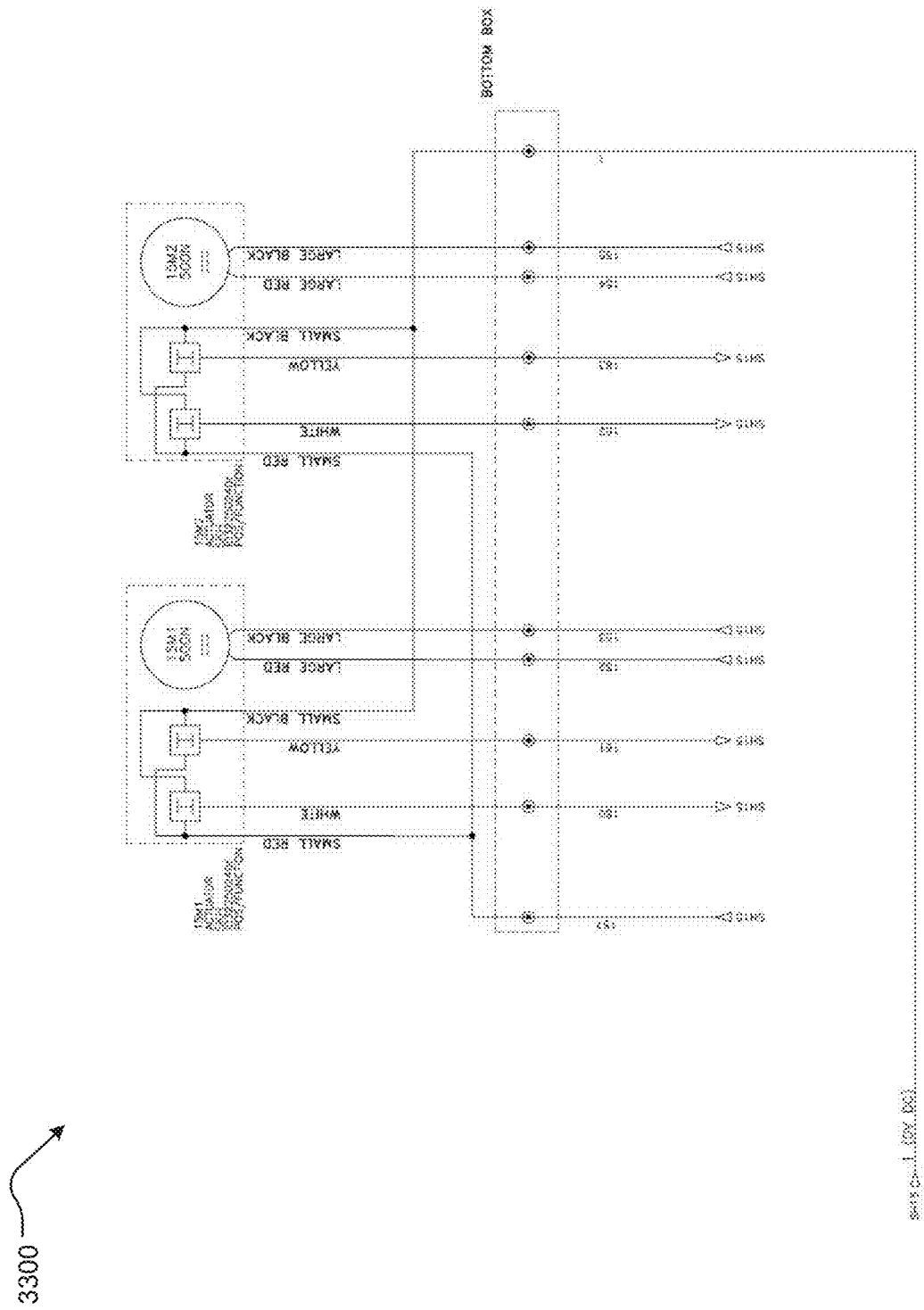
FIG. 33 is an electrical schematic diagram of an electrical circuit connecting an inlet hatch actuator of the waste loader system.

FIG. 30 is an electrical schematic 3000 illustrating an electrical circuit connecting the maintenance hatch safety switches to rest of the safety circuit 1900 of FIG. 19. FIG. 31 is an electrical schematic 3100 illustrating an electrical circuit connecting the hydraulic motor and solenoid of the waste loader system 260. FIG. 32 is an electrical schematic 3200 illustrating an electrical circuit connecting the inlet hatch actuator controller of the waste loader system 260. FIG. 33 is an electrical schematic 3300 illustrating an electrical circuit connecting the inlet hatch actuator of the waste loader system 260.

Figure 35:
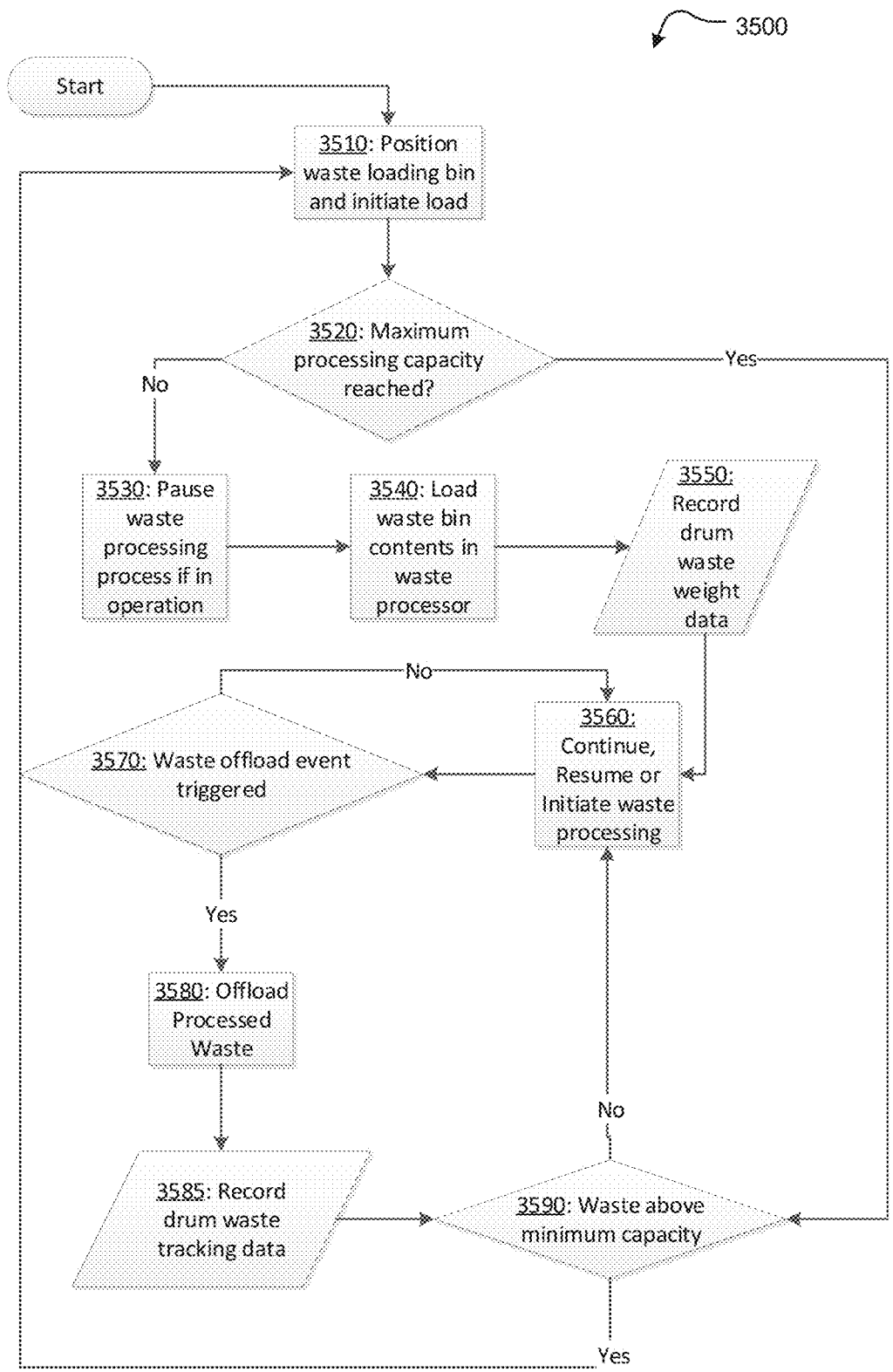
FIG. 35 is a flowchart illustrating a method of operation of the waste processing machine according to some embodiments.

FIG. 35 is a flowchart 3500 of the overall operations of the waste processing machine 110 according to some embodiments. Step 3510 involves positioning of a waste loading bin in the waste loader system 260. A human operator may open the door of the waste loader system 260, positing the waste loading bin inside the loader cage 510 on the bin cradle. After positioning the waste loading bin, the human operator may close the door x and operate the controls of the waste loader system 260 to initiate a deposition of the waste into the drum 230. The initiation also locks the door of the waste loader system 260. In embodiments where the waste bin identity sensor 310 is included, the waste loader system may read any identity on the bin to ascertain identity of a customer associated with the bin. After initiation of the deposition, the waste loader system 260 sends a message to the controller 210 conveying the instruction of loading additional waste and identity of the customer. The message also includes the weight of additional waste to be added to the drum.

At step 3520, the controller 210 assess if the addition of additional waste could be loaded into the drum 230. This assessment is based on a maximum weight loading threshold value for the drum 230. In some embodiments, this maximum weight loading threshold value could be 1000 kg. Other considerations may also be taken into account such as the readiness of the processed waste for disposal or dispensing from the drum. If the waste present in the drum is close to a state wherein it can be dispensed, the controller may delay the addition of additional waste until the waste present in the drum is dispensed. If for any of the reasons described above, the drum 230 is not capable of taking in more waste, control passes on to step 3590 where the controller 210 assess if the weight of the waste in the drum 230 is above a minimum capacity. If weight of the waste in the drum 230 is above a minimum capacity, control passes on to step 3560 wherein the waste processing machine 110 resumes or continues its operation. On the other hand, if the drum 230 is capable of taking in more waste, the control passes on to step 3530.

At step 3530, the operation of the drum 230 and the waste processing mixer 1400 is paused, the inlet hatch 1710 is opened and the waste loader system 260 receives instructions from the controller 210 to lift the waste loading bin and tip out its contents into the drum 230 at step 3540. At step 3550, updated weight of the contents of the drum 230 is ascertained through the load cells and stored by the controller. The updated weight with the time associated with the actual loading of the waste may also be transmitted to the Control and Monitoring Server 150. The system server 150 may store such information in the database 160. After the weight data recording step of 3550, the waste processing machine 110 will continue, or initiate the processing of the waste at step 3560. The processing the waste continues until a waste offload event is triggered at step 3570. Flowchart 36 illustrates the details of the criterion and steps involved in generation of a waste offload trigger.

Figure 36:
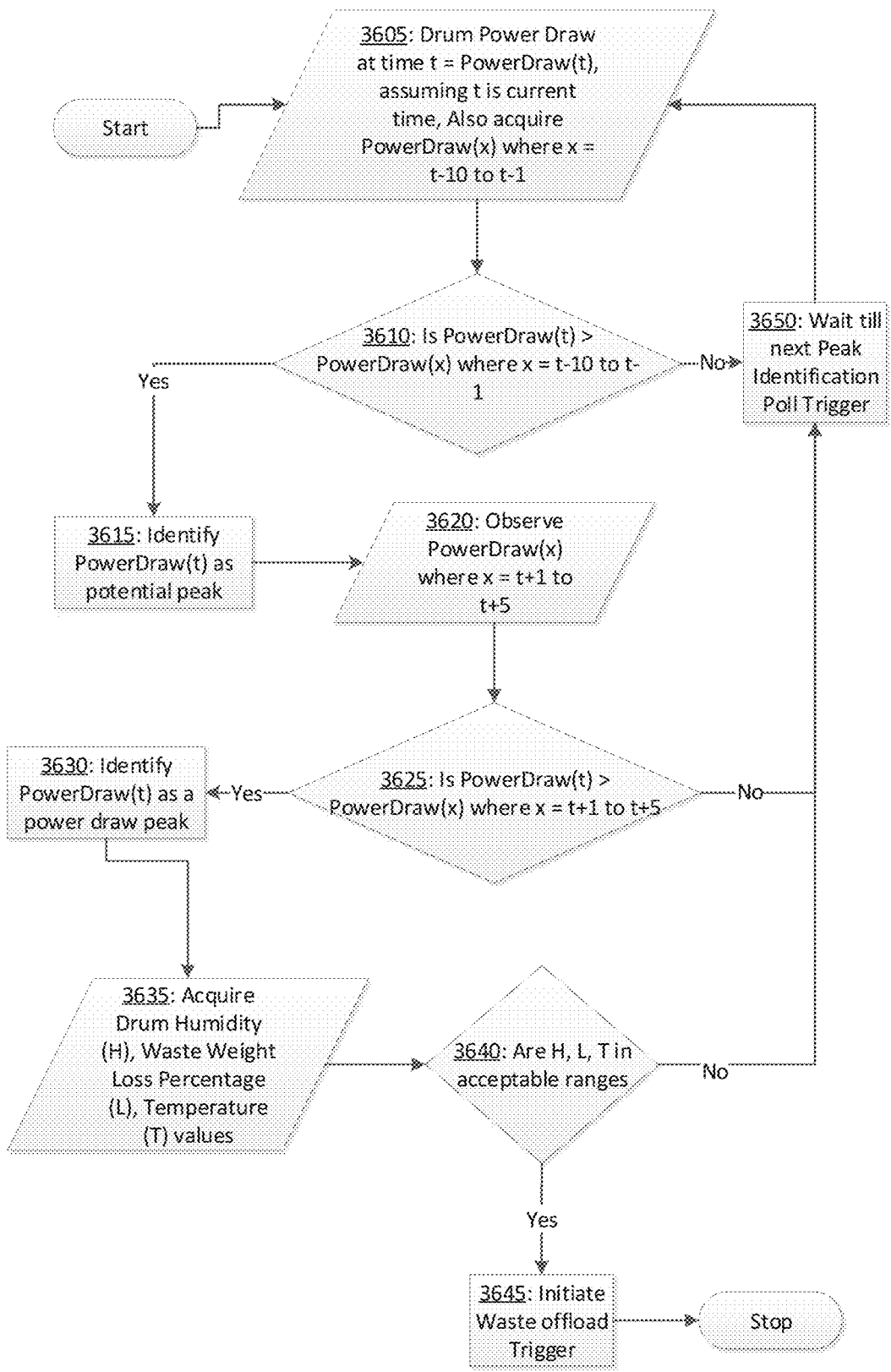
FIG. 36 is a flowchart illustrating a process of identification of a waste offload trigger according to some embodiments.

After a waste offload trigger is generated according to the flowchart of FIG. 36, then offloading of processed waste is initiated at step 3580. Following the completion of offloading of processed waste, at step 3585, the weight of the contents of the drum is ascertained and recorded in a manner similar to step 3550. At step 3590, the ascertained weight of the contents of the drum is compared with a minimum threshold capacity. If the weigh falls below the minimum capacity, controls passes back to step 3510 and the Waste processing machine 110 awaits supply for waste to continue its operation. In some embodiments the minimum weight threshold value may be 50 kg.

FIG. 36 is a flowchart illustrating the process of identification of a waste offload trigger referred to in the flowchart of FIG. 35 at step 3570. The assessment of whether the waste in the drum 230 is sufficiently processed to dispose depends on several physical attributes of the processed waste. Waste suitable for disposal should have a substantially reduced moisture content. The reduced moisture content allows the long term storage of the processed waste while reducing the risks of attracting vermin or the growth or mould or further decomposition that may produce foul gases. Reduction in moisture content also reduces the overall weight and volume of the processed waste making storage and transportation for final disposal more energy efficient.

In some embodiments, the maximum power draw by the motor 240 may be used as an indicator of the extent to which the waste in the drum 230 is processed. The power drawn by the motor 240 depends on the level of resistance faced by the waste processing mixer 1400. After waste is loaded in the drum 230, the waste processing mixer 1400 initiates the mixing action. As the contents of the waste are mixed, they acquire a thicker and more viscous character with the release of moisture due to the mixing action. As the mixing action continues, the air flow through the waste enhances the evaporation of moisture from the waste. As moisture from the waste is lost through evaporation, the resistance to the waste processing mixer 1400 reduces. This initial increase in resistance due to a release of moisture followed by a subsequent decrease in resistance due to the loss of moisture forms one basis of assessment of readiness of disposal of processed waste in some embodiments. The assessment of readiness of disposal of processed waste may also be aided by other sensor data such as drum humidity, weight of the waste in the drum, temperature of the waste in the drum and other relevant sensor data about the waste.

At step 3605, the power drawn by the drum 230 at time t and times t−10 to t−1 are acquired by the controller 210. At step 3610, the controller 210 assess if the power drawn at time t was greater than the power drawn at any time between t−10 to t−1. Step 3610 is essentially a backward looking peak assessment over the range t−10 to t. If the power drawn at time t is found to be less than the power drawn at any time between times t−10 to t−1, the controller 210 infers that the power draw at time t is not a potential peak and control passes on to step 3650. At step 3650, the controller 210 waits for a next polling trigger event to return to step 3605 and attempt identification of another peak.

If control passes on to step 3615, the power draw at time t is identified as a potential peak by the controller 210. Subsequently, control passes on to step 3620 wherein the controller 210 observes and records power draw over the time periods t+1 to t+5. At step 3625, the power draw at time t is compared with the power draw at times t+1 to t+5. Step 3625 is essentially a forward looking peak inquiry. If power draw at any points between time t+1 to t+5 is observed to be greater than the power draw at time t, the controller 210 infers that the power draw at time t is not a peak and control returns to step 3650. However, of the power draw at all times between time t+1 to time t+5, then control passes on to step 3630 and the power draw at time t is identified by the controller at time 210 as a peak. After step 3630, at step 3635, the controller 210 acquires addition drum 230 sensor values such as humidity, the percentage of weight lost in the drum 230 since the last input, drum temperature, air flow rate, air outlet temperature, air inlet temperature, pressure within the drum and any other relevant sensor data. At step 3640 the acquired sensor data is checked for incidence within acceptable ranges and if this is the case, the controller 210 initiates a waste offload trigger at step 3645. On the other hand, if any or a certain number of the acquired parameters are not within acceptable ranges, then control may pass back to step 3650.

The generation of a waste offload trigger by the controller 210 may not immediately trigger the offloading of processed waste. The waste offload trigger is used by the controller 210 as a timing mechanism to initiate an offload after a certain period of time. Since a peak in power draw by the drum 230 indicates an inflection point from a moisture heavy drum contents with higher resistance and viscosity towards a dryer and lighter processed waste; the controller 210 awaits the passage of a certain amount of waiting period before initiating an actual offload. The waiting period is equivalent to a tail associated with the drum power draw peak. In some embodiments, the waiting period may be set to 5 hours. In other embodiments, this waiting period may be between 4 hours to 6 hours. In other embodiments, the waiting period may be a function of the initial weight of the waste in the drum 230 or the moisture content of the initial weight of the waste in the drum 230.

In certain embodiments where the waste processing machine 110 is used for processing only a specific type of waste, for example fish carcass waste from a fish processing plant, the waiting period may be specifically calibrated for the specific type of waste. The calibration may be based on the moisture content, weight, approximate density and any other relevant attributes of the specific type of waste. In some embodiments, the time range across which the power drawn by the motor 240 at steps 3610 and 3625 is analysed, may be calibrated to best suit the nature of the waste being processed. For example, at step 3610, the backward looking inquiry of power drawn by the drum may extend to 20 minutes and likewise the forward looking inquiry at step 3625 may extend to 10 minutes. In other embodiments, the backward and forward looking inquiry ranges of steps 3610 and 3625 may take into account time ranges of 30 minutes and 20 minutes respectively.

Figure 37:
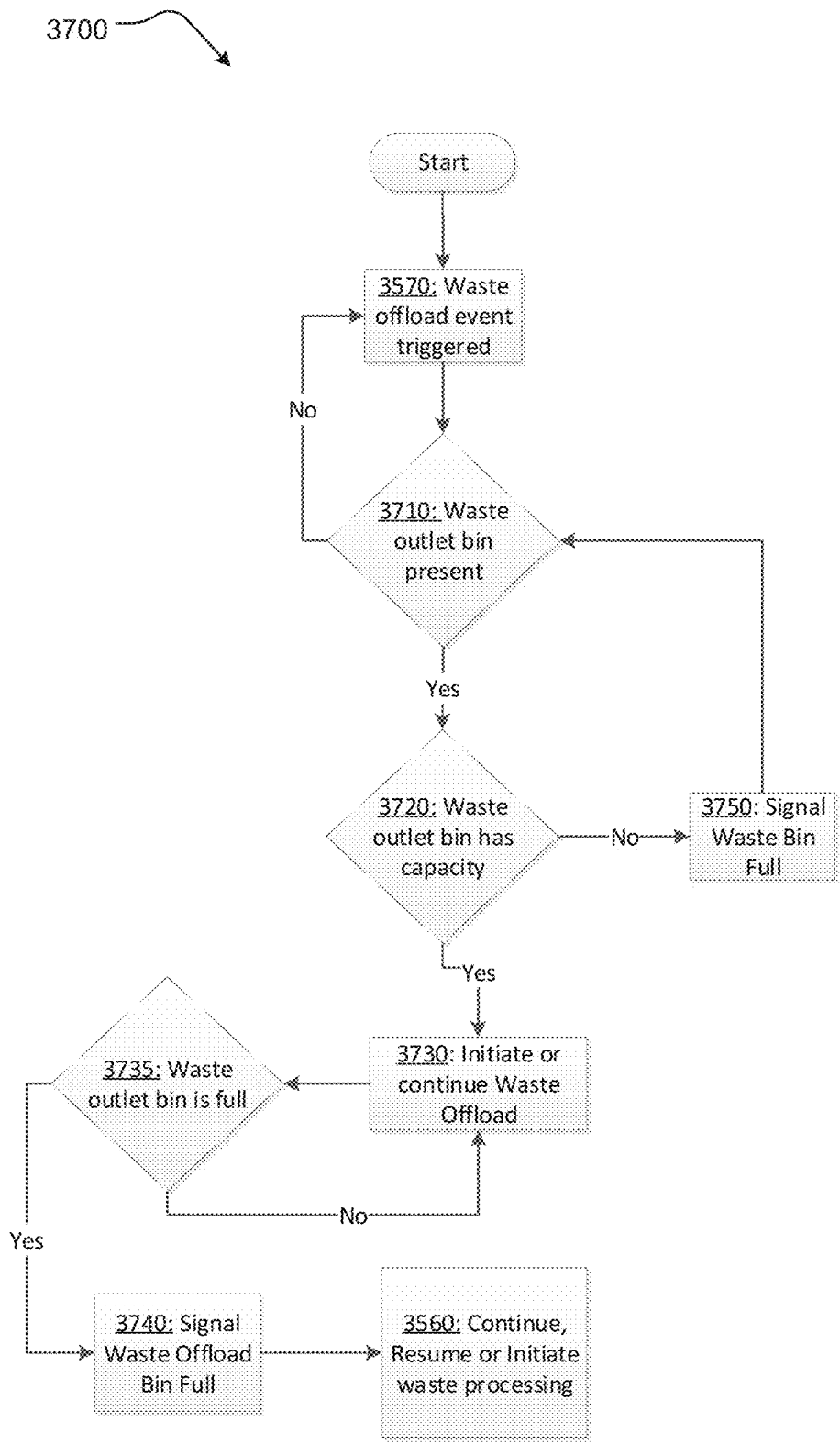
FIG. 37 is a flowchart of a waste offloading process according to some embodiments.

FIG. 37 illustrates a flowchart 3700 that provides a logical flow for the Waste offloading process initiated at step 3580 of flowchart 3500. After the waste offload process is initiated, the controller 210 checks the output signal of the bin proximity sensor 950 to determine the presence or absence of a processed waste collection bin 3405 in position to collect the processed waste. If a processed waste collection bin is not determined to be in place under the outlet chute, control passes back to step 3570 and the controller 210 awaits placement of an empty waste outlet bin 3405 at step 3710. If at step 3720, it is determined that the waste outlet bin has capacity to take in more waste, then the controller 210 instructs the waste scooping mechanism to initiate the offloading of waste through the outlet hatch. However, if at step 3720, it is determined that the waste outlet bin is full, then control passes on to step 3750. At step 3750, the controller 210 generates a signal indicating that the waste outlet bin is full. Controller 210 may communicate the generated signal to a particular client device 140. Upon receiving the signal regarding a full waste bin through the client device 140, an operator or user may initiate the removal of the full waste bin and its replacement with an empty waste bin, for example.

As processed waste is offloaded at step 3730, intermittently the bin depth sensor 840 checks if the waste outlet bin is full at step 3735. If the result of the check at 3735 is that the waste outlet bin is determined to be full, then at 3740 the controller 210 signals that the waste offload bin 3405 is full and subsequently control passes back to step 3560 of flowchart 3500. If the waste outlet bin is determined by controller 210 to not be full, the waste offloading process resumes at step 3730.

Figure 38:
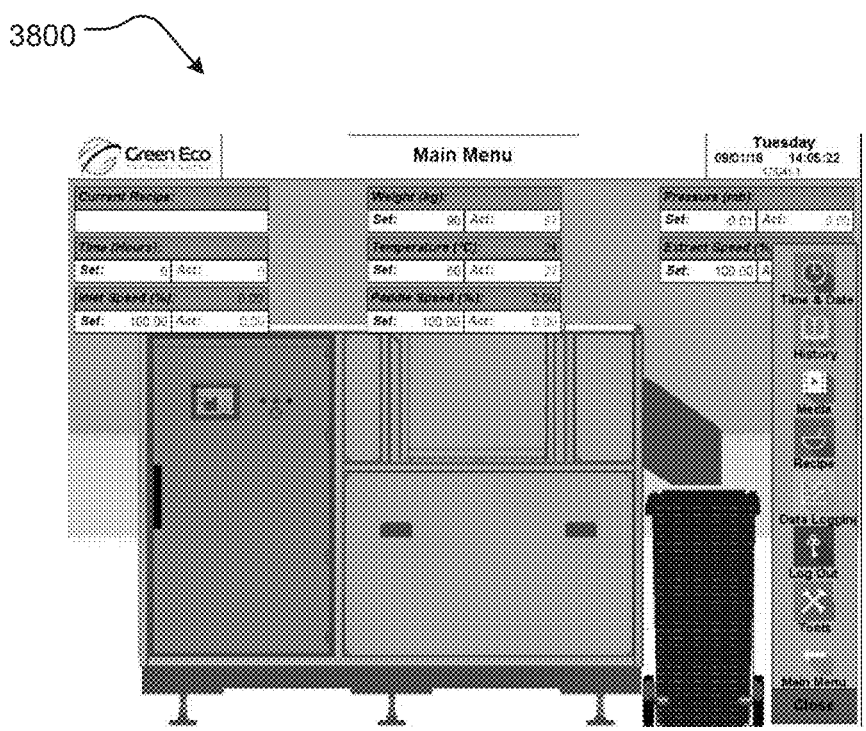
FIG. 38 is a screenshot of an example user interface display image illustrating a main menu with navigation options and a display of various sensor data monitored by the controller of a waste processing machine according to some embodiments.
Figure 39:
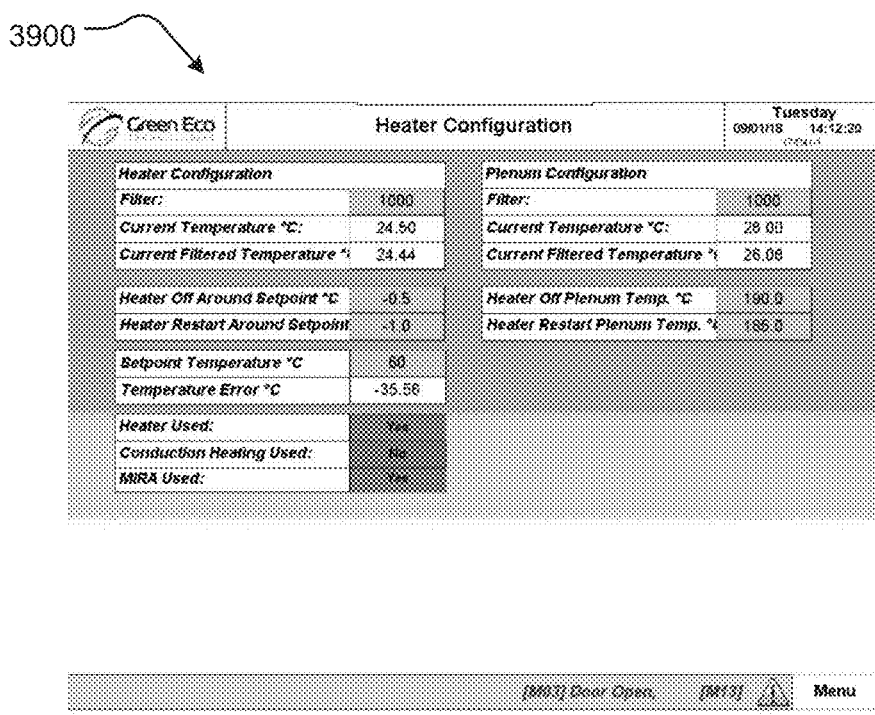
FIG. 39 is a screenshot of an example user interface display image of a configuration menu for heaters in the air flow system.

FIG. 38 is an example screenshot 3800 of a display of the HMI 270 illustrating a main menu with some navigation options and a display of various sensor data monitored by the controller 210. FIG. 39 is an example screenshot 3900 of the configuration menu for heaters in the air flow system 220. The heater configuration menu allows the turning on and off of the heaters, setting of a target temperature or set-point temperature to heat the air to. The actual temperature of the air through the heater may not reach the target temperature. The heater configuration menu also allows setting cut-off temperatures to turn the heater off and restart the heater again. For example, the screenshot 3900 illustrates that the target or set-point temperature has been set to 60° C. while the heater cut-off temperature has been set to 59.5° C. (−0.5) and heater restart temperature has been set to 59° C. (−1).

Figure 40:
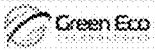
FIG. 40 is a screenshot of an example user interface display image of an unload configuration menu.

FIG. 40 is an example screenshot 4000 of a display of the HMI 270 illustrating an unload configuration menu. The unload configuration menu allows the configuration of the speed at with the residue scoop operates, the speed of the unload fan, and allows the bypassing of the waste offload bin present sensor and the waste offload bin full sensor.

Figure 41:
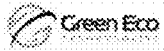
FIG. 41 is a screenshot of an example user interface display image of a loader configuration menu.

FIG. 41 is an example screenshot 4100 of a display of the HMI 270 illustrating an loader configuration menu. The loader configuration menu comprises buttons that manually allows the raising and lowering of a waste bin and the opening and closing of the inlet hatch. The loader configuration menu also allows the variation of the speed of the mixing blade movement during the loading process, the delay between the manual instruction of loading and actual loading, and other relevant configurations.

Figure 42:
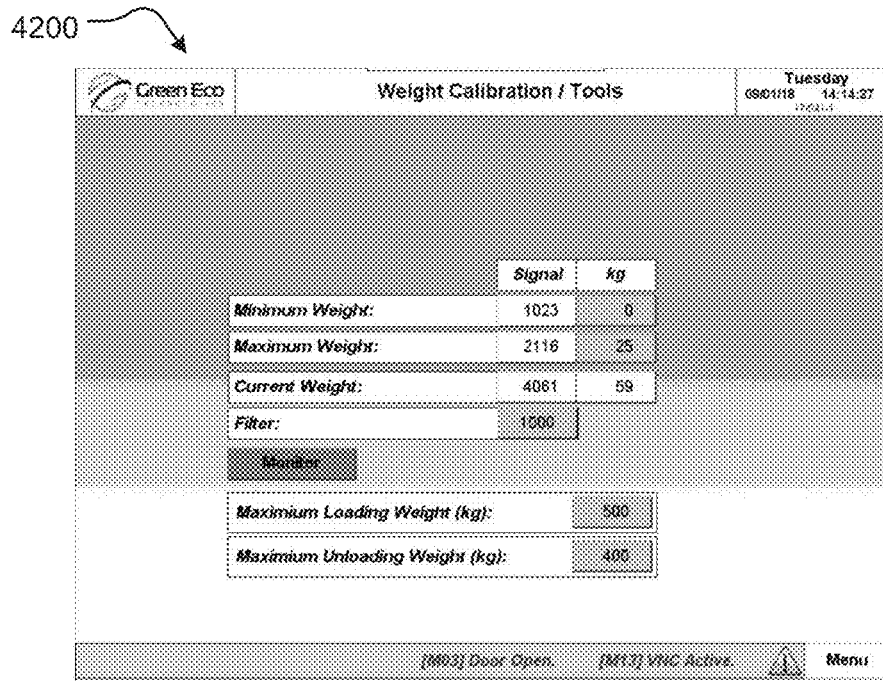
FIG. 42 is a screenshot of an example user interface display image of a weight calibration menu.

FIG. 42 is an example screenshot 4200 of a display of the HMI 270 illustrating a weight calibration menu. The weight calibration menu allows an operator to configure the minimum and maximum loading weights of the waste processing machine 110. The weight calibration menu also displays the current weight of the contents of the drum 230.

Figure 43:
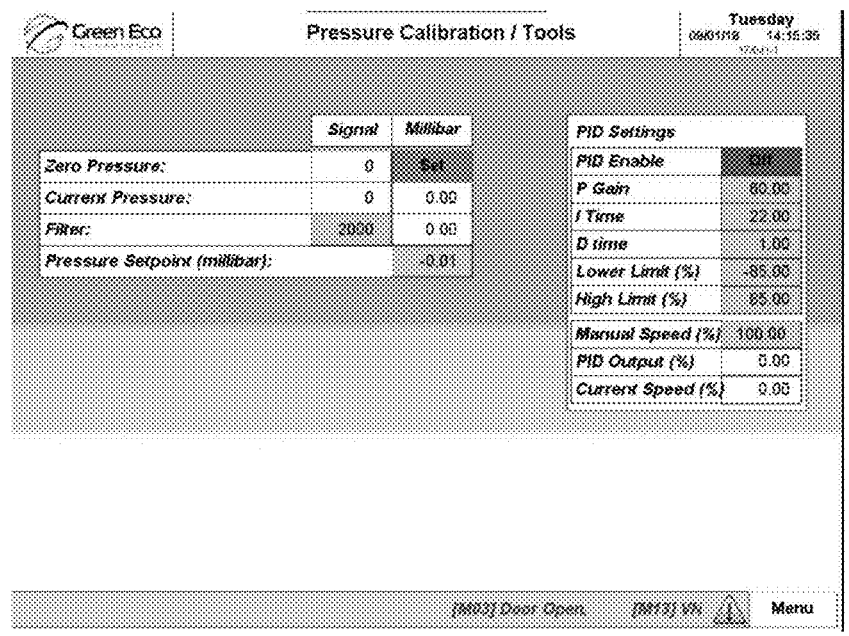
FIG. 43 is a screenshot of an example user interface display image of a pressure calibration menu.

FIG. 43 is an example screenshot 4300 of a display of the HMI 270 illustrating a pressure calibration menu. The pressure calibration menu allows the configuration of a pressure set-point for the air pressure within the drum 230. Based on the pressure configuration, the controller may vary the operation of the air flow system to attempt to attain a certain air pressure within the drum 230.

Figure 44:
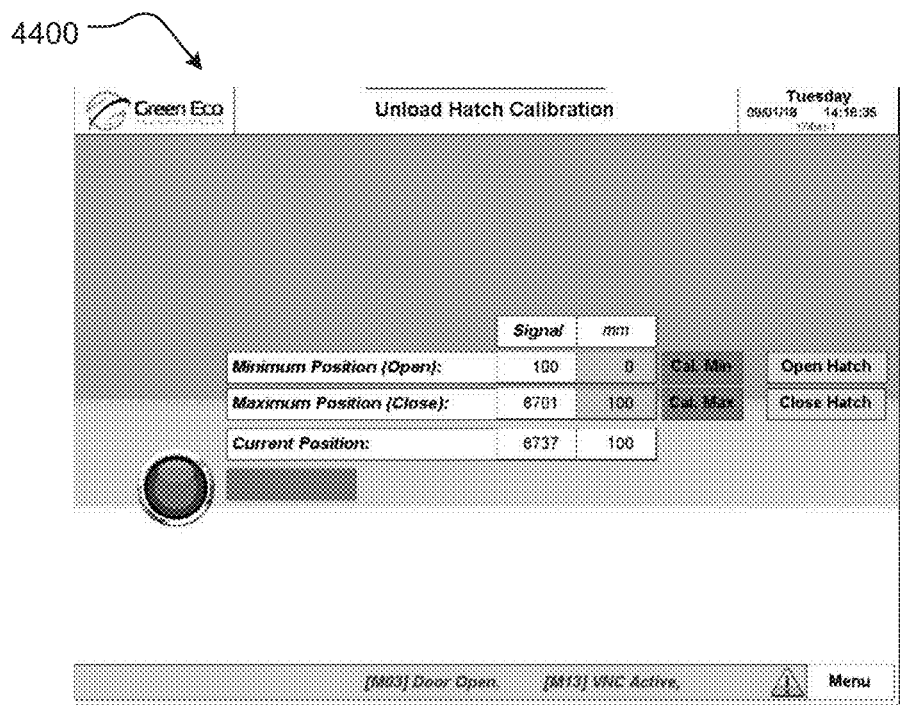
FIG. 44 is a screenshot of an example user interface display image of an unload hatch configuration menu.
Figure 45:
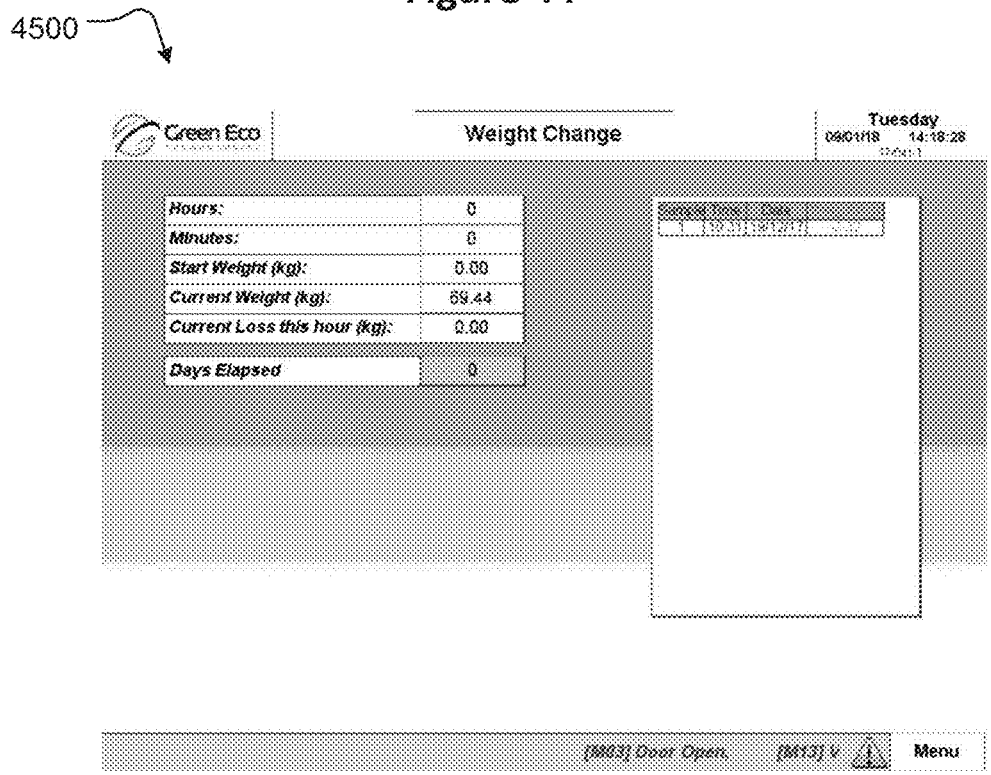
FIG. 45 is a screenshot of an example user interface display image of a weight change display menu.
Figure 46:
FIG. 46 is a screenshot of an example user interface display image of a power consumption display of the various components of the waste processing machine.

FIG. 44 is an example screenshot 4400 of a display of the HMI 270 illustrating a unload hatch configuration menu. The unload hatch configuration menu allows an operator to configure the maximum and minimum operating positions of the outlet hatch. The unload hatch configuration menu also allows the manual opening and closing of the outlet hatch. FIG. 45 is an example screenshot 4500 of a display of the HMI 270 illustrating a weight change display menu. This menu illustrates the change in the weight of waste as it is processed over time. FIG. 46 is an example screenshot 4600 of a display of the HMI 270 illustrating a power consumption display of the various components of the waste processing machine 110.

Figure 47:
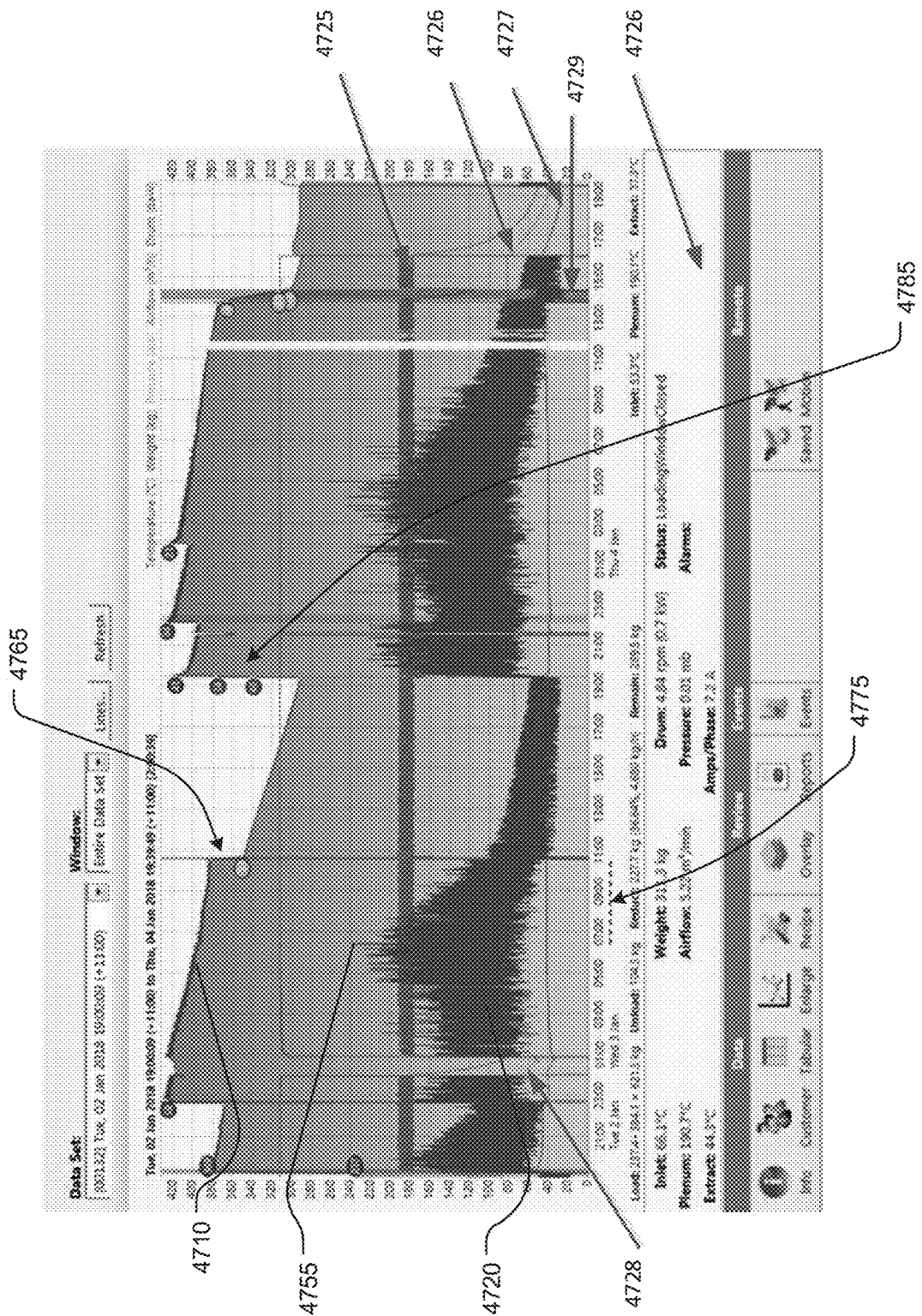
FIG. 47 is a screenshot of an example user interface display image of a graphical display illustrating recorded current and historical operational parameters of the waste processing machine over at least one processing cycle.

FIG. 47 is an example screenshot of the HMI 270 or an application executing on a client computing device 140, showing a plot over time of various operational parameters of the waste processing machine 110 according to the processes described in relation to FIGS. 36 and 37. The x-axis of the plot represents time while the y-axis of the graph represents multiple sensor measurement from a single waste processing machine 110 by way of various distinct plots. The plotted line indicated by reference numeral 4710 represents measured weight of waste in the drum 230 and the plotted line indicated by reference numeral 4720 represents calculated or measured drum power draw over time. Point 4755 on plotted line 4720 is an example of a peak in the measured drum power draw plot 4720. When the peak at point 4755 is detected by the controller 210 according to the process described in relation to FIG. 36, the controller 210 would have generated a waste offload trigger event and the relevant waiting period would have commenced. In some embodiments, the relevant waiting period may be a fixed time period. In other embodiments, the relevant waiting period may be a function of other parameters or operating conditions such as the capacity of the drum, the actual weight of the waste loaded before commencement of operations, the temperature maintained during operations, nature of waste loaded and any other relevant criterion. The time period indicated by reference numeral 4775 is the relevant waiting period associated with the peak 4755. In the illustrated example, the waiting period is roughly equivalent to 4 hours. However, in other embodiments, the waiting period may be a selected period in the range of about 4 hours to about 12 hours, such as about 4 to 7 hours or about 5 to 6 hours, for example. In further embodiments, the waiting period may be a selected period in the range between about 6 and 12 hours, such as about 8 to 10 hours, for example.

Reference numeral 4765 indicates a steep decent in the measured weight plot 4710, which indicates a rapid weight decrease corresponding to the actual offloading of processed waste from the drum 230. In contrast, reference numeral 4785 indicates a steep ascent in the measured weight plot 4710 which indicates a rapid weight increase corresponding to a waste load being added to the drum 230.

FIG. 47 depicts an air heater temperature plot 4725, a chamber inlet temperature plot 4726, and a chamber extract temperature plot 4727. The air heater temperature plot 4725 indicates a temperature range supplied to the drum 230. This temperature range may be significantly higher than the desired chamber temperature in order to account for environmental heat loss through travelling into the environment of the drum 230 and through the chamber waste inlet aperture 1065. Accordingly, a desired temperature of ~60° C. or between 50 and 70 degrees C. in the environment of the drum 230, as illustrated by the chamber inlet temperature plot 4726, may require an air heater temperature of between 170-190° C., creating a median air temperature of 180° C. However, where heat loss of the heated air that is rich in radicalised and/or ionised oxygen can be minimised, the air heater temperature can be reduced commensurately while achieving the target temperature range of 50 to 70 degrees C. (or preferably 55 to 65 degrees C.). The temperature range of the air heater temperature 4725 may be user configurable to adjust for the ideal decomposition temperature of different waste loads.

FIG. 47 depicts a time event 4728, indicating a power-outage event. In this event, the air heater temperature plot 4725 indicates a sudden drop in temperature, while the chamber inlet temperature plot 4726 and chamber extract temperature plot 4728 follow slower downward trends due to retained heat within the drum 230. The drum power draw 4720 falls immediately to zero at this event, indicating the drum has ceased processing waste. Power-outage events such as those depicted by time event 4728 may be triggered for maintenance, power saving, or operational purposes.

FIG. 47 depicts a time event 4729, indicating a low power offloading operation, where the drum weight plot 4710 indicates a reduction in drum weight, while the drum power draw 4720 drops to a lower power level, which may indicate a reduced RPM of the motor 420. During the time event 4729, the air heater temperature plot 4725 drops sharply, indicating cessation of heating during the time event 4729. Offloading operations as indicated by time event 4729 may allow continual processing for reduced interruption of waste load decomposition.

Specific values of tracked data are displayed at 4726 for user selectable times. This data may be stored and reviewed for maintenance purposes. In some embodiments, the data displayed at 4726 may be median values over a specified time range.

The waste processing machine 110 may have various logical states in which specific actions may be performed according to the instructions of the controller 210. In some embodiments the machine may have the following states: loading unprocessed waste, processing waste, unloading processed waste and standby state. In the loading unprocessed waste state, the inlet hatch 1710 may be opened to receive unprocessed waste into the mixing drum 230. In the processing waste state, the waste processing mixer 1400 may be operated to processes the waste along with air rich in radicalised or ionised oxygen. In the unloading waste state, the controller 210 may open the outlet chute 830 and initiate the removal of processed waste from the mixing drum 230. In the standby state, the waste processing mixer 1400 may cease the mixing of the waste and the ioniser 415 may cease operation to await addition of more unprocessed waste into the mixing drum 230.

In some embodiments, a minimum weight of residual contents in the drum may be maintained. This minimum weight may be maintained to quicken the structural breakdown of any freshly added unprocessed waste by acting as a starter for the waste processing operation. The minimum weight may also be maintained to quicken the release of moisture from freshly added unprocessed waste as the residual contents are usually relatively dry and processed. In some embodiments, the minimum weight may be in the range of 20 to 300 kg. In some embodiments, the minimum weight may be in the range of 50 to 250 kg. In some embodiments, the minimum weight may be in the range of 100 to 200 or 220 kg. A waste processing machine may have a configurable value of a minimum weight of residual contents within an acceptable range. While offloading waste after the generation of a waste offload trigger event, the control system 210 may offload waste such that the residual waste in the drum approximately reaches, but does not go below, the configured minimum weight value.

FIG. 51 depicts an alternative embodiment of a waste processing mixer 5100, of similar construction and arrangement to the embodiment described in FIG. 14. In this embodiment, three mixing blade fixing plates are positioned along the mixing shaft 5105. Direction of rotation of the waste processing mixer 5100 is indicated by 5101. The mixing blades affixed to the plates may be longer that other embodiments, and extend to within a 5 mm clearance of the drum chamber walls. A first, second, and third mixing blade fixing plate are positioned to provide a mixing, churning, and destructive action to waste loads. In the embodiment of FIG. 51, the mixing blade arms may extend proximally closer to the drum walls than in other embodiments, maximising the area affected by the action of the waste processing mixer 5100. This may allow the waste processing mixer to recombine waste residue with the main waste load that would otherwise accumulate in undesired areas.

In this embodiment, a first mixing blade assembly 5110 may be positioned on the distal end to the waste outlet hatch 1100, and be fitted with a number of plough blades 5112 and paddle blades 5111. FIG. 51E depicts one embodiment of a first mixing blade assembly 5110, alternately having three plough arms 5112 and three paddle arm 5111 around the central mixing blade fixing plate. The blade arms 5112 may comprise a mixing arm and a plough end 5132, the plough end 5132 having a pair of angled members, affixed to a mixing arm by an extension plate 5134, allowing the ploughs to reach a 5 mm clearance of the chamber wall. The angle of the plough ends may further allow waste residue accretions on the drum interior to be scraped and diverted along the length of the blade, and recombined back into the main waste load.

Figure 51A:
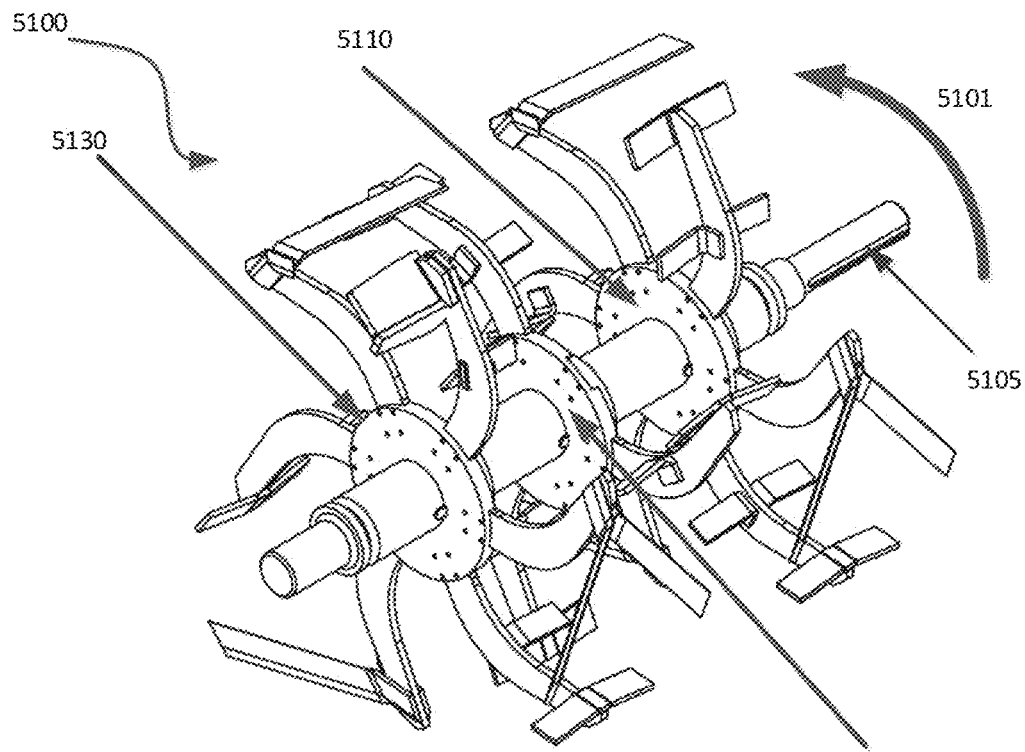
FIG. 51A is a front view of a waste processing mixer.
Figure 51B:
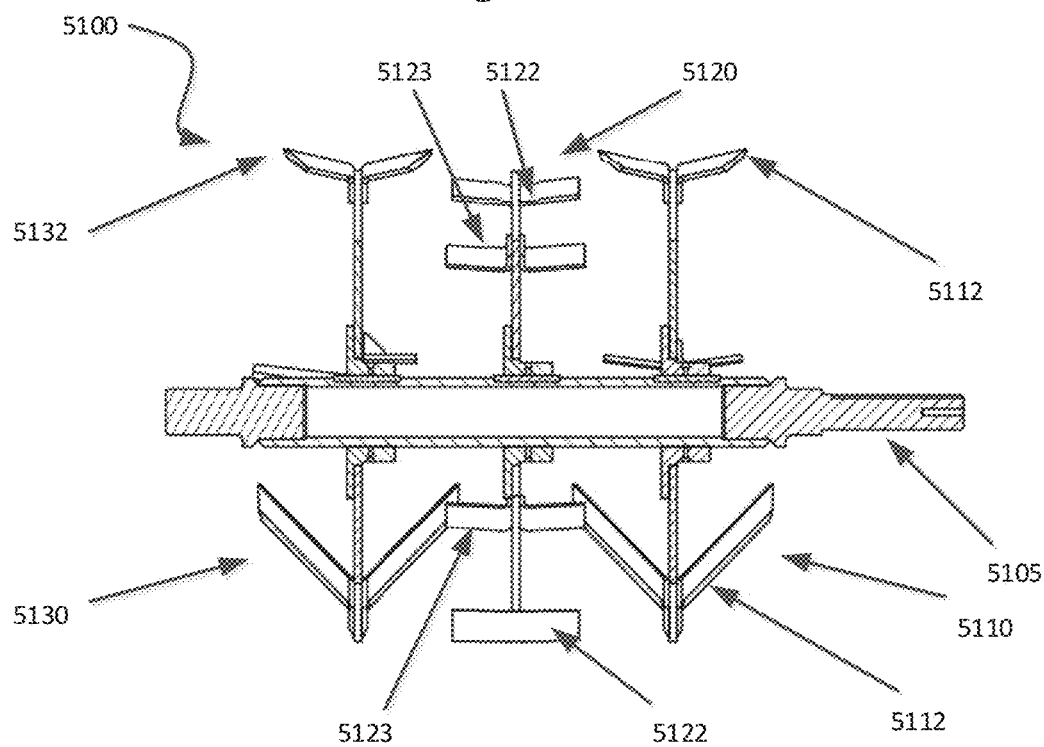
FIG. 51B is a front sectional view of a waste processing mixer.
Figure 51C:
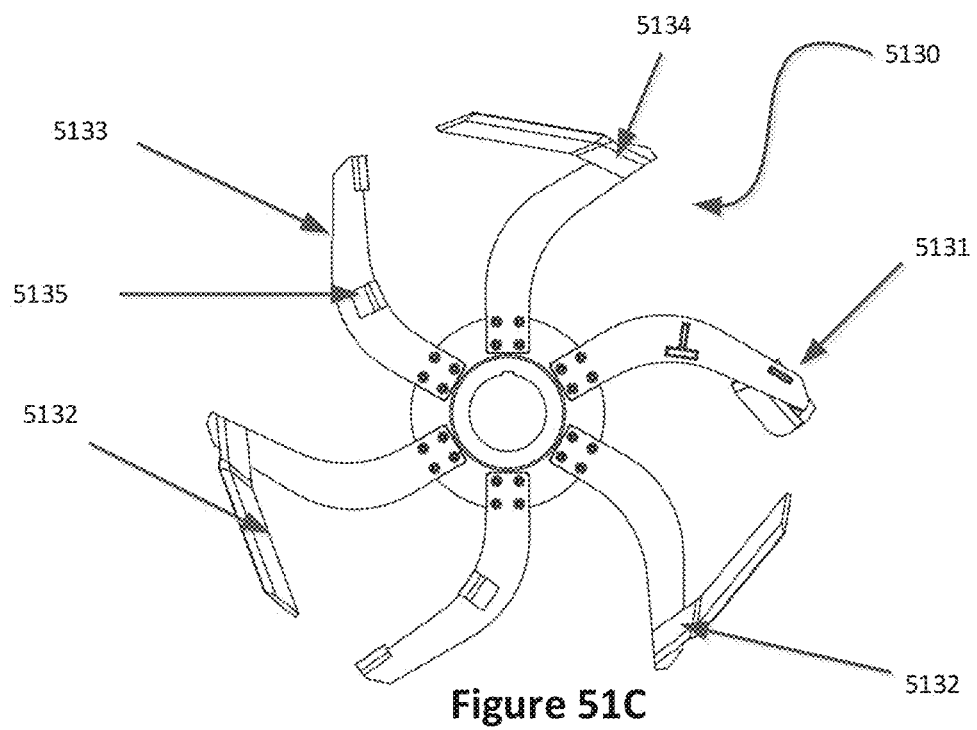
FIG. 51C is a side view of a first mixing blade fixture.

FIG. 51C depicts an embodiment of a third mixing blade assembly 5130, which may be installed proximally close to the outlet hatch 1100. The third mixing blade assembly 5130 may comprise a substantially similar configuration to the first mixing blade assembly 5110, replacing one paddle arm with an arm having a residue scoop 5131. Such a configuration may allow the third mixing blade assembly 5130 to provide both destructive and churning action to a waste load, and to actively churn, lift, and aerate waste by the action of the residue scoop. When the outlet hatch 1100 is deployed in a waste offloading operation, the action of the residue scoop deposits the processed waste residue on the deployed outlet hatch 1100. The residue scoop 5131 comprises a substantially similar construction as the embodiment 880, as previously described.

The positioned of a waste processing mixer may be determined by a blade position detector, the blade position detector may comprise a proximity sensor installed on the external housing of the motor 240 and a position wheel. The position wheel may comprise a metal disc affixed to the end of the mixing shaft 810 that extends out of the drum, arranged to rotate synchronously with the mixing shaft 810. Notches may be provided at points around the circumference of the position wheel, calibrated to the position of the mixing blades. During operation, the position wheel rotates, and the notches indicate to the proximity sensor the position of the blades. This allows the system to ensure that mixing blades are in optimal position to receive new waste loads, and otherwise indicate the presence of a fault in the blades or mixing shaft due to unexpected positions of the blades.

Figure 51D:
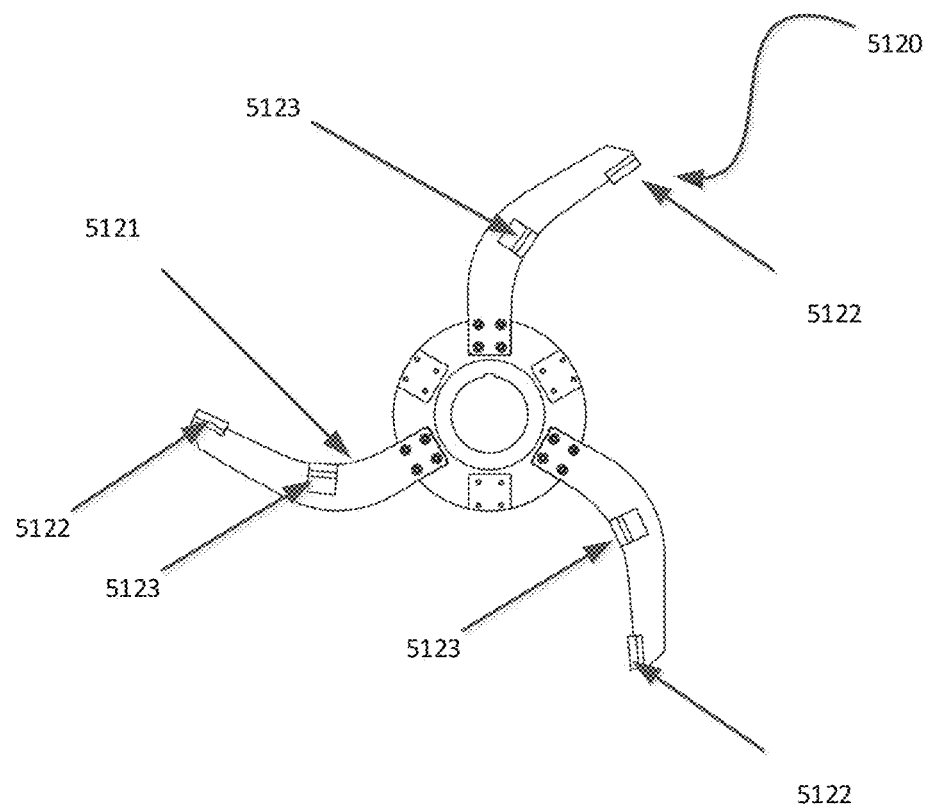
FIG. 51D is a side view of a second mixing blade fixture.
Figure 51E:
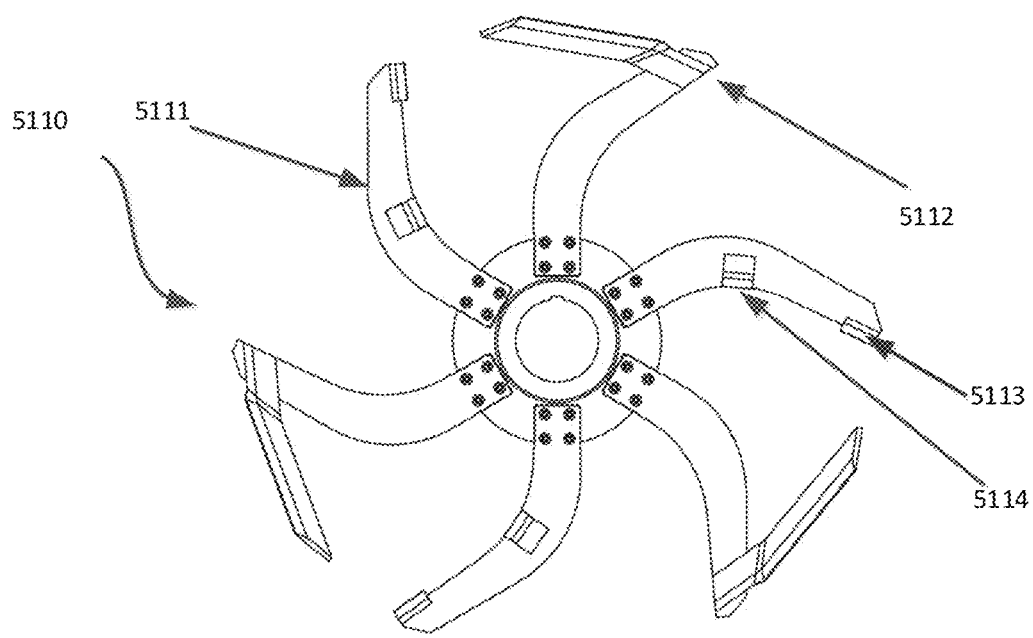
FIG. 51E is a side view of a third mixing blade fixture.

A second mixing blade assembly 5120 is depicted in FIG. 51D, having three paddle arms 5121 positioned around the central fixing plate. The second mixing blade assembly 5120 may be positioned between a first and third mixing blade assembly, and proximally close to the inlet hatch, the greater space between mixing blades allowing greater access to new waste loads when the input hatch 1710 is raised. The absence of plough ends further allows for waste to be dropped into the chamber without obstruction. The absence of plough ends on the second mixing blade assembly 5120 may permit the plough ends of the first and third assemblies to overlap the second assembly without interference, providing a broader coverage with a reduced number of ploughs.

In some embodiments, the paddle arms 5121, 5111, and 5133 comprise metal mixing arms having at least one mixing paddle end 5113, 5122, and a mixing paddle arrangement 5114, 5123, 5135. The mixing paddle arrangements may comprise a pair of paddles joined perpendicularly to the mixing blade arms using suitable fixing means such as rivets, screws, or welds. The mixing paddle arrangements 5114, 5123, 5135 may be disposed at a half way position along the length of the mixing blade arms. The positioning of the mixing paddle arrangements may allow the mixing blade to churn larger loads of waste residue, being closer to the middle of the drum. In some embodiments, a greater number of paddle arrangements may be provided on mixing blade arms to assist in the churning action of large waste loads.

Figure 52A:
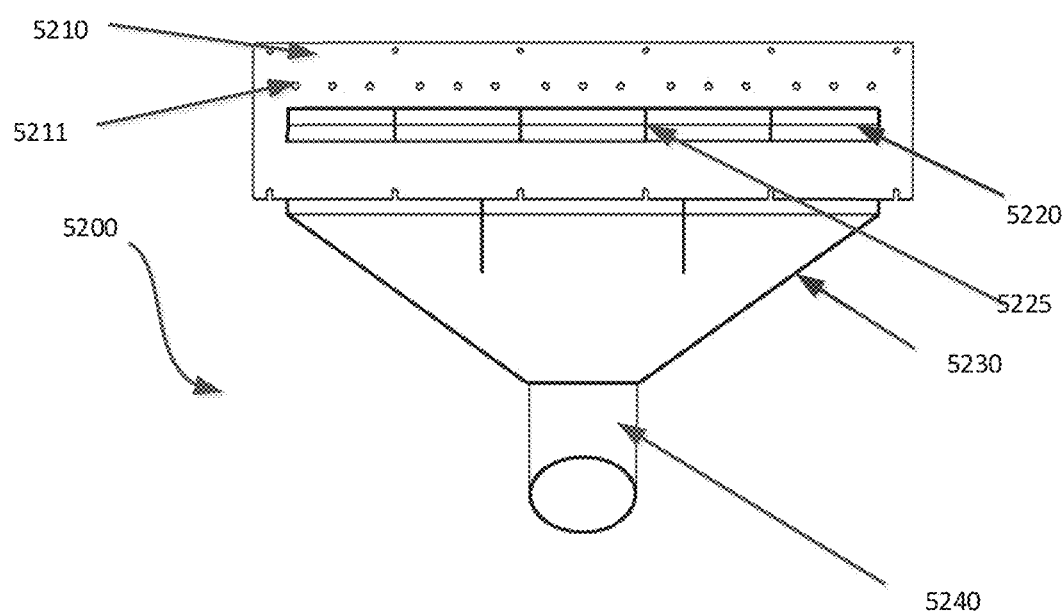
FIG. 52A is a front view of an air inlet plenum.
Figure 52B:
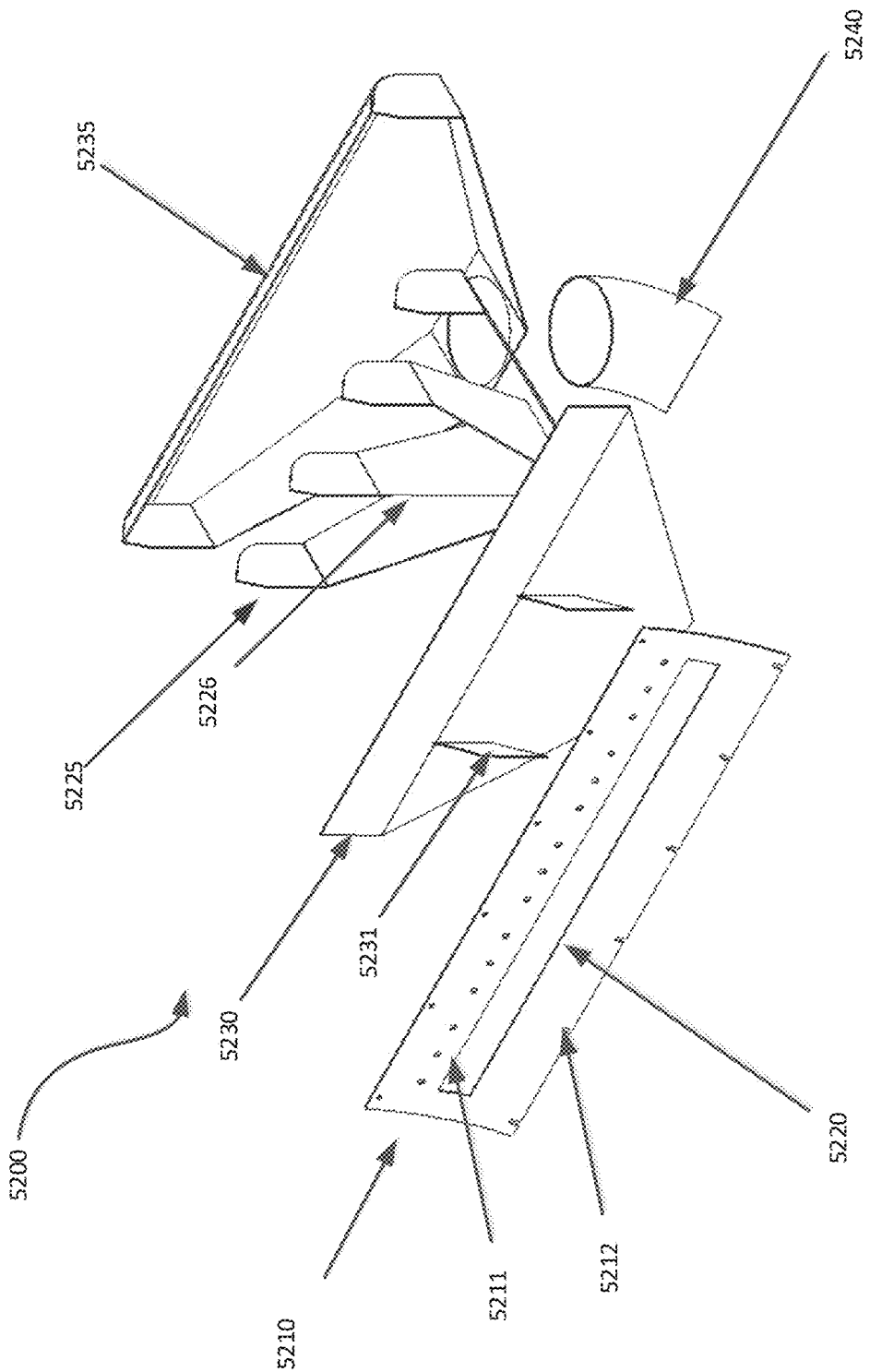
FIG. 52B is an exploded perspective view of an air inlet plenum.
Figure 54A:
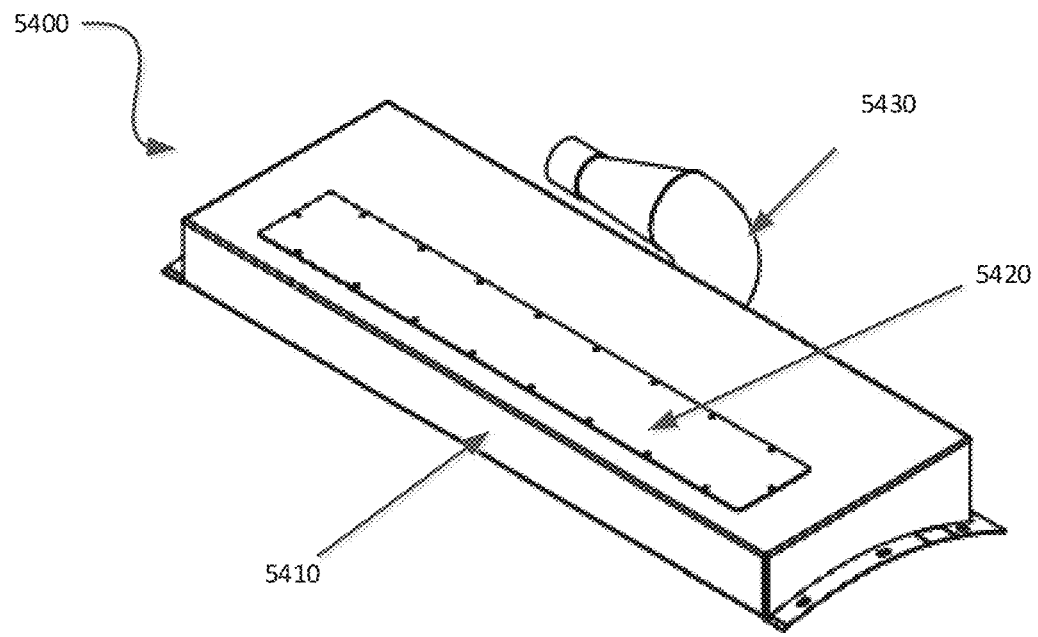
FIG. 54A is a perspective view of an exhaust outlet assembly.
Figure 54B:
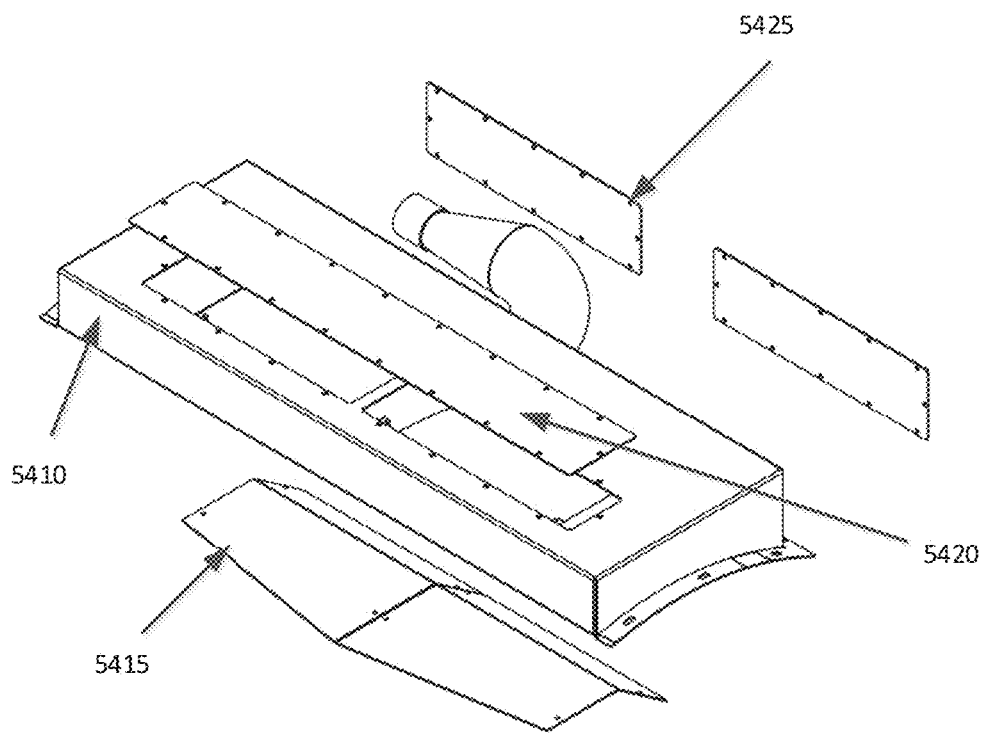
FIG. 54B is a perspective exploded view of an exhaust outlet assembly.
Figure 54C:
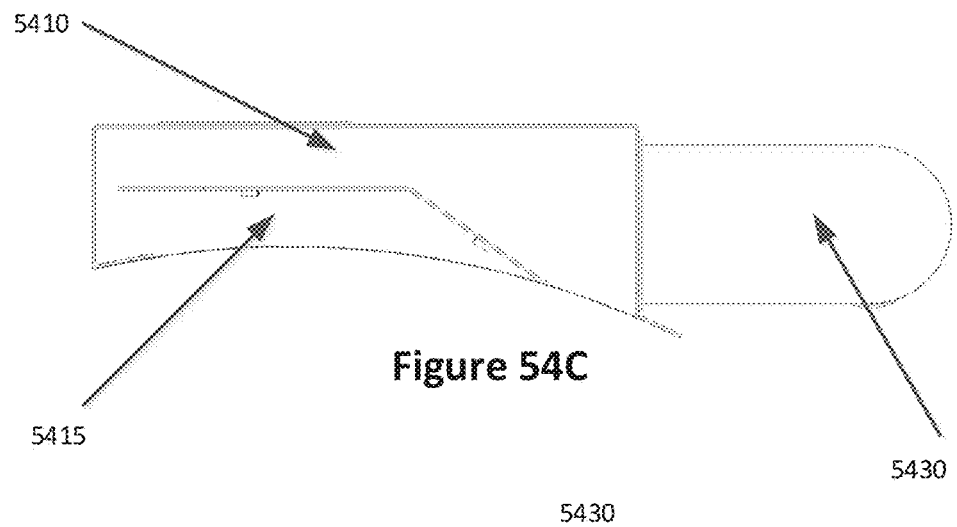
FIG. 54C is a side sectional view of an exhaust outlet assembly.
Figure 54D:
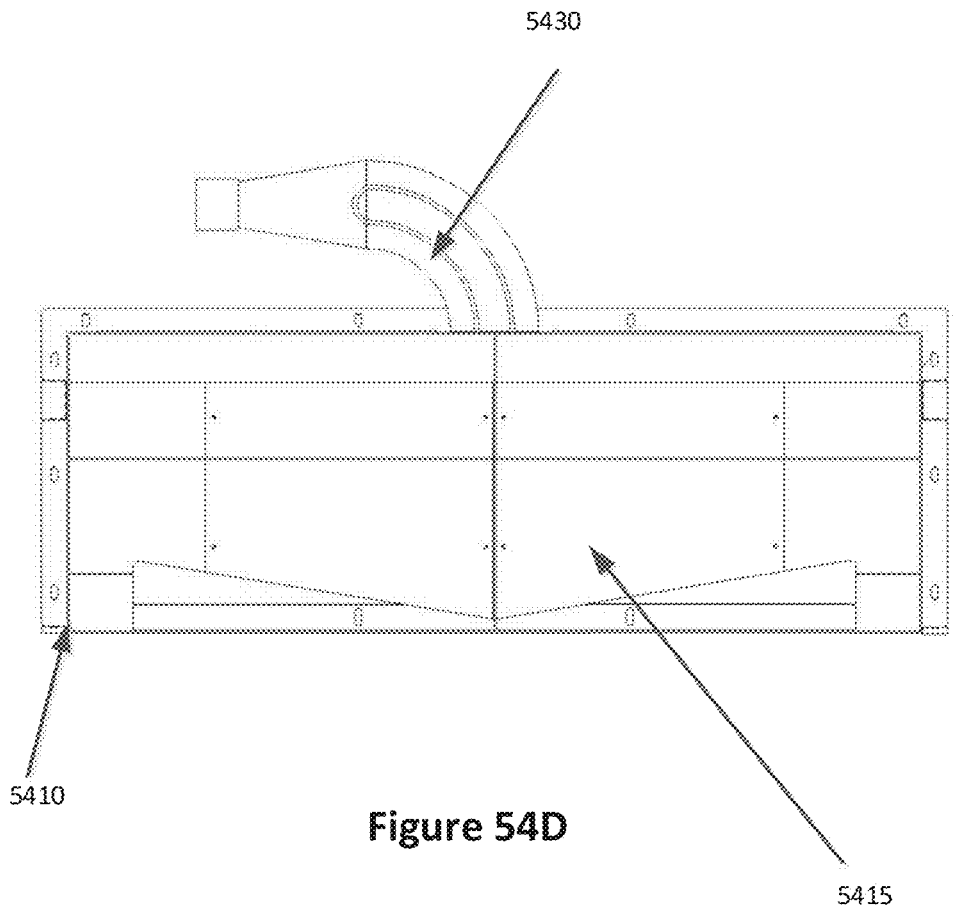
FIG. 54D is a top sectional view of an exhaust outlet assembly.

FIG. 52 depicts an embodiment of an air inlet plenum assembly 5200. The air inlet plenum assembly 5200 comprises an inlet facing plate 5210 having a facing inlet aperture 5220, an air stream separator 5225, a front housing 5230, rear housing 5235, and an inlet tube 5240. Heated and ionised air is blown into the assembly by air conduit sections 610 connected to the inlet tube 5240, and then separated into multiple air streams by the air stream separator 5225. The separated air streams provide heated and ionised air into a waste load within the chamber 1005.

The facing plate 5210 may comprise a rectangular body, of a length to cover the facing inlet aperture 5220. The length of the facing inlet aperture 5220 may be approximately proportionate to between 60%-90% of the total drum length (i.e. between vertical end walls), for example. This may provide an even distribution of heated ionised air along the length of the drum, thereby assisting in consistent waste processing. A rectangular slot is formed in the length of the facing plate 5210 to define the facing inlet aperture 5220.

The facing plate 5210 may connect directly to the exterior surface of the drum 230 and be of an approximately same curvature to that of the drum wall, sufficient to provide a sealed fit—thereby minimising potential leakage of heated ionised air between the two surfaces. The facing plate 5210 may affix the assembly 5200 with screws, rivets, or other fixing means. A series of apertures may be provided in the drum 230 to allow the separated air streams to blow into the chamber 1005. Some embodiments of these are described in greater detail in FIG. 57. The apertures may be aligned to the five separated air streams provided by the air inlet plenum assembly 5200. In some embodiments, more or fewer holes and air streams may be provided.

An array of fixing points 5211 are provided along the upper length of the facing plate 5210, acting as guides for connection points along the exterior of the drum wall and further guiding the affixing means of the inlet shield member 5310. In some embodiments these assist or act as guides for in spot welding, riveting, or other affixing means.

The facing plate 5210 further includes a series of fixing guides 5212 along the bottom edge of the plate. The fixing guides 5212 comprise at least one slot, formed in the body of the facing plate 5210 of a similar diameter to fixing screw threads, such that the facing plate 5210 may be slotted on and over the threads, thereby providing a matched and consistent fit when the screws are tightened. This may further assist in providing a matched and flush fit with the exterior of the drum wall.

The front housing 5230 comprises a flat facing panel and plate supports 5231. The facing panel comprises a narrow base extending outward lengthwise to an approximate length of the facing inlet aperture 5220. The plate supports 5231 comprise angled struts, on their upper edge of an approximately similar curvature to the facing plate 5210. At their front edge, the plate supports 5231 may be faced flat to connect the edge of the facing plate 5210 to the body of the front housing 5230, thereby providing support and mitigating vibration and misalignment of the assembly during operation.

The flat facing panel of the front housing 5230 may be of a height that when coupled with the rear housing 5235, forms an air outlet between the two components permitting airflow from an airstream between them. In some embodiments, this air outlet may be of a matched size to the facing inlet aperture 5220. In other embodiments, the outlet space may be narrower than the facing inlet aperture 5220.

The rear housing 5235 comprises a body having a narrow lower end, extending lengthwise towards the top of the housing. The narrow lower end has a circular slot of an approximately same diameter to that of the inlet tube 5240, thereby allowing a matched fit between the two components.

The inlet tube 5240 may comprise a bent tubular section, capable of interfacing and providing an airtight seal with air conduit sections 610.

The rear housing 5235 and front housing 5230 define an internal cavity of sufficient space to accommodate the air stream separator 5225. In some embodiments air stream separator 5225 comprises at least four separator sub-plena 5226, providing five channels of separated air when housed within the confines of the front and rear housings. In other embodiments, a greater number of separator sub-plena are provided depending on the overall drum length. This may ensure that a heated ionised air stream is consistently delivered to all areas of the waste load within the drum 230. FIG. 52D depicts a sectional view of the air inlet plenum assembly 5200, depicting the air stream separator 5225 within the cavity of the front and rear housings, and defining separate chambers for air streams.

FIG. 53 depicts a plenum shield 5300, affixed to the interior of the chamber 1005 to protect the apertures providing a heated ionised air stream into the chamber. The plenum shield 5300 comprises a shield member 5310 affixed to the chamber wall 5320. The profile of the plenum shield 5300 may be a flat top edge, with an angled portion defining a narrow space between the shield 5300 and the chamber wall. The angle of the shield 5300 may be further adjusted by an additional bend in the profile, towards the wall of the drum relative to the first angle, ensuring only the shield extends only a small distance from the drum wall. This may minimise the risk that the shield 5300 extends to within the rotational path of the blade arms of a waste processing mixture, thereby causing an obstruction. The minimum distance may further mitigate processed waste residue accumulating along the face of the shield 5300.

The angled profile of the shield member 5310 may further direct the heated ionised air stream down along the wall of the chamber 5320 and into a waste load during processing, allowing the heated ionised air stream to mix directly with the waste load.

The plenum shield 5300 may include a plurality of air stream struts 5311. The air stream struts 5311 may be disposed either side of a chamber inlet aperture to further direct and separate air streams into the waste load. This may assist in providing a more consistent airflow, rather than allowing the separated streams to combine before delivery into the waste load. The struts 5311 may further provide support for the plenum shield, assisting in resisting dislocation of the shield 5300 during a waste processing operation.

The means of affixing the shield member 5310 may be screws, rivets, or other fixing means. The plenum shield 5300 may reduce the accumulation of waste residue at the inlet apertures, and blocking the heated ionised air streams. The shield member 5310 may be angled away from the chamber wall 5320 allowing waste to fall along its face during processing operations. In such embodiments, the shield and apertures are provided in a complementary position to the angle of rotation of a waste processing mixer minimising the risk of mixing arms catching the edge of the shield member 5310.

FIG. 54 depicts an exhaust plenum assembly 5400, comprising an exhaust plenum housing 5410, top housing panel 5420, side housing panel 5425, exhaust baffle 5415, and exhaust tube 5430. The exhaust plenum assembly 5400 may be affixed to the top of the drum 230, and exhaust air through a series of exhaust apertures in the drum wall. In such embodiments, the air is drawn up through the exhaust apertures, both through the rising of the air and the negative pressure within the chamber provided by the exhaust fan 450. From within the processing chamber, the air that has aerated the food waste and consequently become more humid passes through the exhaust plenum housing 5410, circulating around and over the exhaust baffle 5415 and out through the exhaust tube 5430, under suction created by the exhaust fan 450.

The top housing panel 5420 and side housing panels 5425 may be removed to allow cleaning of the apertures, and the exhaust plenum housing interior.

The exhaust baffle 5415 may comprise an angled shield portion, having a v-shaped leading edge. In some embodiments, a pair of protruding rectangular prongs may extend from either lateral end of the baffle of a length allowing flush integration within the housing itself. In other embodiments, these prongs are omitted.

In some embodiments, a scrape bar 5810 is provided at the top position of the drum, spanning an approximate length similar to the exhaust plenum apertures depicted in FIG. 57. In some embodiments, the scrape bar 5810 comprises an elongate metal plate or bar, providing a clearance gap of between 1 mm to 5 mm between an inward-most scraping edge of the scrape bar 5810 and an outward-most edge or surface of a passing blade end 5840 of some or each of the mixing blades. The scrape bar 5810 may be positioned within the upper regions of the drum chamber such that a mixing blade arm (travelling in one rotational direction around a rotational path 5815) passes the scrape bar 5810 before reaching the exhaust plenum apertures 5720. The scrape bar 5810 may reduce excess waste residue that has accumulated on the mixing blades is reduced prior to reaching the position of the exhaust plenum apertures 5720. This may further mitigate exhausting large waste residue particles, and minimise the accumulation of waste residue within the exhaust plenum housing 5410 itself.

In some embodiments, the scrape bar 5810 comprises a flexible rubber wiper member 5820 extending radially inwardly to a scrape region. The flexible rubber wiper member 5820 may be of a sufficient length to overlap the rotational movement region of mixing arms to interfere somewhat with passing blade ends 5840. The wiper member 5820 is sufficiently elastically deformable to accommodate passing movement of the blade ends 5840 without damaging them while having sufficient stiffness to dislodge accumulated waste residue particles. This may assist to minimise the accumulation of waste both on the blade arms and within the exhaust plenum 5410 itself.

Figure 55:
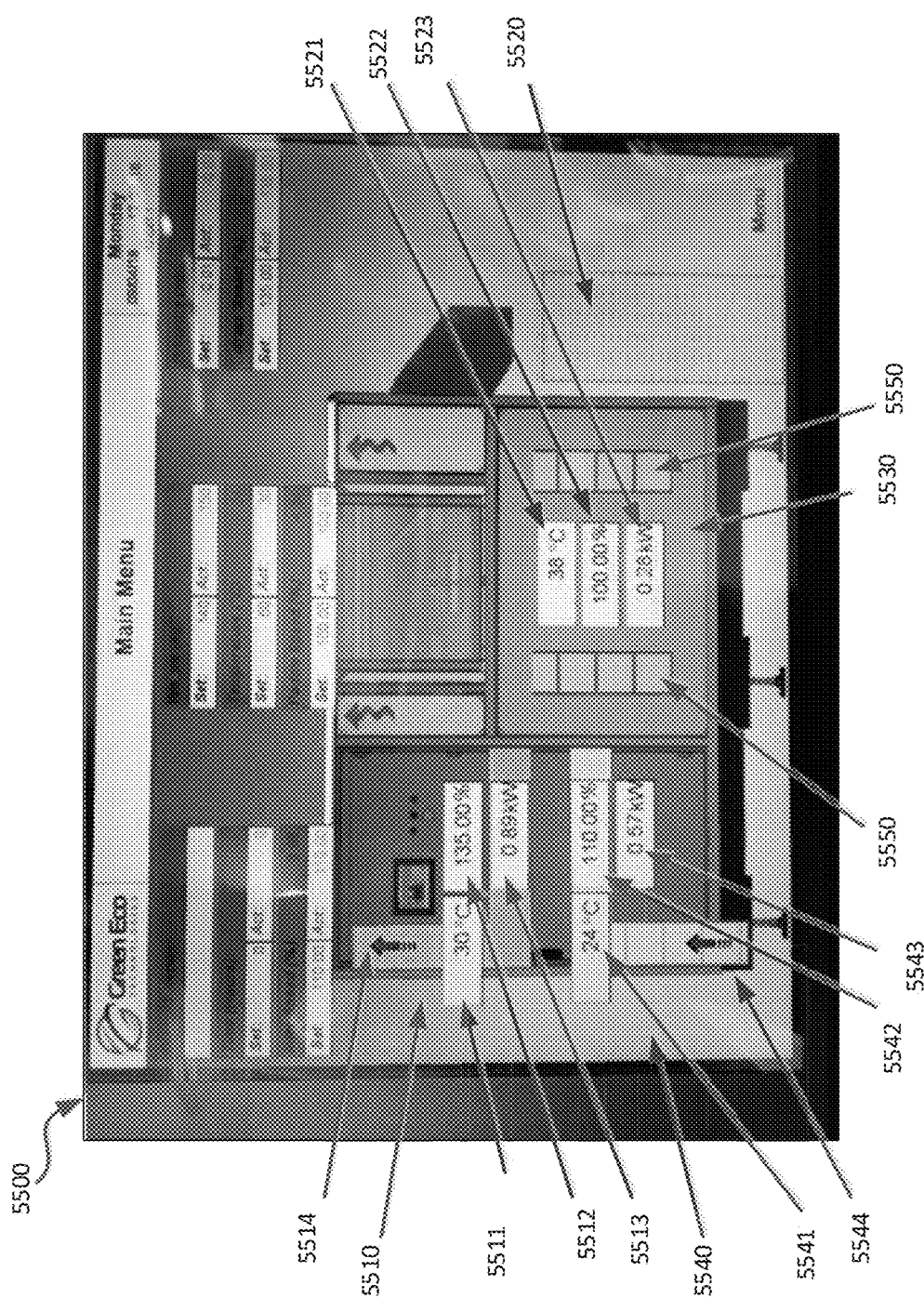
FIG. 55 is a an example user interface display image illustrating a main menu with navigation options and a display of various sensor data monitored by the controller of a waste processing machine according to some embodiments.

FIG. 55 depicts a display 5500 of the HMI 270 illustrating a main menu with some navigation options and a display of various sensor data monitored by the controller 210. The display 5500 further depicts real-time sensor information on top of the various system components, aiding in readability. FIG. 55 further depicts an air intake data display 5540, exhaust data display 5510, a bin position indicator 5520, and internal drum data display 5530. The positioning and graphical nature of the display elements may assist in at-a-glance recognition of the current system state.

The air intake data display 5540 comprises an intake air temperature 5541, intake power draw 5543, and percentage of base speed 5542, and intake air flow display 5544. The base speed percentage depicted in 5542 may be a set value for typical operation conditions for a type of waste load, or a dynamic value. 100% base speed may also be an indicative manufacturer set rating. In some embodiments, it may be preferable to run above or below the set 100% rating.

The air intake data display 5540 further depicts an air flow display 5544, which may comprise an animated scrolling bar, graphically depicting speed or on/off operation of the intake air flow system.

The exhaust data display 5510 comprises an exhaust air temperature 5511, exhaust power draw 5513, percentage of base speed 5512, and exhaust air flow display 5514. The base speed percentage depicted in 5512 may be a set value for typical operation conditions for a type of waste load, or a dynamic value. 100% base speed may also be an indicative manufacturer set rating. In some embodiments it may be preferable to run above or below the set 100% rating. With reference to both the air intake data display 5540 and the exhaust data display 5510, the percentage of base speed for the exhaust fan 450 may be set at a higher value than the intake fan 420, in order to create a negative pressure within the drum chamber, thereby allowing exhaust to be vented through the exhaust air system correctly.

The air intake data display 5540 further depicts an air flow display 5544, which may comprise an animated scrolling bar, graphically depicting speed or on/off operation of the intake air flow system.

The bin position indicator 5520 displays the absence of a bin under the outlet chute 830. By comparison, FIG. 38 depicts an alternative embodiment of a display of the HMI 207 where a bin is detected under the outlet chute 830.

The internal drum data display 5530 comprises a drum air temperature 5521, a percentage base rotation speed 5522, and an overall drum system power draw 5523. Animated scrolling bars 5550 may be included to provide a graphical representation of mixing shaft rotation speed.

Figure 56:
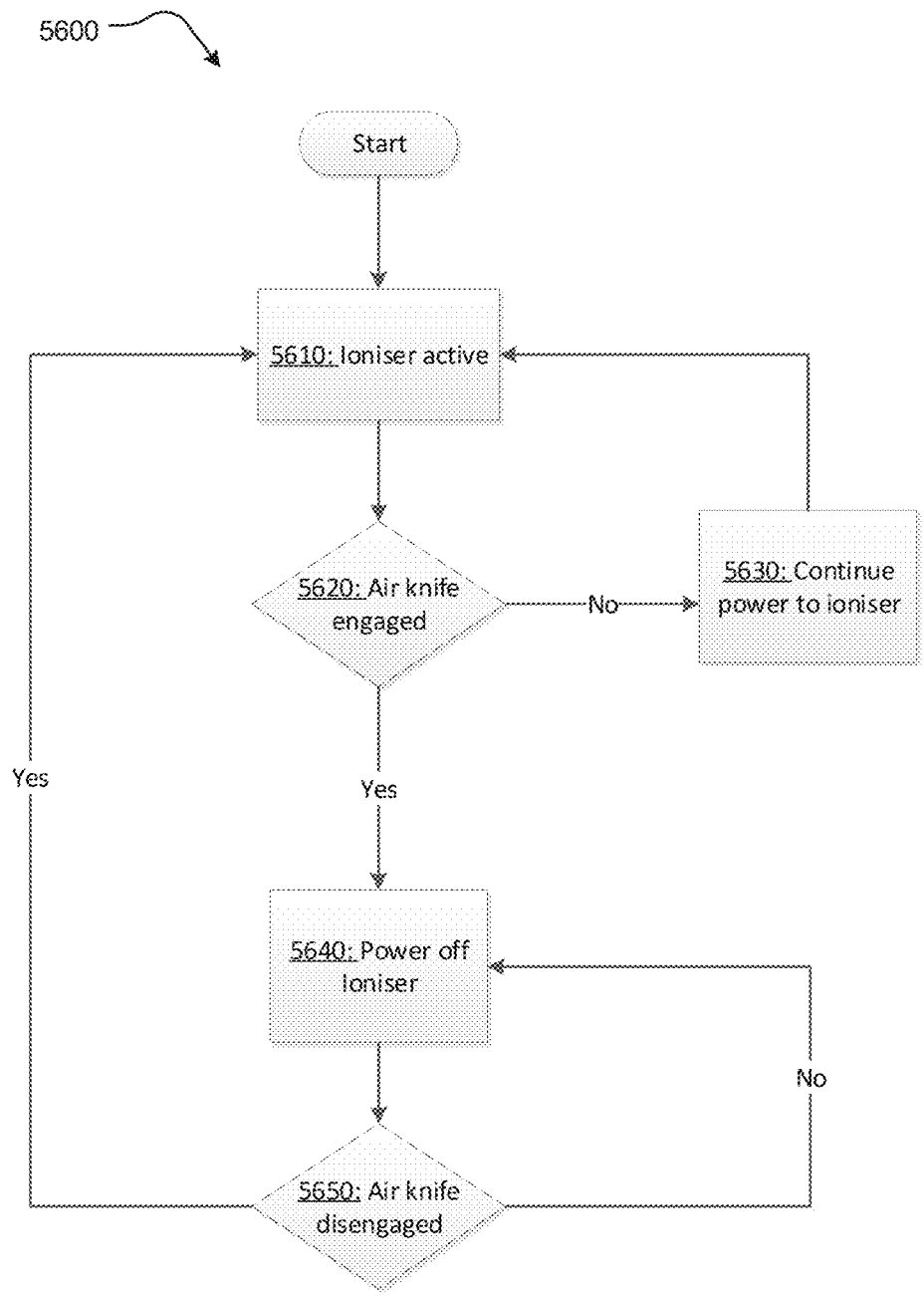
FIG. 56 is a flow chart illustrating a method of control of the ioniser of the waste processing machine according to some embodiments.

FIG. 56 is a flowchart 5600 of the operation of the ioniser 415 during a waste offloading operation. The air valve 425 directs airflow to the air heater 430 under normal processing operations, and to the air knife assembly 460 under offloading operations. In some embodiments, the ioniser 415 precedes the air valve 425 in the air flow system 220. In such embodiments, it may be preferable to cease power to the ioniser during offloading operations, ensuring that ionised air is not wasted by the air knife. At 5610, under the control of controller 210, the ioniser 415 is powered and active, ionising oxygen for use in waste processing. At 5620, the controller 210 detects whether an offloading operation has commenced, and air is diverted by the valve 425 to the air knife assembly 460. If an offloading operation has not commenced, power is continued to the ioniser 415 at 5630, until such a time as an offloading operation has commenced. If an offloading operation has commenced at 5620, and the valve 425 has redirected the airflow to the air knife assembly 460, the controller 210 depowers the ioniser 415 at 5640. Depowering the ioniser 415 during offloading operations may mitigate waste of ionised oxygen, and reduce the overall system power draw, as well as minimising the amount of ionised air that is released outside of the drum. At 5650, if the controller 210 detects an offloading operation has ceased, and the air knife assembly 460 is disengaged, controller 210 causes supply of power to the ioniser 415 from power supply 280 to resume.

Figure 57A:
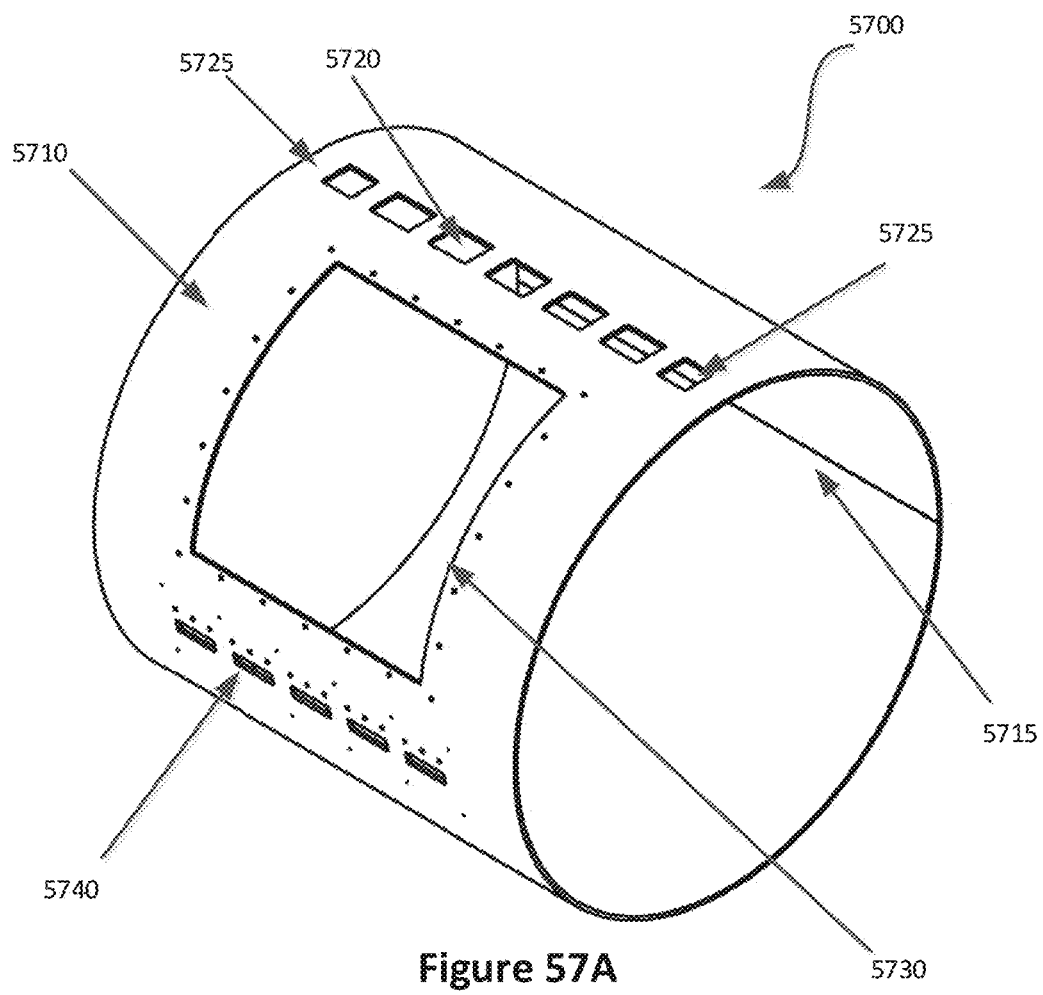
FIG. 57A is a perspective view of a of a waste processing chamber drum body according to some embodiments.
Figure 57B:
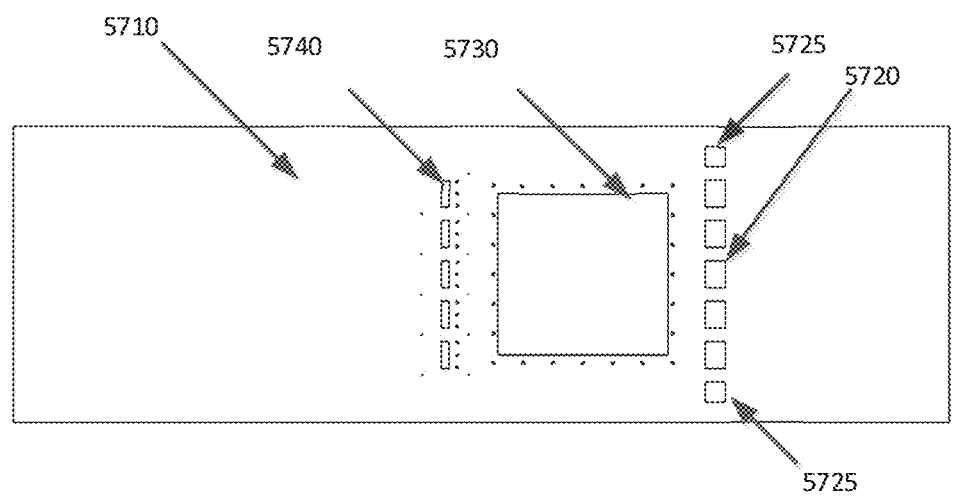
FIG. 57B is an unrolled plan view of a waste processing chamber drum body according to some embodiments.
Figure 58:
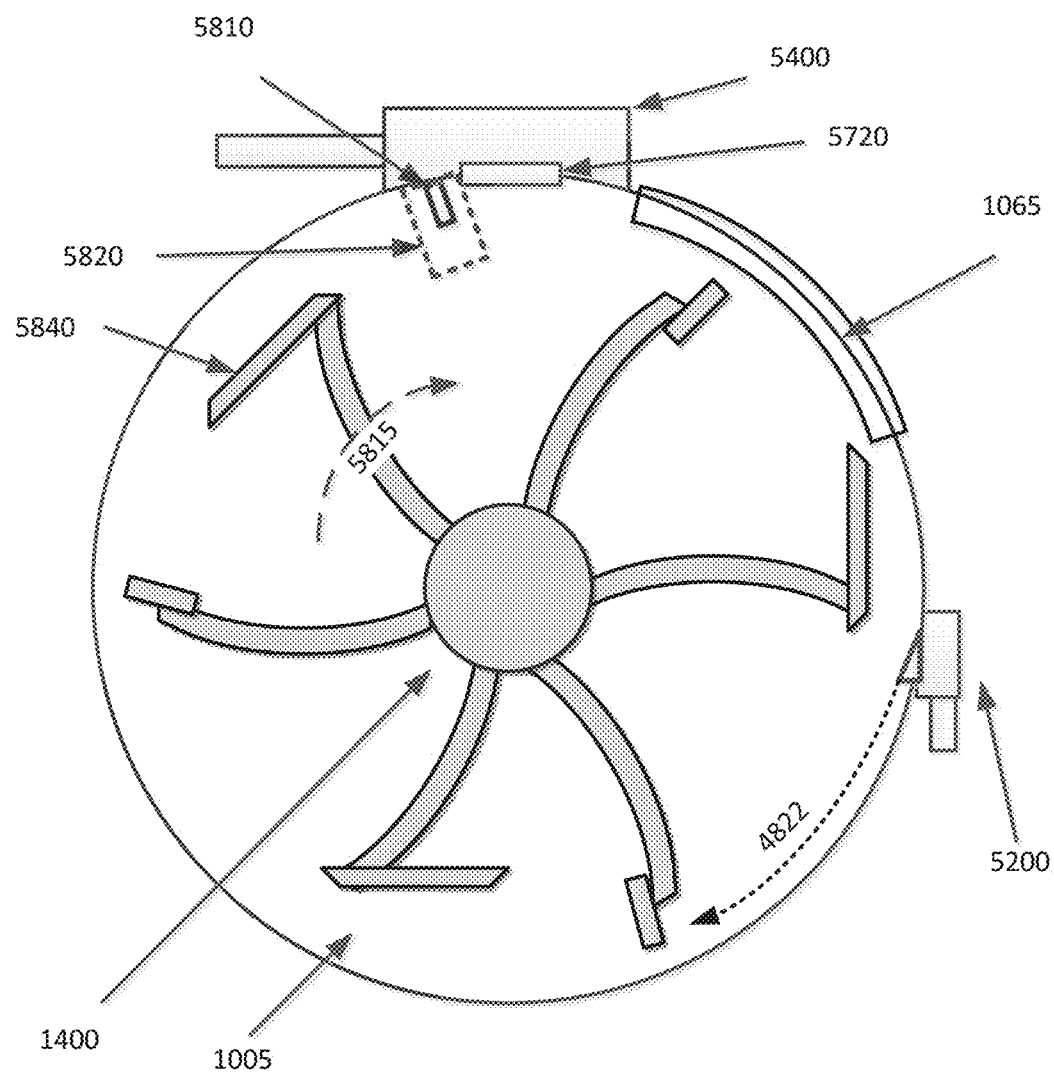
FIG. 58 is a schematic representation in end view to illustrate a typical position of a scrape bar and air exhaust outlet within the processing chamber of a waste processing machine.

FIG. 57A depicts an alternative embodiment of a chamber shroud 5700 (e.g. cylindrical portion of the processing drum) for any of the waste processing machine embodiments described herein, seen in perspective and without end walls and other components attached Chamber shroud 5700 comprises a shroud body 5710, exhaust plenum apertures 5720 and 5725, inlet plenum apertures 5740, and waste inlet aperture 5730. The chamber shroud 5700 may comprise a substantially similar generally cylindrical construction as the previously described embodiment of the chamber shroud 1010. The chamber shroud 5700 may comprise a metal sheet rolled into a cylindrical form and connected at join 5715, for example by welding. As shown in FIG. 57B, the shroud body 5710 may be initially formed as a flat metal sheet, which is then rolled into the cylindrical form shown in FIG. 57A.

The waste inlet aperture 5730 may comprise an aperture of between 60-75% of the overall shroud width, and of a height of approximately 20-25% of the total unrolled shroud length. With respect to the cylindrical profile of the shroud 5700, the waste inlet aperture 5730 may span a radial angle of between 45-90° (as seen looking along the horizontal axis about which the blades rotate) and be positioned starting at 0° relative to the horizontal midpoint on the shroud, or range between a starting point anywhere within 30° higher or lower than the horizontal midpoint.

The exhaust plenum apertures 5720 comprises one or a series of rectangular exhaust slots arranged along a straight line and positioned circumferentially higher (e.g. by about 150-250 mm) than the waste inlet aperture 5730. The one or more exhaust slots may cover an area extending a certain length beyond the lateral dimensions of the waste inlet aperture 5730. The lateral length of the shroud body 5710 may be around 1100 mm in some embodiments. The area of the exhaust slots may span an approximate length of between 60-95% of the overall cylindrical length (as seen looking along the horizontal axis about which the blades rotate) of the chamber shroud body 5710. For example, for a drum width of 1100 cm, the exhaust slots may span a length of around 890 cm, comprising approximately 81% of the total width. Thus, the exhaust slots may span an approximate length in the range of about 70-90% or 75-85% of the overall cylindrical length, for example. The number of rectangular exhaust slots may vary depending on drum dimensions. In some embodiments, the rectangular exhaust slots may comprise seven slots. The exhaust slots may be separated by web or bridging portions of the chamber shroud body 5710. The web or bridging portions may be evenly distributed across the entire cylindrical length of the shroud body 5710, and in some embodiments may define two end exhaust apertures 5725 smaller (more square) than the remainder. This may ensure sufficient support on either side of the shroud, maintaining structural integrity. In some embodiments, the exhaust plenum aperture slots comprise 75×100 mm apertures, with end apertures 5725 comprising 75×75 mm apertures. In other embodiments, the exhaust plenum apertures may be of a greater or smaller size, or be greater or fewer in number. With respect to the cylindrical profile of the shroud body 5710, the exhaust plenum apertures 5720 may be positioned between 90°-120° relative to the horizontal mid-point on the shroud.

The inlet plenum apertures 5740 comprises one or a series of rectangular inlet slots arranged along a straight line that is circumferentially lower (e.g. by about 150-250 mm) than the waste inlet aperture 5730, the inlet slots extending a certain length beyond the lateral dimensions of the waste inlet aperture 5730. The one or more inlet slots may span an approximate length of between 60-90% or 50-80% of the overall cylindrical length of the chamber shroud body 5710. For example, for a drum width of 1100 cm, the waste inlet aperture 5730 may span a length of 660 mm, comprising approximately 60% of the total drum width. Thus, the inlet slots may span an approximate length in the range of about 50-70% or 55-65% of the overall cylindrical length, for example. The number of rectangular inlet slots may vary depending on drum dimensions, and correspond to one more than the number of vanes of the air inlet plenum assembly 5200, such that each separated air stream may be aligned to one of the inlet plenum apertures 5740. In some embodiments, the inlet plenum apertures 5740 may comprise five 30 mm by 100 mm slots. In other embodiments, the inlet plenum apertures may be of a greater or smaller size, or be greater or fewer in number. With respect to the cylindrical profile of the shroud body 5710, the inlet plenum aperture 5730 may be positioned at the horizontal midpoint of the shroud, or up to 20° above or 45° below the horizontal midpoint.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:
1. A machine for food waste processing, comprising:
a power supply;
a control system coupled to the power supply;
a mixing drum defining a mixing chamber and having a volumetric capacity of 2000 litres or less;
a mixing shaft having mixing blades extending from the mixing shaft, the mixing shaft being configured to rotate to move the mixing blades within the mixing chamber;
an ioniser coupled to the power supply and arranged to provide a source of air that is rich in reactive oxygen species;
a heater and a fan coupled to the power supply and arranged to receive the source of air, the heater and fan cooperating to provide a source of heated gas rich in ionised oxygen to the mixing chamber, wherein the heated gas is between about 50 and about 70 degrees C. and/or wherein the environment in the processing drum is heated to a temperature in the range of 50 to 70 degrees C.;
a motor arranged to draw power from the power supply and to drive rotation of the mixing shaft;
wherein the mixing drum defines an input aperture to receive food waste and an outlet to disgorge processed waste residue;
wherein the control system is configured to operate the motor to drive the mixing shaft for multiple hours while monitoring operating parameters of the machine in order to produce a processed waste residue, wherein the residue comprises or consists essentially of substantially dried particulate.

2. The machine of claim 1, wherein the control system is configured to monitor the power draw of the motor and to determine a time of peak power draw of the motor.

3. The machine of claim 1, wherein the control system is configured to determine that the processed waste residue is ready for disgorgement from the outlet based on one or more process completion conditions.

4. The machine of claim 3, wherein the one or more completion conditions include a predetermined time elapsing after the time of peak power draw.

5. The machine of claim 4, wherein the predetermined time is between about 4 hours and about 7 hours.

6. The machine of claim 3, wherein the machine comprises a humidity sensor to sense humidity in the mixing chamber, and wherein the one or more completion conditions include a humidity level in the mixing chamber being below a humidity threshold.

7. The machine of claim 3, wherein the machine comprises a temperature sensor to sense air temperature in the mixing chamber or at an exhaust outlet of the mixing drum, and wherein the one or more completion conditions include a sensed temperature level of the temperature sensor being within a predetermined temperature range.

8. The machine of claim 1, wherein the outlet is disposed in an outer wall of the drum at a position that is vertically above a position of the mixing shaft.

9. The machine of claim 1, wherein the mixing shaft has at least one scoop coupled thereto, the at least one scoop being configured to carry processed waste residue to the position of the outlet.

10. The machine of claim 1, wherein the control system is configured to automatically initiate disgorgement of processed waste residue in response to determining that the processed waste residue is ready for disgorgement.

11. The machine of claim 10, wherein the control system monitors a weight of the drum during disgorgement to monitor the weight of disgorged residue and to determine the weight of residue remaining in the drum, wherein the control system is configured to cease disgorgement of processed waste residue when the weight of residue remaining in the drum reaches a predetermined minimum threshold level, whereby an amount of at least 20 kg of processed waste residue remains in the drum after disgorgement ceases.

* * * * *